(12) United States Patent
Jung et al.

(10) Patent No.: US 10,738,045 B2
(45) Date of Patent: *Aug. 11, 2020

(54) PESTICIDALLY ACTIVE HETEROCYCLIC DERIVATIVES WITH SULPHUR AND CYCLOPROPYL CONTAINING SUBSTITUENTS

(71) Applicant: SYNGENTA PARTICIPATIONS AG, Basel (CH)

(72) Inventors: Pierre Joseph Marcel Jung, Stein (CH); Andrew Edmunds, Stein (CH); Michel Muehlebach, Stein (CH); Roger Graham Hall, Stein (CH)

(73) Assignee: Syngenta Participations AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/778,143

(22) PCT Filed: Nov. 16, 2016

(86) PCT No.: PCT/EP2016/077814
§ 371 (c)(1),
(2) Date: May 22, 2018

(87) PCT Pub. No.: WO2017/089190
PCT Pub. Date: Jun. 1, 2017

(65) Prior Publication Data
US 2018/0346462 A1 Dec. 6, 2018

(30) Foreign Application Priority Data
Nov. 23, 2015 (EP) .................................... 15195793

(51) Int. Cl.
C07D 471/04 (2006.01)
A01N 43/90 (2006.01)

(52) U.S. Cl.
CPC ............ C07D 471/04 (2013.01); A01N 43/90 (2013.01)

(58) Field of Classification Search
CPC .................................................. C07D 471/04
See application file for complete search history.

(56) References Cited

U.S. PATENT DOCUMENTS 10,005,775 B2 * 6/2018 Jung .................... C07D 471/04

FOREIGN PATENT DOCUMENTS

| EP | 2 394 995 A1 | 2/2010 | |
|---|---|---|---|
| EP | 2 975 039 A1 | 3/2014 | |
| WO | 2012086848 A1 | 6/2012 | |
| WO | 2014142292 A1 | 9/2014 | |
| WO | 2015121136 A1 | 8/2015 | |
| WO | 2016023954 A2 | 2/2016 | |
| WO | WO-2017001314 A1 * | 1/2017 | ........... C07D 471/04 |

OTHER PUBLICATIONS

Extended European Search Report dated Apr. 28, 2016 from EP 15195793.3 (8 pages).
Notification of Transmittal of the International Search Report and the Written Opinion of the International Search Authority, or the Declaration, dated Feb. 21, 2017 from International Appln. No. PCT/EP2016/077814 (14 pages).

* cited by examiner

*Primary Examiner* — David K O'Dell
(74) *Attorney, Agent, or Firm* — Baker & Hostetler, LLP; Toni-Junell Herbert

(57) ABSTRACT

Compounds of formula (I), wherein the substituents are as defined in claim 1, and the agrochemically acceptable salts, stereoisomers, enantiomers, tautomers and N-oxides of those compounds, can be used as insecticides and can be prepared in a manner known per se.

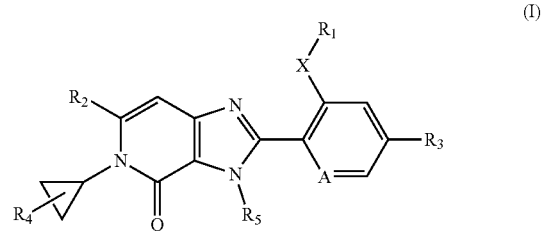

12 Claims, No Drawings

PESTICIDALLY ACTIVE HETEROCYCLIC DERIVATIVES WITH SULPHUR AND CYCLOPROPYL CONTAINING SUBSTITUENTS

CROSS-REFERENCE TO RELATED APPLICATIONS

This application is a 371 National Stage application of International Application No. PCT/EP2016/077814, filed Nov. 16, 2016, which claims priority to European Application No. 15195793.3, filed Nov. 23, 2015, the entire contents of which are hereby incorporated by reference.

The present invention relates to pesticidally active, in particular insecticidally active heterocyclic derivatives containing sulphur substituents, to compositions comprising those compounds, and to their use for controlling animal pests (including arthropods and in particular insects or representatives of the order Acarina).

Heterocyclic compounds with pesticidal action are known and described, for example, in WO 2012/086848 and WO 2013/018928.

There have now been found novel pesticidally active heterocyclic derivatives with sulphur containing phenyl and pyridyl substituents.

The present invention accordingly relates to compounds of formula I,

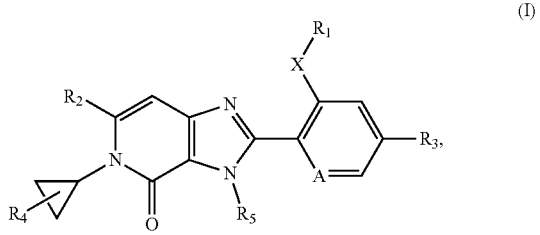

(I)

wherein
A is CH or N;
X is S, SO or $SO_2$;
$R_1$ is $C_1$-$C_4$alkyl;
$R_2$ is $C_1$-$C_6$haloalkyl, $C_1$-$C_6$haloalkoxy, $C_1$-$C_4$haloalkylsulfanyl, $C_1$-$C_4$haloalkylsulfinyl or $C_1$-$C_4$haloalkylsulfonyl; or
$R_2$ is cyclopropyl which can be mono- or polysubstituted by substituents selected from the group consisting of halogen, cyano, $C_1$-$C_4$ haloalkyl and $C_1$-$C_4$alkyl;
$R_3$ is hydrogen, halogen, cyano, $C_1$-$C_4$haloalkyl, $C_1$-$C_4$haloalkylsulfanyl, $C_1$-$C_4$haloalkylsulfinyl or $C_1$-$C_4$haloalkylsulfonyl; or is $C_3$-$C_6$cycloalkyl which can be mono- or polysubstituted by substituents selected from the group consisting of halogen, $C_1$-$C_4$alkyl, $C_1$-$C_4$haloalkyl and cyano; or
$R_3$ is phenyl which can be mono- or polysubstituted by substituents selected from the group consisting of halogen, cyano, nitro, $C_2$-$C_6$alkenyl, $C_2$-$C_6$haloalkenyl, $C_2$-$C_6$alkynyl, $C_2$-$C_6$haloalkynyl, $C_1$-$C_4$alkoxy$C_1$-$C_4$alkyl, $C_1$-$C_4$alkyl, $C_1$-$C_4$haloalkyl, $C_1$-$C_4$haloalkoxy, $C_1$-$C_4$alkoxy, $C_1$-$C_4$haloalkylsulfanyl, $C_1$-$C_4$haloalkylsulfinyl, $C_1$-$C_4$haloalkylsulfonyl, $C_1$-$C_4$alkylsulfanyl, $C_1$-$C_4$alkylsulfinyl, $C_1$-$C_4$alkylsulfonyl and —C(O)$C_1$-$C_4$haloalkyl; or
$R_3$ is pyrimidinyl or pyridinyl linked via a carbon atom to the ring which contains the substituent A, said pyrimidinyl or pyridinyl can be mono- or polysubstituted by substituents selected from the group consisting of halogen, cyano, nitro, $C_2$-$C_6$alkenyl, $C_2$-$C_6$haloalkenyl, $C_2$-$C_6$alkynyl, $C_2$-$C_6$haloalkynyl, $C_1$-$C_4$alkoxy$C_1$-$C_4$alkyl, $C_1$-$C_4$alkyl, $C_1$-$C_4$haloalkyl, $C_1$-$C_4$haloalkoxy, $C_1$-$C_4$alkoxy, $C_1$-$C_4$haloalkylsulfanyl, $C_1$-$C_4$haloalkylsulfinyl, $C_1$-$C_4$haloalkylsulfonyl, $C_1$-$C_4$alkylsulfanyl, $C_1$-$C_4$alkylsulfinyl, $C_1$-$C_4$alkylsulfonyl and —C(O)$C_1$-$C_4$haloalkyl; or
$R_3$ is a five membered aromatic ring system linked via a nitrogen atom to the ring which contains the substituent A, said ring system can be mono- or polysubstituted by substituents selected from the group consisting of halogen, cyano, nitro, $C_2$-$C_6$alkenyl, $C_2$-$C_6$haloalkenyl, $C_2$-$C_6$alkynyl, $C_2$-$C_6$haloalkynyl, $C_1$-$C_4$alkoxy $C_1$-$C_4$alkyl, $C_1$-$C_4$alkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl, —C(O)$C_1$-$C_4$alkyl, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl; and said ring system contains 1, 2 or 3 heteroatoms selected from the group consisting of nitrogen, oxygen and sulphur, where said ring system may not contain more than one oxygen atom and not more than one sulfur atom;
$R_4$ is hydrogen, halogen, cyano, $C_1$-$C_4$alkyl or $C_1$-$C_4$haloalkyl; and
$R_5$ is $C_1$-$C_4$alkyl; and agrochemically acceptable salts, stereoisomers, enantiomers, tautomers and N-oxides of the compounds of formula I.

Compounds of formula I which have at least one basic centre can form, for example, acid addition salts, for example with strong inorganic acids such as mineral acids, for example perchloric acid, sulfuric acid, nitric acid, a phosphorus acid or a hydrohalic acid, with strong organic carboxylic acids, such as $C_1$-$C_4$alkanecarboxylic acids which are unsubstituted or substituted, for example by halogen, for example acetic acid, such as saturated or unsaturated dicarboxylic acids, for example oxalic acid, malonic acid, succinic acid, maleic acid, fumaric acid or phthalic acid, such as hydroxycarboxylic acids, for example ascorbic acid, lactic acid, malic acid, tartaric acid or citric acid, or such as benzoic acid, or with organic sulfonic acids, such as $C_1$-$C_4$alkane- or arylsulfonic acids which are unsubstituted or substituted, for example by halogen, for example methane- or p-toluenesulfonic acid. Compounds of formula I which have at least one acidic group can form, for example, salts with bases, for example mineral salts such as alkali metal or alkaline earth metal salts, for example sodium, potassium or magnesium salts, or salts with ammonia or an organic amine, such as morpholine, piperidine, pyrrolidine, a mono-, di- or tri-lower-alkylamine, for example ethyl-, diethyl-, triethyl- or dimethylpropylamine, or a mono-, di- or trihydroxy-lower-alkylamine, for example mono-, di- or triethanolamine.

The alkyl groups occurring in the definitions of the substituents can be straight-chain or branched and are, for example, methyl, ethyl, n-propyl, isopropyl, n-butyl, sec-butyl, iso-butyl, tert-butyl, pentyl, hexyl, nonyl, decyl and their branched isomers. Alkylsulfanyl, alkylsulfinyl, alkylsulfonyl, alkoxy, alkenyl and alkynyl radicals are derived from the alkyl radicals mentioned. The alkenyl and alkynyl groups can be mono- or polyunsaturated.

Halogen is generally fluorine, chlorine, bromine or iodine. This also applies, correspondingly, to halogen in combination with other meanings, such as haloalkyl or halophenyl.

Haloalkyl groups preferably have a chain length of from 1 to 6 carbon atoms. Haloalkyl is, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl.

Alkoxy is, for example, methoxy, ethoxy, propoxy, i-propoxy, n-butoxy, isobutoxy, sec-butoxy and tert-butoxy and also the isomeric pentyloxy and hexyloxy radicals.

Alkoxyalkyl groups preferably have a chain length of 1 to 6 carbon atoms containing one or more oxygen atoms. Alkoxyalkyl is, for example, methoxymethyl, methoxyethyl, ethoxymethyl, ethoxyethyl, n-propoxymethyl, n-propoxyethyl, isopropoxymethyl, isopropoxyethyl or a dialkoxyalkyl derivative such as for example —CH$_2$OCH$_2$CH$_2$OCH$_3$.

Alkoxycarbonyl is for example methoxycarbonyl (which is C$_1$alkoxycarbonyl), ethoxycarbonyl, propoxycarbonyl, isopropoxycarbonyl, n-butoxycarbonyl, tert-butoxycarbonyl, n-pentoxycarbonyl or hexoxycarbonyl.

The cycloalkyl groups preferably have from 3 to 6 ring carbon atoms, for example cyclopropyl, cyclobutyl, cyclopentyl and cyclohexyl.

In the context of this invention "mono- to polysubstituted" in the definition of the substituents, means typically, depending on the chemical structure of the substituents, monosubstituted to seven-times substituted, preferably monosubstituted to five-times substituted, more preferably mono-, di- or tri-substituted.

As used herein, the term "C$_2$-C$_6$alkynyl" refers to a straight or branched hydrocarbon chain radical group consisting solely of carbon and hydrogen atoms, containing at least one triple bond, having from two to six carbon atoms, and which is attached to the rest of the molecule by a single bond. The term "C$_2$-C$_4$alkynyl" and "C$_2$-C$_3$alkynyl" are to be construed accordingly. Examples of C$_2$-C$_6$alkynyl include, but are not limited to, ethynyl, prop-1-ynyl, but-1-ynyl, but-2-ynyl.

As used herein, the term "C$_2$-C$_6$ alkenyl" refers to a straight or branched hydrocarbon chain radical group consisting solely of carbon and hydrogen atoms, containing at least one double bond, having from two to six carbon atoms, and which is attached to the rest of the molecule by a single bond. The term "C$_2$-C$_4$alkenyl" and "C$_2$-C$_3$alkenyl" are to be construed accordingly. Examples of C$_2$-C$_6$alkenyl include, but are not limited to, .prop-1-enyl, but-1-enyl, but-2-enyl.

Alkylsulfanyl is for example methylsulfanyl, ethylsulfanyl, propylsulfanyl, isopropylsulfanyl, butylsulfanyl, pentylsulfanyl, and hexylsulfanyl.

Alkylsulfinyl is for example methylsulfinyl, ethylsulfinyl, propylsulfinyl, isopropylsulfinyl, a butylsulfinyl, pentylsulfinyl, and hexylsulfinyl.

Alkylsulfonyl is for example methylsulfonyl, ethylsulfonyl, propylsulfonyl, isopropylsulfonyl, butylsulfonyl, pentylsulfonyl, and hexylsulfonyl.

Haloalkylsulfanyl is for example trifluoromethylsulfanyl, 2,2,2-trifluoroethylsulfanyl, and pentafluoroethylsulfanyl.

Haloalkylsulfinyl is for example trifluoromethylsulfinyl, 2,2,2-trifluoroethylsulfinyl, or pentafluoroethylsulfinyl.

Haloalkylsulfonyl is for example trifluoromethylsulfonyl, 2,2,2-trifluoroethylsulfonyl, and pentafluoroethylsulfonyl.

In the context of this invention, examples of five membered, aromatic linked via a nitrogen atom to the ring which contains the substituent A are, but are not limited to, pyrazolyl; Imidazolyl; pyrrolyl; triazolyl, tetrazolyl.

The compounds of formula I according to the invention also include hydrates which may be formed during the salt formation.

Preferred are compounds of formula I, wherein $R_1$ is C$_1$-C$_4$alkyl;

$R_2$ is C$_1$-C$_6$haloalkyl, C$_1$-C$_4$haloalkylsulfanyl, C$_1$-C$_4$haloalkylsulfinyl, C$_1$-C$_4$haloalkylsulfonyl or cyclopropane, said cyclopropane can be mono- or polysubstituted by substituents selected from the group consisting of halogen, cyano, C$_1$-C$_4$ haloalkyl and C$_1$-C$_4$alkyl;

$R_3$ is hydrogen, halogen, cyano, C$_1$-C$_6$haloalkyl, C$_3$-C$_6$cycloalkyl, C$_1$-C$_6$haloalkylsulfanyl, C$_1$-C$_6$haloalkylsulfinyl, C$_1$-C$_6$haloalkylsulfonyl, C$_1$-C$_6$haloalkoxy, —C(O)C$_1$-C$_4$haloalkyl, C$_1$-C$_6$alkylsulfanyl, C$_1$-C$_6$alkylsulfinyl, or C$_1$-C$_6$alkylsulfonyl; or is C$_3$-C$_6$cycloalkyl which can be mono- or polysubstituted by substituents selected from the group consisting of halogen, C$_1$-C$_4$alkyl, C$_1$-C$_4$haloalkyl and cyano; or $R_3$ is phenyl which can be mono- or polysubstituted by substituents selected from the group consisting of halogen, cyano, nitro, C$_2$-C$_6$alkenyl, C$_2$-C$_6$haloalkenyl, C$_2$-C$_6$alkynyl, C$_2$-C$_6$haloalkynyl, C$_1$-C$_4$alkoxy C$_1$-C$_4$alkyl, C$_1$-C$_4$alkyl, C$_1$-C$_4$haloalkyl, C$_1$-C$_4$haloalkoxy, C$_1$-C$_4$alkoxy, C$_1$-C$_4$haloalkylsulfanyl, C$_1$-C$_4$haloalkylsulfinyl, C$_1$-C$_4$haloalkylsulfonyl, C$_1$-C$_4$alkylsulfanyl, C$_1$-C$_4$alkylsulfinyl, C$_1$-C$_4$alkylsulfonyl and —C(O)C$_1$-C$_4$haloalkyl; or $R_3$ is pyrimidinyl or pyridinyl linked via a carbon atom to the ring which contains the substituent A, said pyrimidinyl or pyridinyl can be mono- or polysubstituted by substituents selected from the group consisting of halogen, cyano, nitro, C$_2$-C$_6$alkenyl, C$_2$-C$_6$haloalkenyl, C$_2$-C$_6$alkynyl, C$_2$-C$_6$haloalkynyl, C$_1$-C$_4$alkoxy C$_1$-C$_4$alkyl, C$_1$-C$_4$alkyl, C$_1$-C$_4$haloalkyl, C$_1$-C$_4$haloalkoxy, C$_1$-C$_4$alkoxy, C$_1$-C$_4$haloalkylsulfanyl, C$_1$-C$_4$haloalkylsulfinyl, C$_1$-C$_4$haloalkylsulfonyl, C$_1$-C$_4$alkylsulfanyl, C$_1$-C$_4$alkylsulfinyl, C$_1$-C$_4$alkylsulfonyl and —C(O)C$_1$-C$_4$haloalkyl; or $R_3$ is a pyrazolyl—or a triazolyl ring system linked via a nitrogen atom to the ring which contains the substituent G$_3$, said ring system can be mono- or polysubstituted by substituents selected from the group consisting of halogen, cyano, nitro, C$_2$-C$_6$alkenyl, C$_2$-C$_6$haloalkenyl, C$_2$-C$_6$alkynyl, C$_2$-C$_6$haloalkynyl, C$_1$-C$_4$alkoxy C$_1$-C$_4$alkyl, C$_1$-C$_4$alkyl, C$_1$-C$_4$haloalkyl, C$_1$-C$_4$haloalkoxy, C$_1$-C$_4$alkoxy, C$_1$-C$_4$alkylsulfanyl, C$_1$-C$_4$alkylsulfinyl, C$_1$-C$_4$alkylsulfonyl, —C(O)C$_1$-C$_4$alkyl, C$_1$-C$_4$haloalkylsulfanyl, C$_1$-C$_4$haloalkylsulfinyl, C$_1$-C$_4$haloalkylsulfonyl and —C(O)C$_1$-C$_4$haloalkyl; and said ring system contains 1, 2 or 3 heteroatoms selected from the group consisting of nitrogen, oxygen and sulphur, where said ring system may not contain more than one oxygen atom and not more than one sulfur atom;

$R_4$ is hydrogen, halogen, cyano or C$_1$-C$_4$haloalkyl; and $R_5$ is C$_1$-C$_4$alkyl.

Further preferred are compounds of formula I-1, wherein $R_1$ is C$_1$-C$_4$alkyl;

$R_2$ is C$_1$-C$_6$haloalkyl, C$_1$-C$_4$haloalkylsulfanyl, C$_1$-C$_4$haloalkylsulfinyl, C$_1$-C$_4$haloalkylsulfonyl;

R$_3$ is hydrogen, halogen, cyano, C$_1$-C$_6$haloalkyl, C$_3$-C$_6$cycloalkyl, C$_1$-C$_6$haloalkylsulfanyl, C$_1$-C$_6$haloalkylsulfinyl, C$_1$-C$_6$haloalkylsulfonyl; or is C$_3$-C$_6$cycloalkyl which can be mono- or polysubstituted by substituents selected from the group consisting of halogen, C$_1$-C$_4$alkyl, C$_1$-C$_4$haloalkyl and cyano; or R$_3$ is phenyl which can be mono- or polysubstituted by substituents selected from the group consisting of halogen, cyano, C$_1$-C$_4$haloalkyl, C$_1$-C$_4$haloalkylsulfanyl, C$_1$-C$_4$haloalkylsulfinyl, C$_1$-C$_4$haloalkylsulfonyl, C$_1$-C$_4$alkylsulfanyl, C$_1$-C$_4$alkylsulfinyl and C$_1$-C$_4$alkylsulfonyl; or R$_3$ is pyrimidinyl or pyridinyl which both can be mono- or polysubstituted by substituents selected from the group consisting of halogen, cyano, C$_1$-C$_4$haloalkyl, C$_1$-C$_4$haloalkylsulfanyl, C$_1$-C$_4$haloalkylsulfinyl, C$_1$-C$_4$haloalkylsulfonyl, C$_1$-C$_4$alkylsulfanyl, C$_1$-C$_4$alkylsulfinyl and C$_1$-C$_4$alkylsulfonyl; or R$_3$ is a pyrazolyl- or a triazolyl ring system linked via a nitrogen atom to the ring which contains the substituent G$_3$, said ring system can be mono- or polysubstituted by substituents selected from the group consisting of halogen, cyano, C$_1$-C$_4$haloalkyl, C$_1$-C$_4$haloalkylsulfanyl, C$_1$-C$_4$haloalkylsulfinyl, C$_1$-C$_4$haloalkylsulfonyl, C$_1$-C$_4$alkylsulfanyl, C$_1$-C$_4$alkylsulfinyl and C$_1$-C$_4$alkylsulfonyl; and said ring system contains 1, 2 or 3 heteroatoms selected from the group consisting of nitrogen, oxygen and sulphur, where said ring system may not contain more than one oxygen atom and not more than one sulfur atom;

R$_4$ is hydrogen, halogen, cyano or C$_1$-C$_4$haloalkyl; and
R$_5$ is C$_1$-C$_4$alkyl.

Further preferred are compounds of formula I, wherein
R$_1$ is ethyl or methyl;
R$_2$ is C$_1$-C$_6$haloalkyl;
R$_3$ is hydrogen, halogen, C$_1$-C$_6$haloalkyl, C$_3$-C$_6$cycloalkyl, C$_1$-C$_6$haloalkylsulfanyl, C$_1$-C$_6$haloalkylsulfinyl or C$_1$-C$_6$haloalkylsulfonyl; or R$_3$ is phenyl which can be mono- or polysubstituted by substituents selected from the group consisting of halogen, cyano, C$_1$-C$_4$haloalkyl, C$_1$-C$_4$haloalkylsulfanyl, C$_1$-C$_4$haloalkylsulfinyl, C$_1$-C$_4$haloalkylsulfonyl, C$_1$-C$_4$alkylsulfanyl, C$_1$-C$_4$alkylsulfinyl and C$_1$-C$_4$alkylsulfonyl; or R$_3$ is pyrimidinyl or pyridinyl which both can be mono- or polysubstituted by substituents selected from the group consisting of halogen, cyano, C$_1$-C$_4$haloalkyl, C$_1$-C$_4$haloalkylsulfanyl, C$_1$-C$_4$haloalkylsulfinyl, C$_1$-C$_4$haloalkylsulfonyl, C$_1$-C$_4$alkylsulfanyl, C$_1$-C$_4$alkylsulfinyl and C$_1$-C$_4$alkylsulfonyl; or R$_3$ is a pyrazolyl- or a triazolyl ring system linked via a nitrogen atom to the ring which contains the substituent G$_3$, said ring system can be mono- or polysubstituted by substituents selected from the group consisting of halogen, cyano, C$_1$-C$_4$haloalkyl, C$_1$-C$_4$haloalkylsulfanyl, C$_1$-C$_4$haloalkylsulfinyl, C$_1$-C$_4$haloalkylsulfonyl, C$_1$-C$_4$alkylsulfanyl, C$_1$-C$_4$alkylsulfinyl and C$_1$-C$_4$alkylsulfonyl; and said ring system contains 1, 2 or 3 heteroatoms selected from the group consisting of nitrogen, oxygen and sulphur, where said ring system may not contain more than one oxygen atom and not more than one sulfur atom;

R$_4$ is hydrogen; and
R$_5$ is C$_1$-C$_4$alkyl.

Further preferred are compounds of formula I, wherein
R$_1$ is ethyl or methyl;
R$_2$ is CF$_3$;
R$_3$ is hydrogen, halogen, C$_1$-C$_2$haloalkyl, cyclopropane, trifluoromethylsulfanyl, trifluoromethylsulfinyl or trifluoromethylsulfonyl; or R$_3$ is phenyl which can be mono- or polysubstituted by substituents selected from the group consisting of halogen, cyano, C$_1$-C$_2$haloalkyl, trifluoromethylsulfanyl, trifluoromethylsulfinyl, trifluoromethylsulfonyl and C$_1$-C$_2$alkylsulfanyl; or R$_3$ is pyrimidinyl or pyridinyl which both can be mono- or polysubstituted by substituents selected from the group consisting of halogen, cyano, C$_1$-C$_2$haloalkyl, trifluoromethylsulfanyl, trifluoromethylsulfinyl, trifluoromethylsulfonyl and C$_1$-C$_2$alkylsulfanyl; or R$_3$ is a pyrazolyl- or a triazolyl ring system linked via a nitrogen atom to the ring which contains the substituent G$_3$, said ring system can be mono- or polysubstituted by substituents selected from the group consisting of halogen, cyano, C$_1$-C$_2$haloalkyl, trifluoromethylsulfanyl, trifluoromethylsulfinyl, trifluoromethylsulfonyl and C$_1$-C$_2$alkylsulfanyl; and said ring system contains 1, 2 or 3 heteroatoms selected from the group consisting of nitrogen, oxygen and sulphur, where said ring system may not contain more than one oxygen atom and not more than one sulfur atom;

R$_4$ is hydrogen; and
R$_5$ is C$_1$-C$_4$alkyl.

Further preferred are compounds of formula I, wherein
R$_1$ is ethyl;
R$_2$ is CF$_3$;
R$_3$ is hydrogen, halogen, trifluoromethyl, pentafluoroethyl, cyclopropane, trifluoromethylsulfanyl, trifluoromethylsulfinyl or trifluoromethylsulfonyl; or R$_3$ is phenyl which can be mono- or polysubstituted by substituents selected from the group consisting of halogen, cyano, trifluoromethyl, trifluoromethylsulfanyl, trifluoromethylsulfinyl, trifluoromethylsulfonyl, and methylsulfanyl; or R$_3$ is pyrimidinyl or pyridinyl which both can be mono- or polysubstituted by substituents selected from the group consisting of halogen, cyano, trifluoromethyl, trifluoromethylsulfanyl, trifluoromethylsulfinyl, trifluoromethylsulfonyl and methylsulfanyl; or R$_3$ is a pyrazolyl- or a triazolyl ring system linked via a nitrogen atom to the ring which contains the substituent G$_3$, said ring system can be mono- or polysubstituted by substituents selected from the group consisting of halogen, cyano, trifluoromethyl, trifluoromethylsulfanyl, trifluoromethylsulfinyl, trifluoromethylsulfonyl and methylsulfanyl; and said ring system contains 1, 2 or 3 heteroatoms selected from the group consisting of nitrogen, oxygen and sulphur, where said ring system may not contain more than one oxygen atom and not more than one sulfur atom;

R$_4$ is hydrogen; and
R$_5$ is methyl.

Further preferred compounds of formula I are those, wherein
A is CH or N;
X is S, SO or SO$_2$;
R$_1$ is C$_1$-C$_4$alkyl;
R$_2$ is CF$_3$;
R$_3$ is hydrogen, halogen or C$_1$-C$_4$haloalkyl; or
R$_3$ is cyclopropane which can be mono-substituted by cyano; or
R$_3$ is phenyl which can be mono- or polysubstituted by substituents selected from the group consisting of halogen, cyano, C$_1$-C$_2$haloalkyl, C$_1$-C$_2$halomethoxy, C$_1$-C$_2$alkoxy and C$_1$-C$_2$sulfanyl; or R$_3$ is pyrimidinyl or pyridinyl linked via a carbon atom to the ring which contains the substituent A, said pyrimidinyl or pyridinyl can be mono- or polysubstituted by substituents selected from the group consisting of halogen, cyano, C$_1$-C$_2$haloalkyl, C$_1$-C$_2$alkoxy; or R$_3$ is a pyrazolyl- or a triazolyl ring system linked via a nitrogen atom to the ring, said ring system can be mono- or polysubstituted by substituents selected from the group consisting of halogen, cyano and C$_1$-C$_2$haloalkyl;

R$_4$ is hydrogen; and

R$_5$ is methyl.

Especially preferred compounds of formula I are those, wherein

A is N;

X is S or SO$_2$;

R$_1$ is C$_1$-C$_4$alkyl, preferably ethyl;

R$_2$ is C$_1$-C$_4$haloalkyl, preferably trifluoromethl;

R$_3$ is phenyl, which is mono- or disubstituted by halogen, preferably is phenyl which is mono-substituted by fluoro;

R$_4$ is hydrogen;

R$_5$ is C$_1$-C$_4$alkyl, preferably methyl.

The process according to the invention for preparing compounds of formula (I) is carried out by methods known to those skilled in the art, or described for example in WO 2009/131237, WO 2011/043404, WO 2011/040629, WO 2010/125985, WO 2012/086848, WO 2013/018928, WO 2013/191113, WO 2013/180193 and WO 2013/180194, and involves reaction of a compound of formula II,

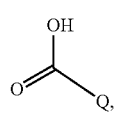

(II)

wherein Q is the group

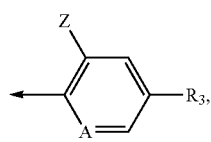

(Q)

wherein Z is X—R$_1$ or a leaving group, for example a halogen, and wherein X, R$_1$, R$_3$ and A are as described under formula I above, and wherein the arrow in the radical Q shows the point of attachment to the carbon atom of the carboxyl group in the compound of formula II, with a compound of formula III,

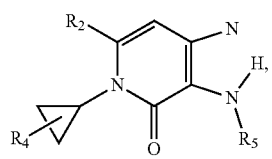

(III)

wherein R$_2$, R$_4$ and R$_5$ are as described under formula I above, in the presence of a de-hydrating agent, such as for example polyphosphoric acid at temperature between 150° C. to 250° C., to yield compounds of formula Ia, wherein the substituents are as described above and under formula I. Such processes are well known and have been described for example in WO 2008/128968 or WO 2006/003440. The process is summarized in scheme 1 for compounds of formula Ia:

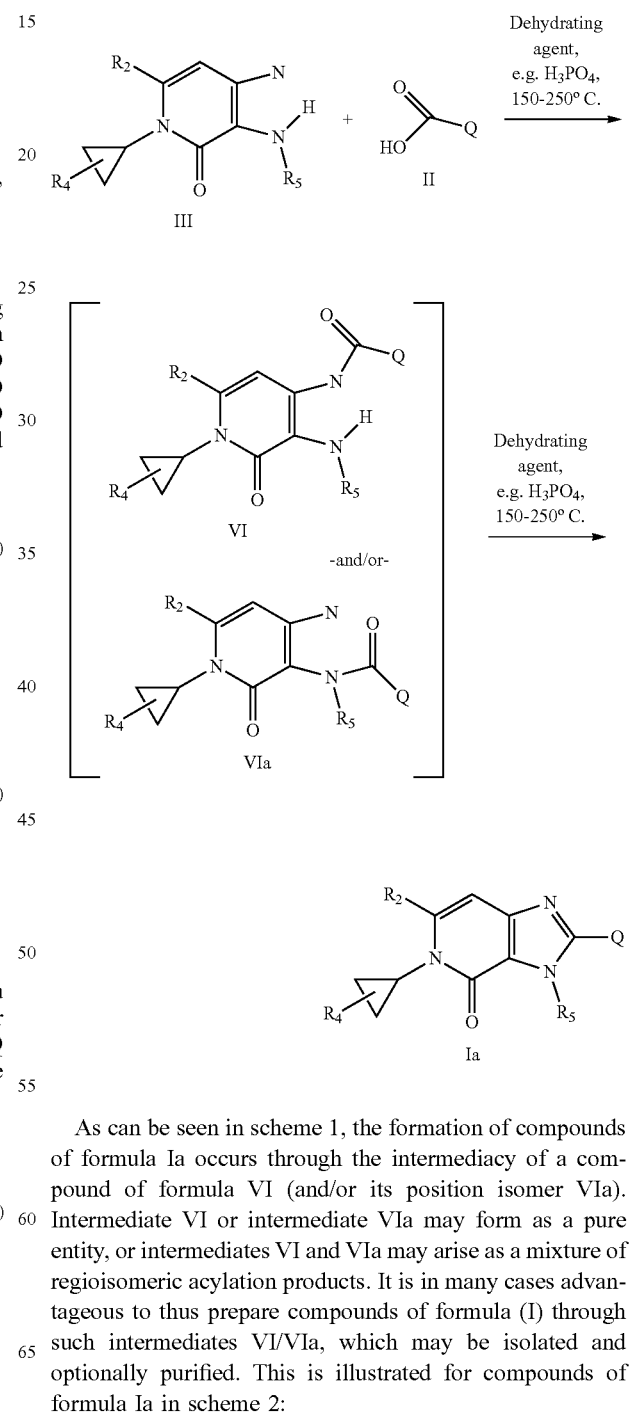

Scheme 1

As can be seen in scheme 1, the formation of compounds of formula Ia occurs through the intermediacy of a compound of formula VI (and/or its position isomer VIa). Intermediate VI or intermediate VIa may form as a pure entity, or intermediates VI and VIa may arise as a mixture of regioisomeric acylation products. It is in many cases advantageous to thus prepare compounds of formula (I) through such intermediates VI/VIa, which may be isolated and optionally purified. This is illustrated for compounds of formula Ia in scheme 2:

Scheme 2

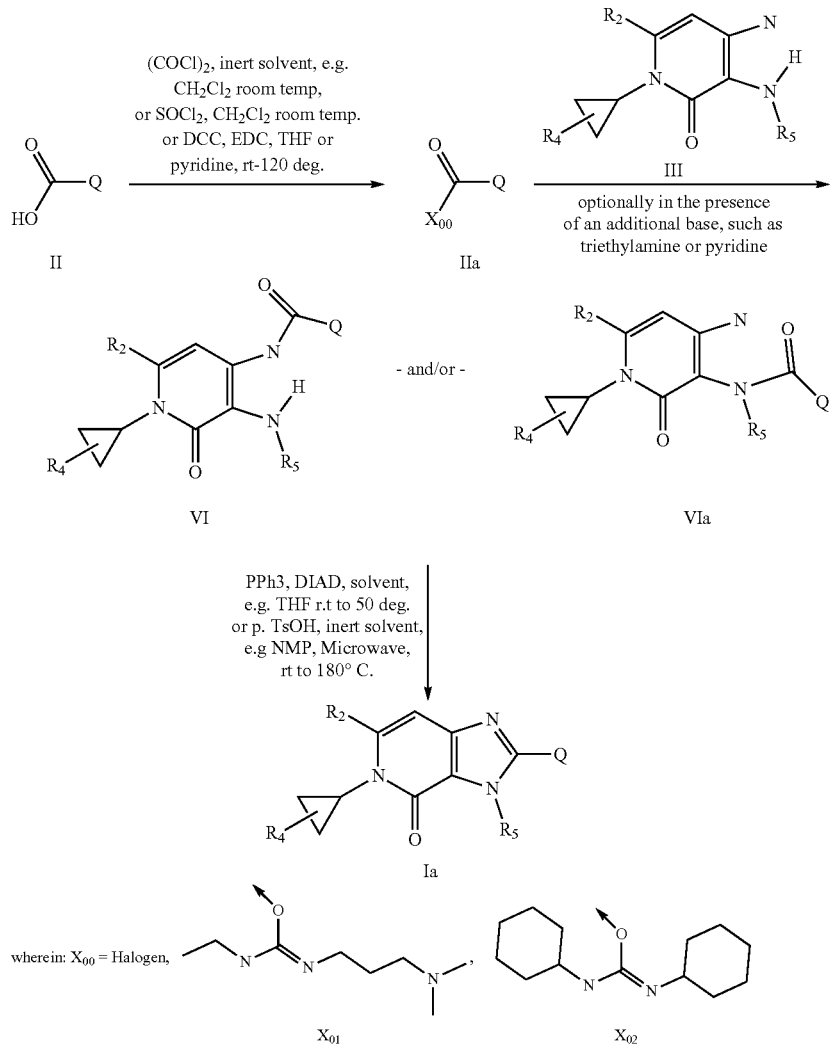

Compounds of the formula VI and/or VIa (or a mixture thereof), or a salt thereof, wherein Q is as defined above, and wherein $R_2$, $R_4$ and $R_5$ are as described under formula I above, may be prepared by i) activation of compound of formula II, wherein Q is as defined above, by methods known to those skilled in the art and described in, for example, Tetrahedron, 2005, 61 (46), 10827-10852, to form an activated species IIa, wherein Q is as defined above and wherein $X_{00}$ is halogen, preferably chlorine. For example, compounds IIa where $X_{00}$ is halogen, preferably chlorine, are formed by treatment of II with, for example, oxallyl chloride $(COCl)_2$ or thionyl chloride $SOCl_2$ in the presence of catalytic quantities of N,N-dimethylformamide DMF in inert solvents such as methylene chloride $CH_2Cl_2$ or tetrahydrofuran THF at temperatures between 20 to 100° C., preferably 25° C. Alternatively, treatment of compounds of formula II with, for example, 1-ethyl-3-(3-dimethylaminopropyl)carbodiimide EDC or dicyclohexyl carbodiimide DCC will generate an activated species IIa, wherein $X_{00}$ is $X_{01}$ or $X_{02}$ respectively, in an inert solvent, such as pyridine or tetrahydrofuran THF, optionally in the presence of a base, such as triethylamine, at temperatures between 25-180° C.; followed by ii) treatment of the activated species IIa with a compound of formula III (or a salt thereof), wherein $R_8$, $R_2$, $R_4$ and $R_5$ are as described under formula I above, optionally in the presence of a base, such as triethylamine or pyridine, in an inert solvents such as dichloromethane, tetrahydrofuran, dioxane or toluene, at temperatures between 0 and 80° C., to form the compounds of formula VI and/or VIa (or a mixture thereof).

Compounds of formula VI and/or VIa (or a mixture thereof) may further be converted into compounds of formula Ia, wherein Q is as defined above, and wherein $R_2$, $R_4$ and $R_5$ are as described under formula I above, by dehydration, eg. by heating the compounds VI and/or VIa (or a mixture thereof) in the presence of an acid catalyst, such as for example methane sulfonic acid, or para-toluene sulfonic acid TsOH, in an inert solvent such as N-methyl pyrrolidine NMP at temperatures between 25-180° C., preferably 100-170° C., optionally under microwave conditions. Such processes have been described previously, for example, in WO 2010/125985.

Compounds of formula Ia, wherein Q is as defined above, and wherein Z is a leaving group, for example halogen, preferably fluorine or chlorine, and wherein $R_2$, $R_4$ and $R_5$ are as described under formula I above, can be reacted with compounds of formula V

$$R_1\text{—SH} \qquad (V),$$

or a salt thereof, wherein $R_1$ is as defined in formula I, optionally in the presence of a suitable base, such as alkali metal carbonates, for example sodium carbonate and potassium carbonate, or alkali metal hydrides such as sodium hydride, or alkali metal hydroxides such as sodium hydroxide and potassium hydroxide, in an inert solvent at temperatures preferably between 25-120° C., to generate compounds of formula Ib, wherein $R_1$ is as described under formula I above, and in which A, $R_2$, $R_3$, $R_4$ and $R_5$ are as described under formula I above. Examples of solvent to be used include ethers such as THF, ethylene glycol dimethyl ether, tert-butylmethyl ether, and 1,4-dioxane, aromatic hydrocarbons such as toluene and xylene, nitriles such as acetonitrile or polar aprotic solvents such as N,N-dimethylformamide, N,N-dimethylacetamide, N-methyl-2-pyrrolidone or dimethyl sulfoxide. Similar chemistry has been previously described, as for example in WO2013/018928. Examples of salts of the compound of formula V include compounds of the formula Va $$R_1\text{—S-M} \qquad (Va),$$

wherein $R_1$ is as defined above and wherein M is, for example, sodium or potassium. This is illustrated for compounds of formula Ib in scheme 3:

Scheme 3

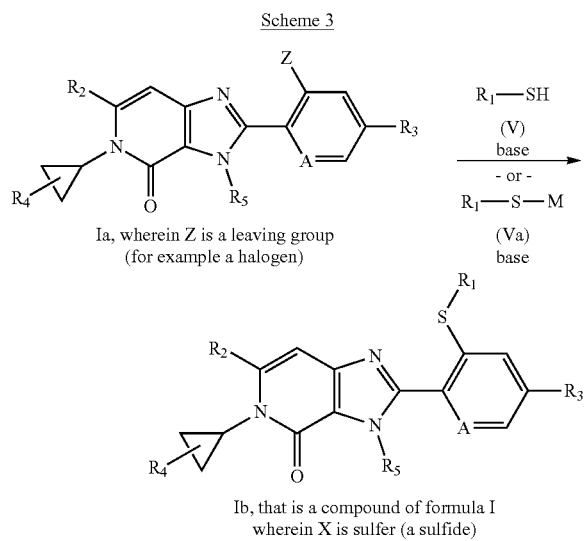

Alternatively, this reaction can be carried out in the presence of a palladium catalyst, such as tris(dibenzylideneacetone)dipalladium(0), in the presence of a phosphor ligand, such as xanthphos, in an inert solvent, for example, xylene at temperatures between 100-160° C., preferably 140° C., as described by Perrio et al. in Tetrahedron 2005, 61, 5253-5259.

The subgroup of compounds of formula I, wherein X is SO (sulfoxide) and/or $SO_2$ (sulfone), may be obtained by means of an oxidation reaction of the corresponding sulfide compounds of formula I, wherein X is S (i.e. a compound of formula Ib above), involving reagents such as, for example, m-chloroperoxybenzoic acid (mCPBA), hydrogen peroxide, oxone, sodium periodate, sodium hypochlorite or tert-butyl hypochlorite amongst other oxidants. The oxidation reaction is generally conducted in the presence of a solvent. Examples of the solvent to be used in the reaction include aliphatic halogenated hydrocarbons such as dichloromethane and chloroform; alcohols such as methanol and ethanol; acetic acid; water; and mixtures thereof. The amount of the oxidant to be used in the reaction is generally 1 to 3 moles, preferably 1 to 1.2 moles, relative to 1 mole of the sulfide compounds Ib to produce the sulfoxide compounds I (wherein X=SO), and preferably 2 to 2.2 moles of oxidant, relative to 1 mole of of the sulfide compounds Ib to produce the sulfone compounds I (wherein X=$SO_2$). Such oxidation reactions are disclosed, for example, in WO 2013/018928.

Compounds of formula Ic, a subgroup of formula Ia above, wherein Z is X—$R_1$ or a leaving group, for example halogen, preferably fluorine or chlorine, and wherein X, $R_1$, $R_2$, $R_4$, $R_5$ and A are as described under formula I above, could be prepared from compounds of formula (VII)

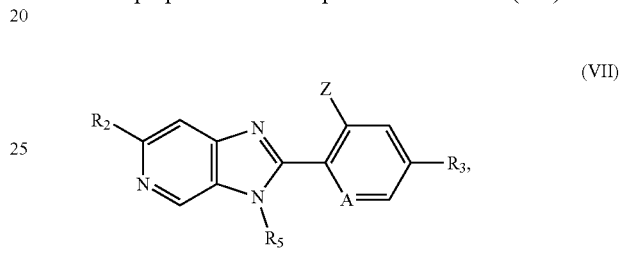

wherein which Z is X—$R_1$ or a leaving group, for example halogen, and wherein X, $R_1$, $R_2$, $R_3$, $R_5$ and A are as described under formula I above, via formation of an N-oxide of formula VIIIa, followed by rearrangement to a compound of formula IXa and alkylation of compound IXa with a reagent of formula $R_4$—$X_{LG}$. This is illustrated for compounds of formula Ic, from compounds of formula VII, in scheme 4:

Scheme 4

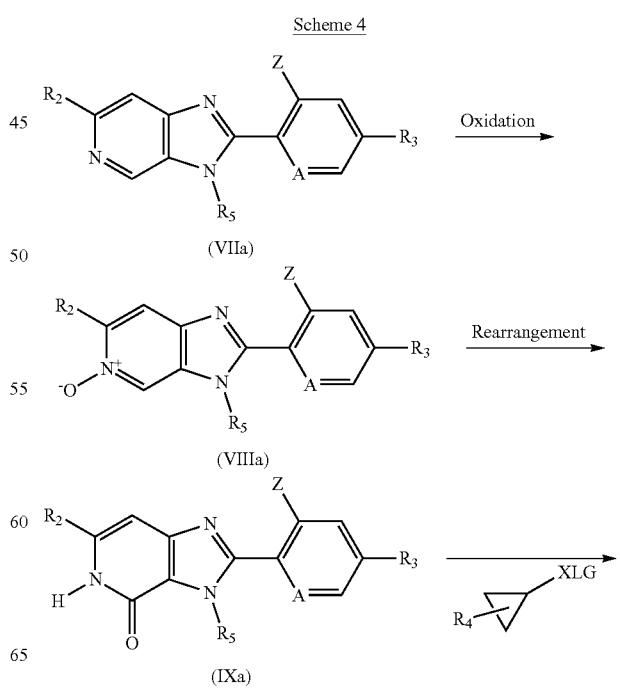

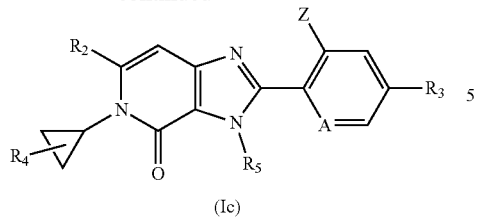

(Ic)

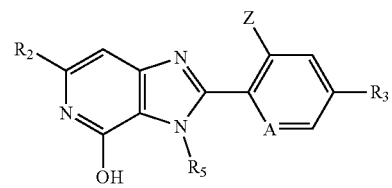

(IXa*)

N-oxide compounds of formula (VIIIa), wherein Z is X—$R_1$ or a leaving group, for example halogen, and wherein X, $R_1$, $R_2$, $R_3$, $R_5$, and A are as described under formula I above, may be prepared from a compound of formula (VIIa), wherein Z is X—$R_1$ or a leaving group, for example halogen, and wherein X, $R_2$, $R_3$, $R_5$, and A are as described under formula I above, via oxidation by reaction with a suitable oxidizing agent, such as meta-perbenzoic acid or hydrogen peroxide in the appropriate inert solvent, such as for example dichloromethane or chloroform. Such oxidations are known from the literature, for example from WO 2013/018928, WO 2010/073128 or Synthetic Communications 2013, 43(8), 1092-1100.

Compounds of formula (IXa) may be prepared from a compound of formula (VIIIa), wherein for both compounds Z is X—$R_1$ or a leaving group, for example halogen, and wherein X, $R_1$, $R_2$, $R_3$, $R_5$, and A are as described under formula I above, via rearrangement, for example mediated by anhydride reagents, such as trifluoroacetic anhydride, in the appropriate solvent, such as N,N-dimethylformamide. Such rearrangement reactions are well known from the literature, for example from Journal of Organic Chemistry 1961, 26, 428-430 or Journal of Heterocyclic Chemistry 1976, 13(6), 1197-2000.

Compounds of formula (IXa), wherein X, $R_1$, $R_2$, $R_3$, $R_5$, and A are as described under formula I above, may exist in a tautomeric form (IXa*), or in a mixture thereof.

Compounds of formula (Ic), wherein Z is X—$R_1$ or a leaving group, for example halogen, and wherein, X, $R_2$, $R_3$, $R_5$, and A are as described under formula I above, and in which $R_4$ is as defined under formula I above, may be prepared from a compound of formula (IXa), wherein Z is X—$R_1$ or a leaving group, for example halogen, and wherein X, $R_1$, $R_2$, $R_3$, $R_5$, and A are as described under formula I above, via reaction with a cyclopropane analogue reagent, wherein $R_4$ is as described in compounds of formula I and $X_{LG}$ is a leaving group, such as halogen or a boron-derived functional group, as for example $B(OH)_2$ or $B(OR_{b1})_2$ wherein $R_{b1}$ can be a $C_1$-$C_4$alkyl group or the two groups $OR_{b1}$ can form together with the boron atom a five membered ring, as for example a pinacol boronic ester. The reaction is commonly performed with one to two equivalents of a base, like potassium phosphate, in presence of a copper catalyst, like for example Copper acetate. The reaction can be run in an inert solvent, like toluene, usually at temperature between 50 to 150° C. and in presence or not of a additional ligand. See for example: Synthetic Communications, 42(9), 1341-1348; 2012.

Compounds of formula VIIa may be made by methods known to a person skilled in the art, see for example WO 2015000715 and they may be prepared by the following way.

Compounds of formula VIIa, wherein Z is X—$R_1$ or a leaving group, for example halogen, and wherein X, $R_2$, $R_3$, $R_5$, and A are as described under formula I above, may be prepared by reaction between compounds of formula II respectively IIa, wherein Z is X—$R_1$ or a leaving group, for example halogen, and wherein X, $R_1$, $R_2$, $R_3$, $R_5$, and A are as described under formula I above, and in which $X_{00}$ is as described above, and compounds of formula IIIa, wherein $R_2$ and $R_5$ are as described under formula I above, under similar conditions as for the preparation of compounds of formula Ia from compounds of formula II/IIa and III described above (see scheme 1 and 2). This is illustrated for compounds of formula VIIa in scheme 6:

Scheme 6

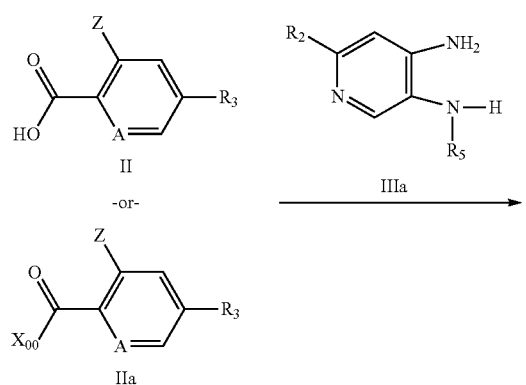

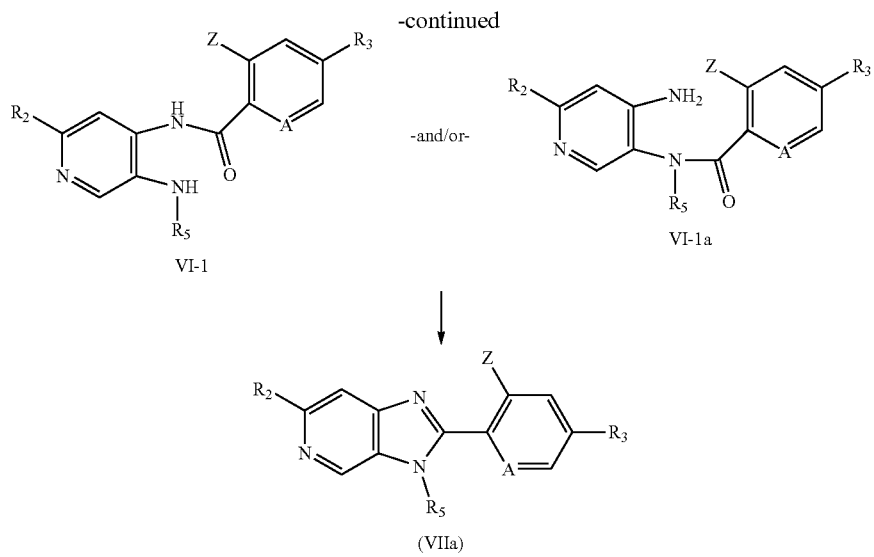

Analogeously to descriptions in schemes 1 and 2, the formation of compounds of formula VIIa occurs through the intermediacy of compounds of formula VI-1 and/or VI-1a (or a mixture thereof), or salts thereof, which optionally may be isolated and purified.

Compounds of the formula IIIa, wherein $R_2$ and $R_5$ are as described under formula I above, may be prepared from diamino compounds of formula X, wherein $R_2$ is as described under formula I above, by means of a direct alkylation with $R_5$-$X_{LG}$, wherein $R_5$ is as described under formula I above and wherein $X_{LG}$ is a leaving group, such as halogen, preferably iodine, bromine or chlorine, in presence of a base, such as sodium carbonate, potassium carbonate or cesium carbonate, or sodium hydride, in a appropriate solvent such as for example N,N-dimethylformamide, N,N-dimethylacetamide or acetonitrile (scheme 7).

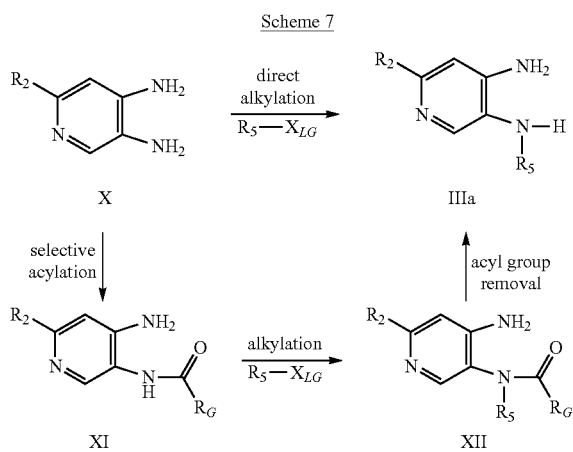

Alternatively, the sequence to prepare compounds of formula IIIa from compounds of formula X, may involve i. a selective acylation of compound X to form a compound of formula XI, wherein $R_2$ is as described under formula I above and wherein the acylation agent is for example di-tert-butyl dicarbonate (leading to compound XI wherein $R_G$ is tert-butyloxy), in an ether solvent, such as for example, tetrahydrofuran or dioxane; ii. alkylation of compound XI with $R_5$-$X_{LG}$, wherein $R_5$ is as described under formula I above and wherein $X_{LG}$ is a leaving group, such as halogen, preferably iodine, bromine or chlorine, in presence of a base, such as sodium carbonate, potassium carbonate or cesium carbonate, or sodium hydride, in a appropriate solvent such as for example N,N-dimethylformamide, N,N-dimethylacetamide or acetonitrile, to generate a compound of formula XII, wherein $R_2$ and $R_5$ are as described under formula I above and wherein $R_G$ is for example tert-butyloxy; and finally iii. deacylation of compound XII to form the compound of formula IIIa, wherein $R_8$, $R_2$ is as described under formula I above. When $R_G$ is for example tert-butyloxy, conditions for the acyl group removal include, for example, treatment of compound XII with hydrogen halide, in particular hydrogen chloride or hydrogen bromide, in solvents such as ethers (for example diethyl ether, tetrahydrofuran or dioxane) or acetic acid. Alternatively, compound XII may also be treated with, for example, trifluoroacetic acid, in optional presence of an inert solvent, such as for example dichloromethane or chloroform, to form a compound of formula IIIa.

This alternative approach to prepare compounds of formula IIIa is described in more details in scheme 8 for the particular situation where $R_2$ is $CF_3$, $R_5$ is $CH_3$, and $R_G$ is tert-butyloxy:

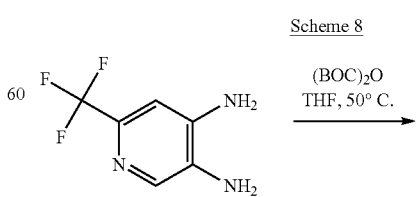

prepared as described in U.S., 7,767,687

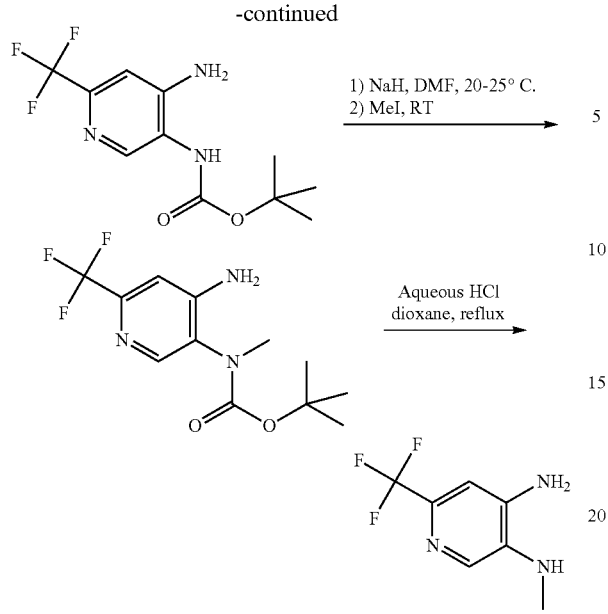

Common abbreviations
(BOC)₂O = di-tert-butyl dicarbonate; THF = tetrahydrofuran;
NaH = sodium hydride; DMF = N,N-dimethylformamide;
MeI = methyl iodide; RT = room temperature; HCl = hydrogen chloride.

Diamino compounds of formula (X) are either known, commercially available or may be made by methods known to a person skilled in the art, for example in analogy to a preparation method described in U.S. Pat. No. 7,767,687.

Alternatively, the sequence to prepare compounds of formula III wherein $R_2$, $R_4$ and $R_5$ are as described under formula I above, from compounds of formula XIII, may involve i. alkylation of compound XIII with $R_5$—$X_{LG}$, wherein $R_5$ is as described under formula I above and wherein $X_{LG}$ is a leaving group, such as halogen, preferably iodine, bromine or chlorine, in presence of a base, such as sodium carbonate, potassium carbonate or cesium carbonate, or sodium hydride, in a appropriate solvent such as for example N,N-dimethylformamide, N,N-dimethylacetamide or acetonitrile, to generate a compound of formula XIV, wherein $R_5$ and $R_2$ are as described under formula I above; ii. a reaction of nitration of compound XIV in classical conditions, for example, see for example, Advanced Organic Chemistry: Reactions, Mechanisms, and Structure, Fourth Edition by Jerry March, 1992 (Publisher Wiley New York, N.Y.) p 523-525; and finally iii. a reaction of reduction of compound XV in classical conditions, for example, see for example, Advanced Organic Chemistry: Reactions, Mechanisms, and Structure, Fourth Edition by Jerry March, 1992 (Publisher Wiley New York, N.Y.) p 1216-1217. See scheme 9.

Scheme 9

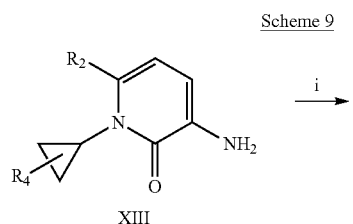

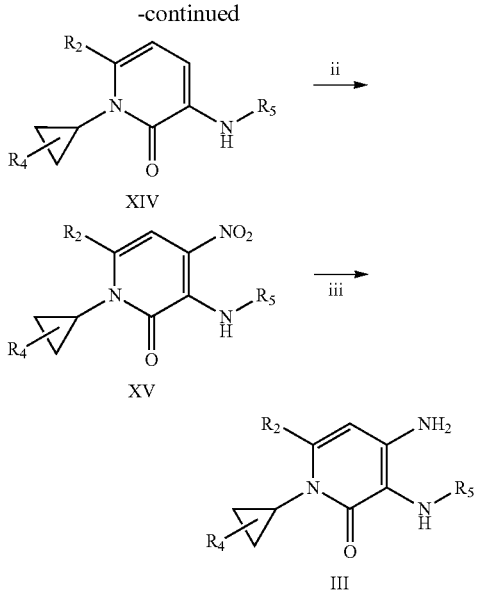

Compounds of formula XIII may be made by methods known to a person skilled in the art. For example via the reaction of compound XIIIa with the appropriate amine (scheme 10). Compounds of formula XIIIa may be made by methods known to a person skilled in the art. See Synthesis 2005, No. 8, pp 1269-1278 and Synthesis 2011, No. 7, pp 1149-1156.

Scheme 10

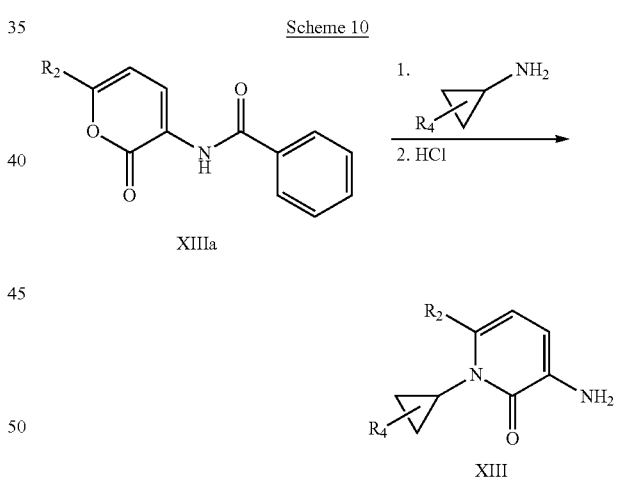

Compounds of formula I-1a, wherein Z is X—$R_1$ or a leaving group, for example halogen, and wherein X, $R_2$, $R_3$, $R_4$, $R_5$, and A are as described under formula I above, may be prepared by reaction between compounds of formula II respectively IIa, wherein Z is X—$R_1$ or a leaving group, for example halogen, and wherein X, $R_1$, $R_2$, $R_4$, $R_3$, $R_5$, and A are as described under formula I above, and in which $X_{00}$ is as described above, and compounds of formula XVI, wherein $R_5$ and $R_2$ are as described under formula I above, under similar conditions as for the preparation of compounds of formula Ia from compounds of formula II/IIa and III described above (see scheme 1 and 2). This is illustrated for compounds of formula XVI in scheme 11:

Scheme 11

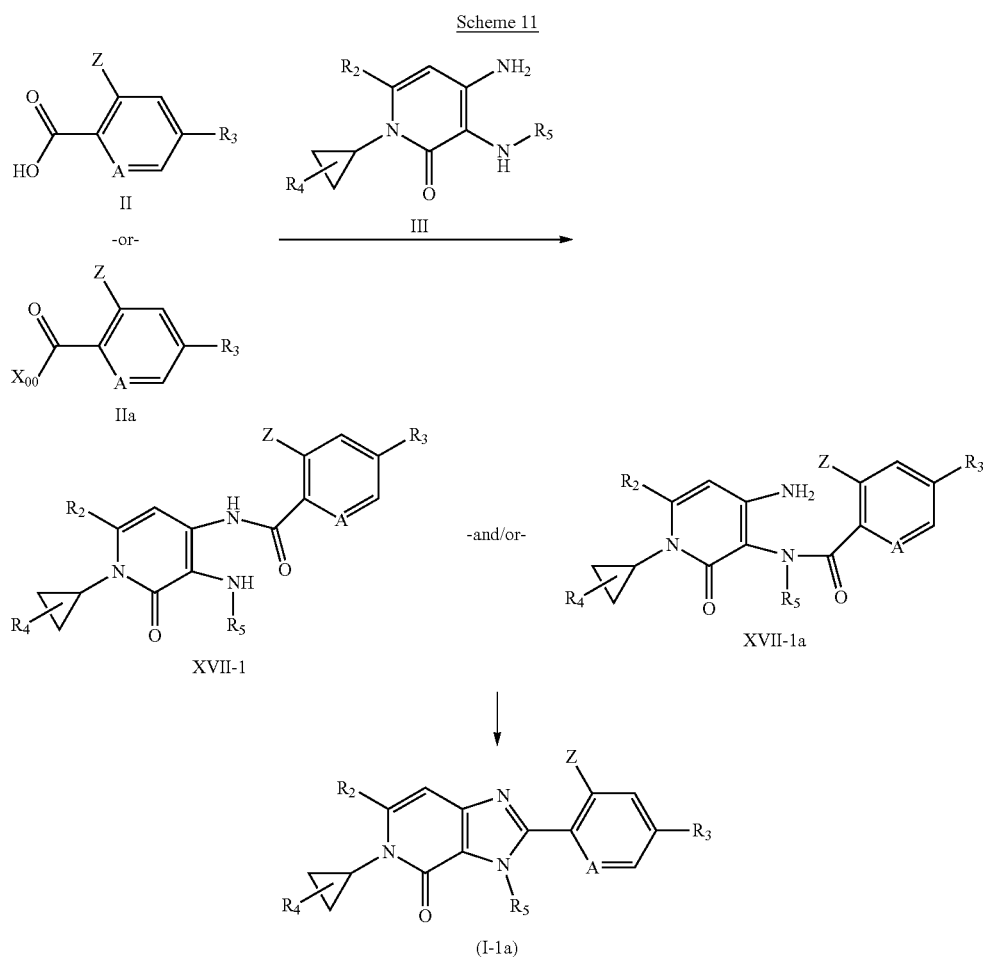

Compounds of formula I can also be made (as depicted in scheme 12) by reacting compounds of formula Id, wherein LG can be a halogen, preferentially chlorine, bromine or iodine, or a sulfonate, like for example a trifluoromethanesulfonate with compounds of formula XVIII, wherein $Y_{b2}$ can be a boron-derived functional group, as for example $B(OH)_2$ or $B(OR_{b2})_2$ wherein $R_{b2}$ can be a $C_1$-$C_6$alkyl group or the two groups $OR_{b2}$ can form together with the boron atom a five- or six-membered ring, as for example a pinacol boronic ester. In formulae Id and XVIII, A, $X_1$, $R_1$, $R_2$, X and $R_3$ are as described in formula I and LG could be including in $R_3$. The reaction can be catalyzed by a palladium based catalyst, for example tetrakis(triphenylphosphine)-palladium(0), bis(triphenyl-phosphine) palladium(II) dichloride or (1,1'bis(diphenylphosphino)-ferrocene)dichloropalladium-dichloromethane (1:1 complex), in presence of a base, like sodium carbonate or cesium fluoride, in a solvent (such as 1,2-dimethoxyethane, tetrahydrofuran or dioxane) or a solvent mixture, like, for example a mixture of 1,2-dimethoxyethane and water, or of dioxane and water, preferably under inert atmosphere. The reaction temperature can preferentially range from room temperature to the boiling point of the reaction mixture, or alternatively heating may be performed under microwave irradiation.

Scheme 12

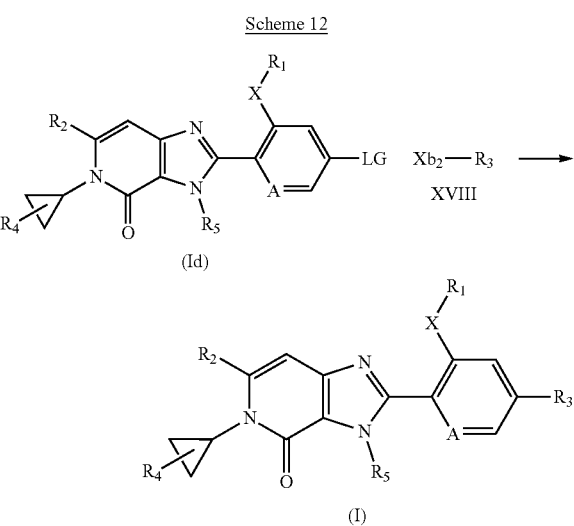

Alternatively, compounds of formula I can be prepared by a Stille reaction of compounds of formula XVIII wherein $Y_{b2}$ is a trialkyl tin derivative, preferably tri-n-butyl tin, with compounds of formula Id. Such Stille reactions are usually carried out in the presence of a palladium catalyst, for example tetrakis(triphenylphosphine)palladium(0), or (1,1'bis(diphenylphosphino)-ferrocene)dichloropalladium-dichloromethane (1:1 complex), in an inert solvent such as DMF, acetonitrile, or dioxane, optionally in the presence of an additive, such as cesium fluoride, or lithium chloride, and optionally in the presence of a further catalyst, for example copper(I)iodide. Such Stille couplings are also well known to those skilled in the art, and have been described in for example *J. Org. Chem.*, 2005, 70, 8601-8604, *J. Org. Chem.*, 2009, 74, 5599-5602, and *Angew. Chem. Int. Ed.*, 2004, 43, 1132-1136.

The compounds of formula XIX

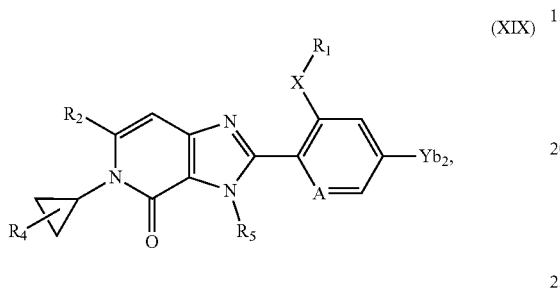

(XIX)

wherein $R_1$, $R_2$, $R_4$, X and A are as defined under formula I above, and $Yb_2$ is —B(OH)$_2$ or —B(OR$_{b2}$)$_2$, in which $R_{b2}$ is a $C_1$-$C_6$alkyl or

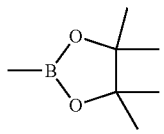

(a 4,4,5,5-tetramethyl-1,3,2-dioxaborolane group), are novel, especially developed for the preparation of the compounds of formula I according to the invention and therefore represent a further object of the invention. The preferred substituent definitions for formula I are also valid for the preferred compounds of formula XIX.

In the particular case where compounds of formula I have the group $R_3$ attached through a nitrogen atom (i.e. those situations where $R_3$ is a nitrogen containing heterocyclic ring system), these compounds can be advantageously accessed by reacting a compound of the formula XIX with a compound of the formula XXa, wherein $Y_{b2}$ can be a boron-derived functional group, such as for example B(OH)$_2$ or B(OR$_{b2}$)$_2$ wherein $R_{b2}$ can be a $C_1$-$C_6$alkyl group or the two groups OR$_{b2}$ can form together with the boron atom a five- or six-membered ring, as for example a pinacol boronic ester (scheme 13a). In formulae XIX and XXa, A, $R_1$, $R_2$, $R_4$ and X are as defined under formula I above and $R_3$ is as described in formula I, with the condition that the attachment point is a nitrogen atom. The reaction, also known as Chan-Lam coupling (P. Y. S. Lam, C. G. Clark, S. Saubern, J. Adams, M. P. Winters, D. M. T. Chan, A. Combs, Tetrahedron Lett. 1998, 39, 2941), is commonly performed with one to two equivalents of a base, like pyridine or triethylamine, in presence of one to two equivalents of a copper derivative, like for example copper (II) acetate and under an oxygen-containing atmosphere. The reaction can be run in an inert solvent, like dichloromethane, dioxane or dimethylformamide, usually at or around room temperature.

Scheme 13a

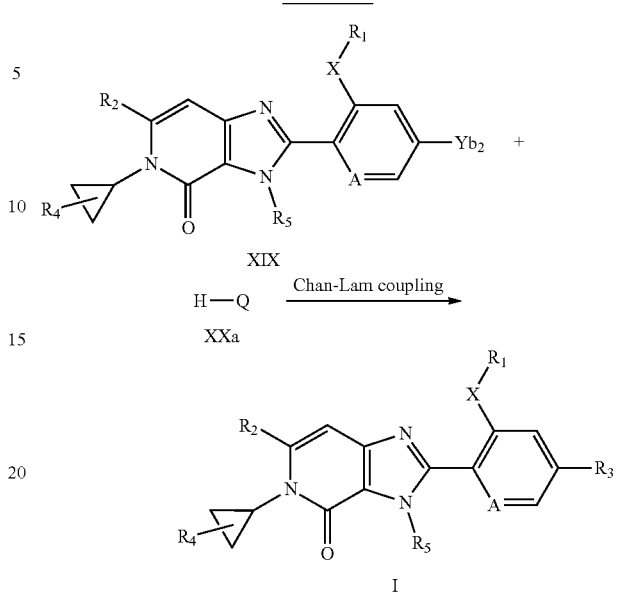

In the particular case where compounds of formula I have the group $R_3$ attached through a nitrogen atom (i.e. those situations where $R_3$ is a nitrogen containing heteroring system), these compounds can be alternatively accessed by reacting a compound of the formula Id with a compound of the formula XXa, wherein LG can be a halogen, preferentially chlorine, bromine or iodine, or a sulfonate, like for example a trifluoromethanesulfonate (scheme 13b). In formulae Id and XXa, A, $R_1$, $R_2$, $R_4$ and X are as defined under formula I above and $R_3$ is as described in formula I, with the condition that the attachment point is a nitrogen atom. Such a reaction with a heterocycle Q-H (which contains an appropriate NH functionality) of formula XXa may be operated in the presence of a base, such as potassium carbonate $K_2CO_3$ or cesium carbonate $Cs_2CO_3$, optionally in the presence of a copper catalyst, for example copper(I) iodide, with or without an additive such as L-proline, N,N'-dimethylcyclohexane-1,2-diamine or N,N'-dimethylethylene-diamine, in an inert solvent such as N-methylpyrrolidone NMP or N,N-dimethylformamide DMF at temperatures between 30-150° C., optionally under microwave irradiation.

Scheme 13b

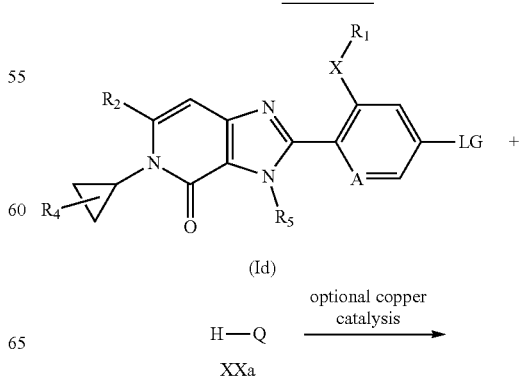

-continued

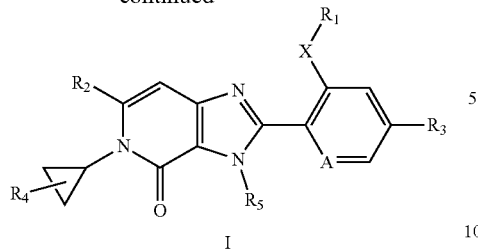

I

Scheme 14

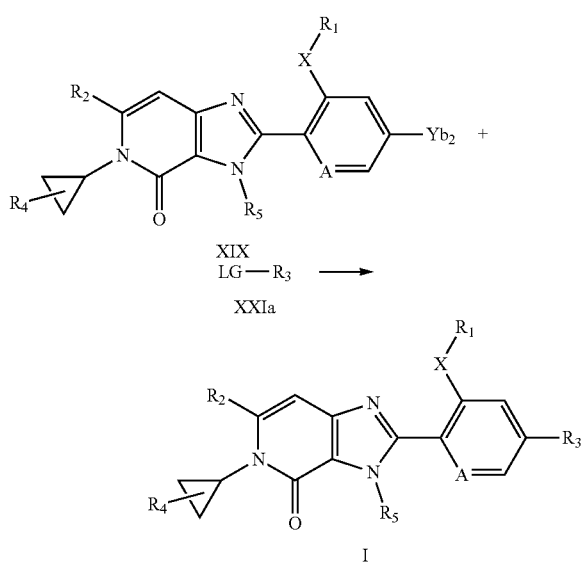

In the particular case where compounds of formula I have the group $R_3$ aromatic, these compounds can be alternatively accessed by reacting a compound of the formula XIX, wherein Yb2 is as described before, with a compound of the formula XXIa, wherein LG can be a halogen, preferentially chlorine, bromine or iodine, or a sulfonate, like for example a trifluoromethanesulfonate (scheme 14). Such reactions may be operated in the presence of a base, such as potassium carbonate $K_2CO_3$ or cesium carbonate $Cs_2CO_3$, optionally in the presence of a palladium catalyst, for example tetrakis(triphenylphosphine)-palladium or (1,1'bis(diphenylphosphino)-ferrocene)dichloropalladium-dichloromethane (1:1 complex), in presence of a base, like sodium carbonate or cesium fluoride, in a solvent or a solvent mixture, like, for example a mixture of 1,2-dimethoxyethane and water, or of dioxane and water, preferably under an inert atmosphere. The reaction temperature can preferentially range from room temperature to the boiling point of the reaction mixture. Such Suzuki reactions are well known to those skilled in the art and have been reviewed, for example *J. Orgmet. Chem.* 576, 1999, 147-168.

Compound of formula XIX may be obtained by Introduction of a pinacolborate functional group via a palladium catalyzed reaction with bispinacol diborane $B_2Pin_2$ on a compound of the formula Id, wherein A, X, $R_1$, $R_2$ and $R_4$ are as described in formula I, and wherein LG is chlorine, bromine, iodine or triflate, is another common strategy. This reaction, generating a cyclic boronate IV, wherein $Yb_2$ is

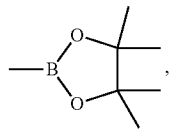

can be performed in an aprotic solvent, in presence of a base, preferentially a weak base, such as potassium acetate KOAc. [1,1'-Bis(diphenylphosphino)ferrocene]dichloropalladium (II), also known as palladium dppf dichloride or Pd(dppf)$Cl_2$, is a common catalyst for this type of reaction. The temperature of the reaction is preferably comprised between 0° C. and the boiling point of the reaction mixture, or alternatively heating may be performed under microwave irradiation.

Scheme 15

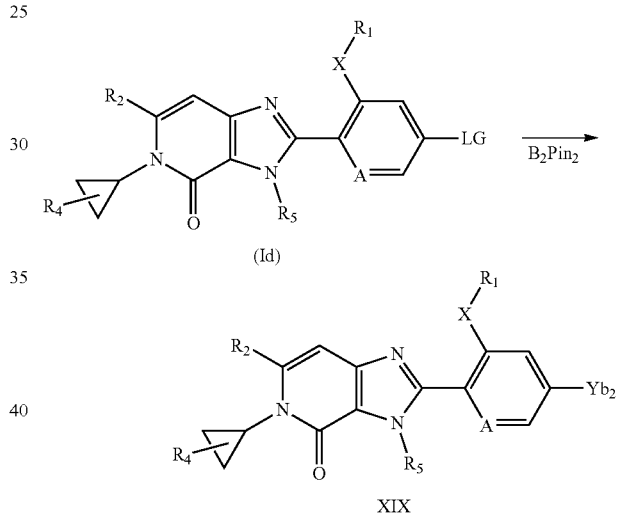

Compounds of formula I, wherein A, $R_1$, $R_2$, $R_3$, X and $R_4$ have the values defined in formula I, and X is —$SO_2$—, can be prepared by oxidation of compounds of formula I or Id, wherein A, $R_1$, $R_2$, $R_3$, X and $R_4$ have the values defined in formula I, and X is —SO—. The reaction can be performed with reagents like, for example, a peracid as peracetic acid or m-chloroperbenzoic acid, or a hydroperoxide, as for example, hydrogen peroxide or tert-butylhydroperoxide, or an inorganic oxidant, like a monoperoxo-disulfate salt or potassium permanganate. In a similar way, compounds of formula I, wherein A, $R_1$, $R_2$, $R_3$, X and $R_4$ have the values defined in formula I, and X is —SO—, can be prepared by oxidation of compounds of formula I, wherein A, $R_1$, $R_2$, $R_3$, X and $R_4$ have the values defined in formula I, and X is —S—, under analogous conditions described above. These reactions can be performed in various organic or aqueous solvents compatible to these conditions, by temperatures from below 0° C. up to the boiling point of the solvent system (scheme 15).

Scheme 15

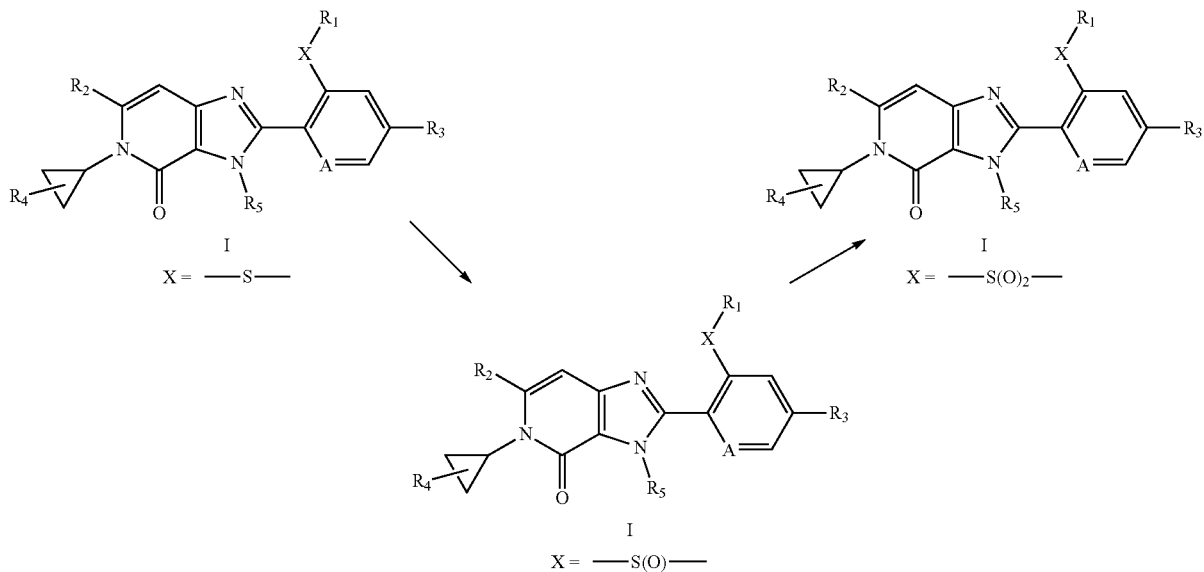

Compounds of formula II,

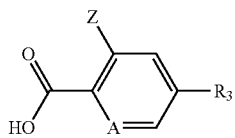

II wherein Z is X—R1 or a leaving group and his obviews analogues such as the ester derivatives, are known, commercialy available or can be made under conditions known to a person skilled in the art.

Compounds of formula I wherein Q is $C_3$-$C_6$cycloalkyl, mono- or polysubstituted by substituents selected from the group consisting of halogen, cyano, $C_1$-$C_4$haloalkyl, and phenyl, may be prepared by methods described above. For the special case of compounds of formula I wherein Q is cycloalkyl substituted by cyano and $C_1$-$C_4$haloalkyl, the compounds can be prepared by the methods shown in Scheme 16.

Scheme 16.
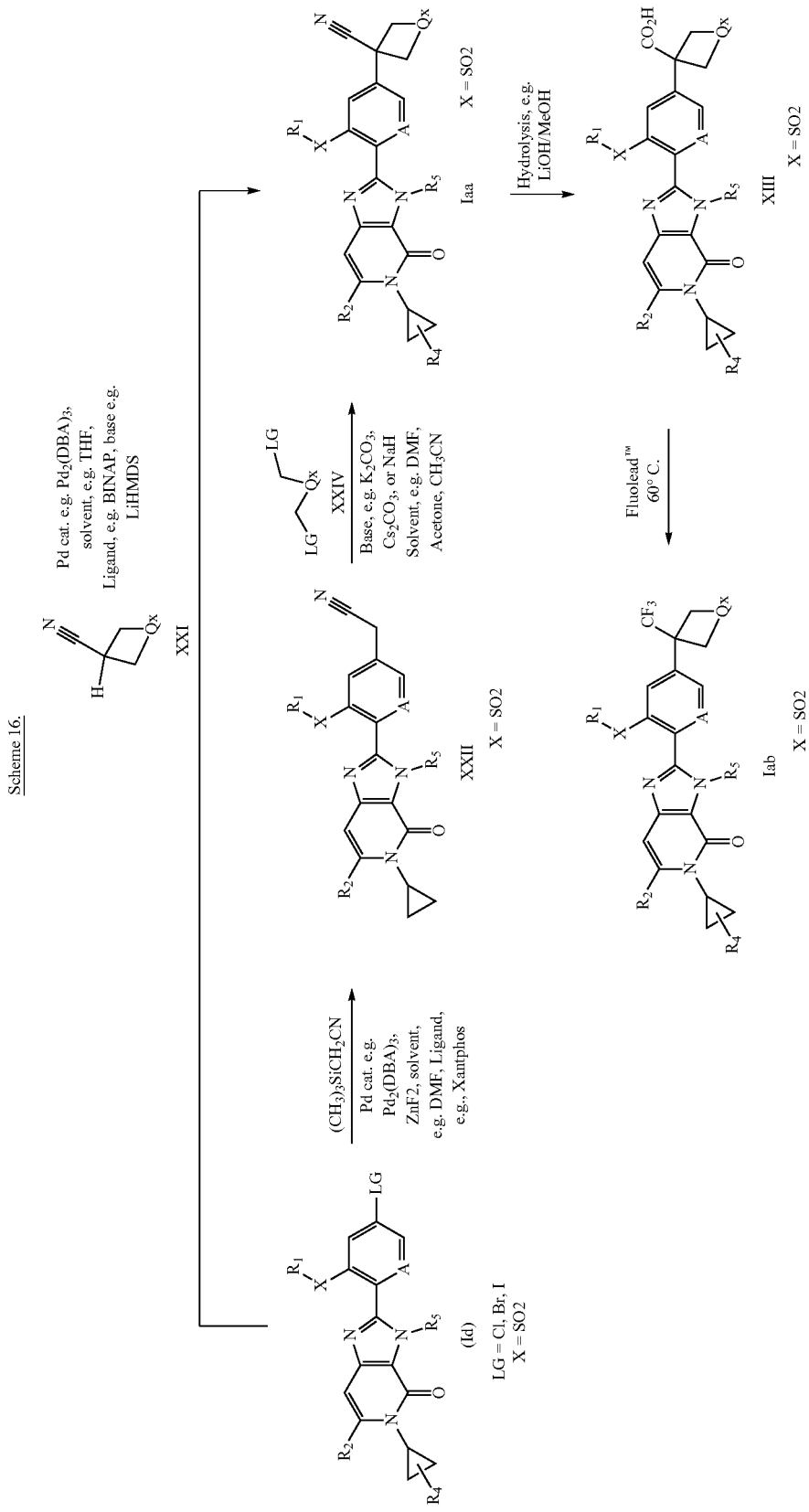

As shown in scheme 16, treatment of compounds of formula Id, where X is SO2, with trimethylsilyl-acetonitrile, in the presence of zinc(II)fluoride, and a palladium(0)catalyst such as Tris(dibenzylideneacetone)dipalladium(0)-chloroform adduct (Pd$_2$(dba)$_3$), a ligand, for example Xantphos, in an inert solvent, such as DMF at temperatures between 100-160° C., optionally under microwave heating, leads to compounds of formula XXII. Such chemistry has been described in the literature, e.g. in *Org. Left.,* 16(24), 6314-6317; 2014. Compounds of formula XXII can be treated with compounds of formula XXIV, wherein Qx is a direct bond or (CH$_2$), and n is 1,2 or 3, in the presence of a base such as sodium hydride, K$_2$CO$_3$, or Cs$_2$CO$_3$, in an inert solvent such as DMF, acetone, or acetonitrile, to give compounds of formula Iaa. Alternatively, compounds of formula Iaa can be prepared directly from compounds of formula Id by treatment with compounds of formula XXI, wherein Qx is is as described in XXIV, with Pd$_2$(dba)$_3$, a ligand, such as BINAP, a strong base such as LiHMDS, in an inert solvent such as THF at temperatures between 40-70° C. Such chemistry has been described in, for example, *J. Am. Chem. Soc.,* 127(45), 15824-15832; 2005. Hydrolysis of compounds of formula Iaa under classical conditions (see for example: Synthetic Organic Methodology: Comprehensive Organic Transformations. A Guide to Functional Group Preparations, Larock, R. C. 1989 p 993) leads to compounds of formula XXII, which coulbe transformed in compounds of formula Iab by fluorination (e.g. see *Org. Lett.,* 16(24), 6314-6317; 2014). Alternatively compounds of formula Iaa can be prepared as shown in schemes 17 and 18.

Scheme 18.

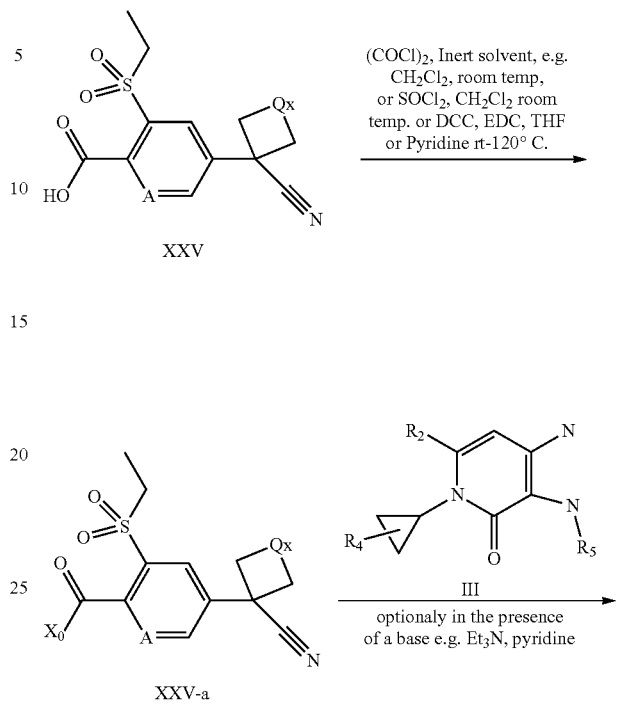

Scheme 17.

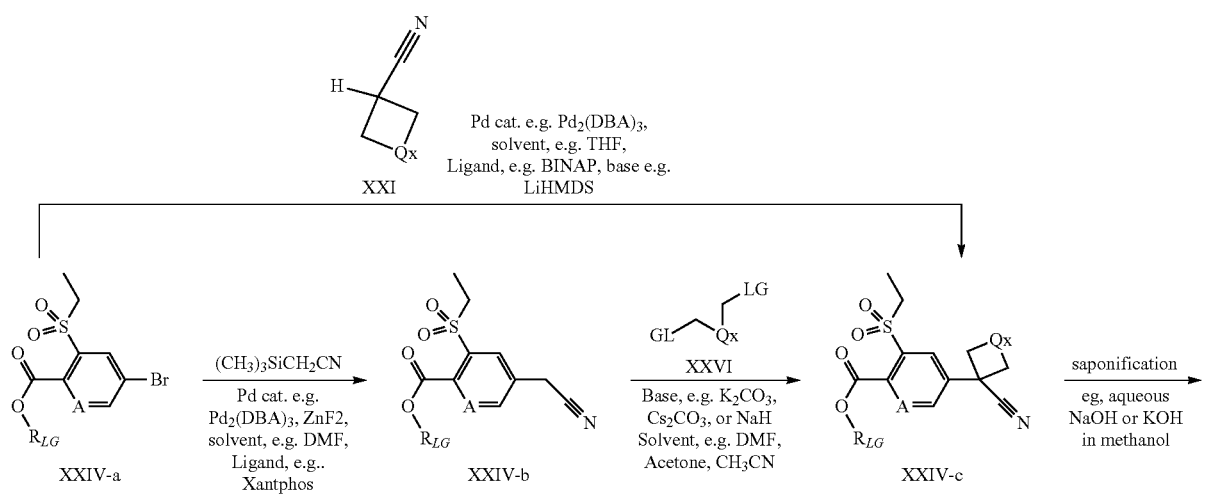

LG = Cl, Br, I

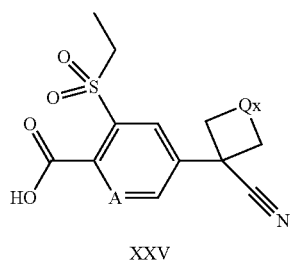

Compounds of formula I, where $R_3$ is substituted C3-cycloalkyl, can be prepared from compounds of formula I wherein $R_3$ is $C_2$-$C_6$alkenyl by the chemsitry illustrated in scheme 19.

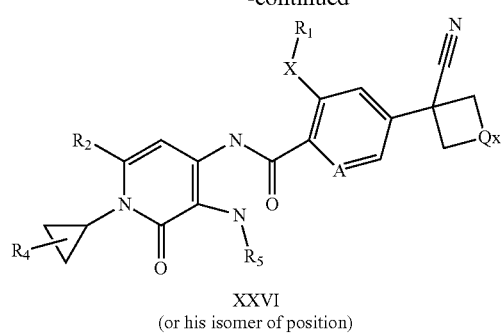

XXVI
(or his isomer of position)

1) PPh$_3$, DIAD, solvent,
e.g. THF, r.t to 50° C.
or p-TsOH, inert solvent,
e.g NMP, Microwave,
rt to 180° C.

Scheme 19

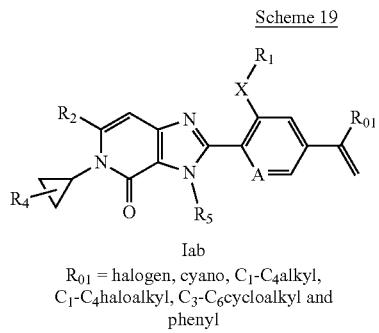

Iab $R_{01}$ = halogen, cyano, $C_1$-$C_4$alkyl,
$C_1$-$C_4$haloalkyl, $C_3$-$C_6$cycloalkyl and phenyl

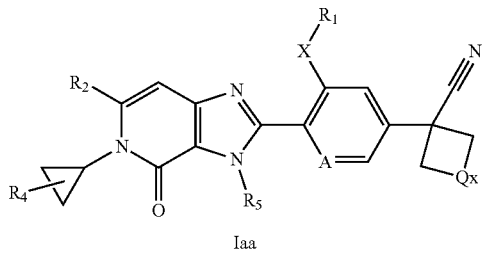

Iaa $X_0$ = Cl, X = SO2

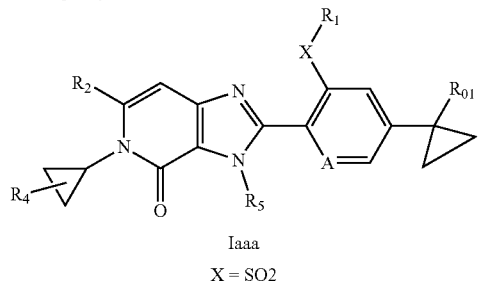

Iaaa
X = SO2

In scheme 19, compounds of formula Iab, wherein $R_1$, $R_2$, $R_4$, X and A are as previously defined, and $R_{01}$ is halogen, cyano, $C_1$-$C_4$alkyl, $C_1$-$C_4$haloalkyl, $C_3$-$C_6$cycloalkyl and phenyl, are treated with diazomethane in the presence a catalyst, such as Pd(OAc)$_2$ or bis(benzonitrile)palladium(II) dichloride, in an inert solvent such as methylene chloride or ether at room temperature or below. Such chemistry has been described in the literature (see for example *Org. Biomol. Chem.* 2, 2471, 2004, WO03/064418, or *Med. Chem. Letts.*, 4, 514-516, 2013.

Compounds of the formula Z-1

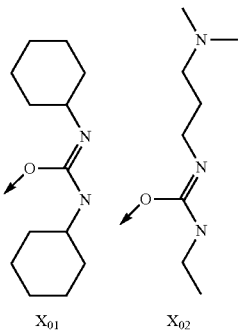

$X_{01}$    $X_{02}$

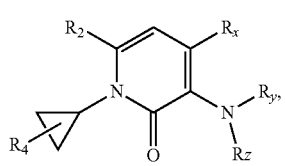

(Z-1)

wherein $R_2$, and $R_4$ are as defined under formula I above;
Rx is NO$_2$ or NH$_2$; Ry is hydrogen and Rz is $C_1$-$C_4$alkyl; are novel and especially prepared for the preparation of the compounds of formula I and therefore constitute a further object of this invention.

The preferred embodiments of the substituents $R_2$ and $R_4$ as described under formula I above are also valid for the compounds of formula Z-1.

As shown in scheme 17, the chemistry used is identical to that described in Scheme 16, it is just that the substrates for the reactions are different. Thus, reaction of the previously described compound XXIV-a with TMS-acetonitrile as described in scheme 16, leads to compounds of formula XXIV-b. These are converted in compounds of formula XXIV-c by reacting with compounds of formula XXVI as described in scheme 16. Similarly, compounds XXIV-c can be prepared directly from XXIV-a by the chemistry discussed in scheme 15. Compounds of formula XXIV-c are readily hydrolysed by methods known to those skilled in the art to give compounds off formula XXV. The chemistry shown in scheme 18 has previously been described in detail in, for example, scheme 11. This chemistry involves forming an activated species III, followed by amide coupling with a compound of formula XXV, to give the intermediate XXVI (or his isomer of position). This intermediate can be cyclised to compounds of formula Iaa by the methods described under, for example, Scheme 11.

For preparing all further compounds of the formula (I) functionalized according to the definitions of III and Q, there are a large number of suitable known standard methods, for example alkylation, halogenation, acylation, amidation, oximation, oxidation and reduction, the choice of the preparation methods which are suitable depending on the properties (reactivity) of the substituents in the intermediates.

The reactants can be reacted in the presence of a base. Examples of suitable bases are alkali metal or alkaline earth metal hydroxides, alkali metal or alkaline earth metal hydrides, alkali metal or alkaline earth metal amides, alkali metal or alkaline earth metal alkoxides, alkali metal or alkaline earth metal acetates, alkali metal or alkaline earth metal carbonates, alkali metal or alkaline earth metal dialkylamides or alkali metal or alkaline earth metal alkylsilylamides, alkylamines, alkylenediamines, free or N-alkylated saturated or unsaturated cycloalkylamines, basic heterocycles, ammonium hydroxides and carbocyclic amines. Examples which may be mentioned are sodium hydroxide, sodium hydride, sodium amide, sodium methoxide, sodium acetate, sodium carbonate, potassium tert-butoxide, potassium hydroxide, potassium carbonate, potassium hydride, lithium diisopropylamide, potassium bis(trimethylsilyl)amide, calcium hydride, triethylamine, diisopropylethylamine, triethylenediamine, cyclohexylamine, N-cyclohexyl-N,N-dimethylamine, N,N-diethylaniline, pyridine, 4-(N,N-dimethylamino)pyridine, quinuclidine, N-methylmorpholine, benzyltrimethylammonium hydroxide and 1,8-diazabicyclo[5.4.0]undec-7-ene (DBU).

The reactants can be reacted with each other as such, i.e. without adding a solvent or diluent. In most cases, however, it is advantageous to add an inert solvent or diluent or a mixture of these. If the reaction is carried out in the presence of a base, bases which are employed in excess, such as triethylamine, pyridine, N-methylmorpholine or N,N-diethylaniline, may also act as solvents or diluents.

The reaction is advantageously carried out in a temperature range from approximately −80° C. to approximately +140° C., preferably from approximately −30° C. to approximately +100° C., in many cases in the range between ambient temperature and approximately +80° C.

A compound of formula I can be converted in a manner known per se into another compound of formula I by replacing one or more substituents of the starting compound of formula I in the customary manner by (an)other substituent(s) according to the invention.

Depending on the choice of the reaction conditions and starting materials which are suitable in each case, it is possible, for example, in one reaction step only to replace one substituent by another substituent according to the invention, or a plurality of substituents can be replaced by other substituents according to the invention in the same reaction step.

Salts of compounds of formula I can be prepared in a manner known per se. Thus, for example, acid addition salts of compounds of formula I are obtained by treatment with a suitable acid or a suitable ion exchanger reagent and salts with bases are obtained by treatment with a suitable base or with a suitable ion exchanger reagent.

Salts of compounds of formula I can be converted in the customary manner into the free compounds I, acid addition salts, for example, by treatment with a suitable basic compound or with a suitable ion exchanger reagent and salts with bases, for example, by treatment with a suitable acid or with a suitable ion exchanger reagent.

Salts of compounds of formula I can be converted in a manner known per se into other salts of compounds of formula I, acid addition salts, for example, into other acid addition salts, for example by treatment of a salt of inorganic acid such as hydrochloride with a suitable metal salt such as a sodium, barium or silver salt, of an acid, for example with silver acetate, in a suitable solvent in which an inorganic salt which forms, for example silver chloride, is insoluble and thus precipitates from the reaction mixture.

Depending on the procedure or the reaction conditions, the compounds of formula I, which have salt-forming properties, can be obtained in free form or in the form of salts.

The compounds of formula I and, where appropriate, the tautomer's thereof, in each case in free form or in salt form, can be present in the form of one of the isomers which are possible or as a mixture of these, for example in the form of pure isomers, such as antipodes and/or diastereomers, or as isomer mixtures, such as enantiomer mixtures, for example racemates, diastereomer mixtures or racemate mixtures, depending on the number, absolute and relative configuration of asymmetric carbon atoms which occur in the molecule and/or depending on the configuration of non-aromatic double bonds which occur in the molecule; the invention relates to the pure isomers and also to all isomer mixtures which are possible and is to be understood in each case in this sense hereinabove and hereinbelow, even when stereochemical details are not mentioned specifically in each case.

Diastereomer mixtures or racemate mixtures of compounds of formula I, in free form or in salt form, which can be obtained depending on which starting materials and procedures have been chosen can be separated in a known manner into the pure diasteromers or racemates on the basis of the physicochemical differences of the components, for example by fractional crystallization, distillation and/or chromatography.

Enantiomer mixtures, such as racemates, which can be obtained in a similar manner can be resolved into the optical antipodes by known methods, for example by recrystallization from an optically active solvent, by chromatography on chiral adsorbents, for example high-performance liquid chromatography (HPLC) on acetyl cellulose, with the aid of suitable microorganisms, by cleavage with specific, immobilized enzymes, via the formation of inclusion compounds, for example using chiral crown ethers, where only one enantiomer is complexed, or by conversion into diastereomeric salts, for example by reacting a basic end-product racemate with an optically active acid, such as a carboxylic acid, for example camphor, tartaric or malic acid, or sulfonic acid, for example camphorsulfonic acid, and separating the diastereomer mixture which can be obtained in this manner, for example by fractional crystallization based on their differing solubilities, to give the diastereomers, from which the desired enantiomer can be set free by the action of suitable agents, for example basic agents.

Pure diastereomers or enantiomers can be obtained according to the invention not only by separating suitable isomer mixtures, but also by generally known methods of diastereoselective or enantioselective synthesis, for example by carrying out the process according to the invention with starting materials of a suitable stereochemistry.

N-oxides can be prepared by reacting a compound of the formula I with a suitable oxidizing agent, for example the $H_2O$/urea adduct in the presence of an acid anhydride, e.g. trifluoroacetic anhydride. Such oxidations are known from the literature, for example from *J. Med. Chem.* 1989, 32, 2561 or WO 2000/15615.

It is advantageous to isolate or synthesize in each case the biologically more effective isomer, for example enantiomer or diastereomer, or isomer mixture, for example enantiomer mixture or diastereomer mixture, if the individual components have a different biological activity.

The compounds of formula I and, where appropriate, the tautomers thereof, in each case in free form or in salt form, can, if appropriate, also be obtained in the form of hydrates and/or include other solvents, for example those which may have been used for the crystallization of compounds which are present in solid form.

The compounds according to the following Tables 1 below can be prepared according to the methods described above. The examples which follow are intended to illustrate the invention and show preferred compounds of formula I. "Ph" represents the phenyl group.

Table 1: This table discloses the 44 compounds of the formula I-1aa:

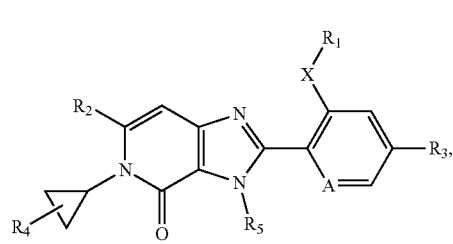
(I-1aa)

TABLE 1

| Comp. No. | X | $R_1$ | $R_3$ | A | $R_2$ | $R_4$ | $R_8$ |
|---|---|---|---|---|---|---|---|
| 1.001 | S | —CH$_2$CH$_3$ | H | N | CF$_3$ | H | CH$_3$ |
| 1.002 | SO$_2$ | —CH$_2$CH$_3$ | H | N | CF$_3$ | H | CH$_3$ |
| 1.003 | S | —CH$_2$CH$_3$ | CF$_3$ | N | CF$_3$ | H | CH$_3$ |
| 1.004 | SO$_2$ | —CH$_2$CH$_3$ | CF$_3$ | N | CF$_3$ | H | CH$_3$ |
| 1.005 | S | —CH$_2$CH$_3$ | 4-Cl—Ph— | N | CF$_3$ | H | CH$_3$ |
| 1.006 | SO$_2$ | —CH$_2$CH$_3$ | 4-Cl—Ph— | N | CF$_3$ | H | CH$_3$ |
| 1.007 | S | —CH$_2$CH$_3$ | 3-CF$_3$—Ph— | N | CF$_3$ | H | CH$_3$ |
| 1.008 | SO$_2$ | —CH$_2$CH$_3$ | 3-CF$_3$—Ph— | N | CF$_3$ | H | CH$_3$ |
| 1.009 | S | —CH$_2$CH$_3$ | 3,5-di-F—Ph— | N | CF$_3$ | H | CH$_3$ |
| 1.010 | SO$_2$ | —CH$_2$CH$_3$ | 3,5-di-F—Ph— | N | CF$_3$ | H | CH$_3$ |
| 1.011 | S | —CH$_2$CH$_3$ | cyclopropyl-CN | N | CF$_3$ | H | CH$_3$ |
| 1.012 | SO$_2$ | —CH$_2$CH$_3$ | cyclopropyl-CN | N | CF$_3$ | H | CH$_3$ |
| 1.013 | S | —CH$_2$CH$_3$ | pyrimidinyl | N | CF$_3$ | H | CH$_3$ |
| 1.014 | SO$_2$ | —CH$_2$CH$_3$ | pyrimidinyl | N | CF$_3$ | H | CH$_3$ |
| 1.015 | S | —CH$_2$CH$_3$ | 5-Cl-pyrimidinyl | N | CF$_3$ | H | CH$_3$ |
| 1.016 | SO$_2$ | —CH$_2$CH$_3$ | 5-Cl-pyrimidinyl | N | CF$_3$ | H | CH$_3$ |
| 1.017 | S | —CH$_2$CH$_3$ | cyclopropyl | N | CF$_3$ | H | CH$_3$ |
| 1.018 | SO$_2$ | —CH$_2$CH$_3$ | cyclopropyl | N | CF$_3$ | H | CH$_3$ |
| 1.019 | S | —CH$_2$CH$_3$ | CF$_3$-pyrazolyl | N | CF$_3$ | H | CH$_3$ |
| 1.020 | SO$_2$ | —CH$_2$CH$_3$ | CF$_3$-pyrazolyl | N | CF$_3$ | H | CH$_3$ |
| 1.021 | S | —CH$_2$CH$_3$ | CF$_3$-pyridinyl | N | CF$_3$ | H | CH$_3$ |
| 1.022 | SO$_2$ | —CH$_2$CH$_3$ | CF$_3$-pyridinyl | N | CF$_3$ | H | CH$_3$ |
| 1.023 | S | —CH$_2$CH$_3$ | H | CH | CF$_3$ | H | CH$_3$ |
| 1.024 | SO$_2$ | —CH$_2$CH$_3$ | H | CH | CF$_3$ | H | CH$_3$ |
| 1.025 | S | —CH$_2$CH$_3$ | CF$_3$ | CH | CF$_3$ | H | CH$_3$ |
| 1.026 | SO$_2$ | —CH$_2$CH$_3$ | CF$_3$ | CH | CF$_3$ | H | CH$_3$ |
| 1.027 | S | —CH$_2$CH$_3$ | 4-Cl—Ph— | CH | CF$_3$ | H | CH$_3$ |
| 1.028 | SO$_2$ | —CH$_2$CH$_3$ | 4-Cl—Ph— | CH | CF$_3$ | H | CH$_3$ |
| 1.029 | S | —CH$_2$CH$_3$ | 3-CF$_3$—Ph— | CH | CF$_3$ | H | CH$_3$ |
| 1.030 | SO$_2$ | —CH$_2$CH$_3$ | 3-CF$_3$—Ph— | CH | CF$_3$ | H | CH$_3$ |
| 1.031 | S | —CH$_2$CH$_3$ | 3,5-di-F—Ph— | CH | CF$_3$ | H | CH$_3$ |
| 1.032 | SO$_2$ | —CH$_2$CH$_3$ | 3,5-di-F—Ph— | CH | CF$_3$ | H | CH$_3$ |
| 1.033 | S | —CH$_2$CH$_3$ | cyclopropyl-CN | CH | CF$_3$ | H | CH$_3$ |
| 1.034 | SO$_2$ | —CH$_2$CH$_3$ | cyclopropyl-CN | CH | CF$_3$ | H | CH$_3$ |
| 1.035 | S | —CH$_2$CH$_3$ | pyrimidinyl | CH | CF$_3$ | H | CH$_3$ |
| 1.036 | SO$_2$ | —CH$_2$CH$_3$ | pyrimidinyl | CH | CF$_3$ | H | CH$_3$ |
| 1.037 | S | —CH$_2$CH$_3$ | 5-Cl-pyrimidinyl | CH | CF$_3$ | H | CH$_3$ |
| 1.038 | SO$_2$ | —CH$_2$CH$_3$ | 5-Cl-pyrimidinyl | CH | CF$_3$ | H | CH$_3$ |
| 1.039 | S | —CH$_2$CH$_3$ | cyclopropyl | CH | CF$_3$ | H | CH$_3$ |
| 1.040 | SO$_2$ | —CH$_2$CH$_3$ | cyclopropyl | CH | CF$_3$ | H | CH$_3$ |
| 1.041 | S | —CH$_2$CH$_3$ | CF$_3$-pyrazolyl | CH | CF$_3$ | H | CH$_3$ |
| 1.042 | SO$_2$ | —CH$_2$CH$_3$ | CF$_3$-pyrazolyl | CH | CF$_3$ | H | CH$_3$ |
| 1.043 | S | —CH$_2$CH$_3$ | CF$_3$-pyridinyl | CH | CF$_3$ | H | CH$_3$ |

TABLE 1-continued

| Comp. No. | X | $R_1$ | $R_3$ | A | $R_2$ | $R_4$ | $R_8$ |
|---|---|---|---|---|---|---|---|
| 1.044 | $SO_2$ | —$CH_2CH_3$ | (pyridyl with CF₃ substituent) | CH | $CF_3$ | H | $CH_3$ | and the N-oxides of the compounds of Table 1.

The compounds of formula I according to the invention are preventively and/or curatively valuable active ingredients in the field of pest control, even at low rates of application, which have a very favorable biocidal spectrum and are well tolerated by warm-blooded species, fish and plants. The active ingredients according to the invention act against all or individual developmental stages of normally sensitive, but also resistant, animal pests, such as insects or representatives of the order Acarina. The insecticidal or acaricidal activity of the active ingredients according to the invention can manifest itself directly, i.e. in destruction of the pests, which takes place either immediately or only after some time has elapsed, for example during ecdysis, or indirectly, for example in a reduced oviposition and/or hatching rate.

Examples of the abovementioned animal pests are:

from the order Acarina, for example,

*Acalitus* spp., *Aculus* spp, *Acaricalus* spp, *Aceria* spp, *Acarus siro*, *Amblyomma* spp., *Argas* spp., *Boophilus* spp., *Brevipalpus* spp., *Bryobia* spp, *Calipitrimerus* spp., *Chorioptes* spp., *Dermanyssus gallinae*, *Dermatophagoides* spp., *Eotetranychus* spp, *Eriophyes* spp., *Hemitarsonemus* spp, *Hyalomma* spp., *Ixodes* spp., *Olygonychus* spp, *Ornithodoros* spp., *Polyphagotarsone latus*, *Panonychus* spp., *Phyllocoptruta oleivora*, *Phytonemus* spp, *Polyphagotarsonemus* spp, *Psoroptes* spp., *Rhipicephalus* spp., *Rhizoglyphus* spp., *Sarcoptes* spp., *Steneotarsonemus* spp, *Tarsonemus* spp. and *Tetranychus* spp.;

from the order Anoplura, for example,

*Haematopinus* spp., *Linognathus* spp., *Pediculus* spp., *Pemphigus* spp. and *Phylloxera* spp.;

from the order Coleoptera, for example,

*Agriotes* spp., *Amphimallon majale*, *Anomala orientalis*, *Anthonomus* spp., *Aphodius* spp, *Astylus atromaculatus*, *Ataenius* spp, *Atomaria linearis*, *Chaetocnema tibialis*, *Cerotoma* spp, *Conoderus* spp, *Cosmopolites* spp., *Cotinis nitida*, *Curculio* spp., *Cyclocephala* spp, *Dermestes* spp., *Diabrotica* spp., *Diloboderus abderus*, *Epilachna* spp., *Eremnus* spp., *Heteronychus arator*, *Hypothenemus hampei*, *Lagria vilosa*, *Leptinotarsa decemLineata*, *Lissorhoptrus* spp., *Liogenys* spp, *Maecolaspis* spp, *Maladera castanea*, *Megascelis* spp, *Melighetes aeneus*, *Melolontha* spp., *Myochrous armatus*, *Orycaephilus* spp., *Otiorhynchus* spp., *Phyllophaga* spp, *Phlyctinus* spp., *Popillia* spp., *Psylliodes* spp., *Rhyssomatus aubtilis*, *Rhizopertha* spp., *Scarabeidae*, *Sitophilus* spp., *Sitotroga* spp., *Somaticus* spp, *Sphenophorus* spp, *Sternechus subsignatus*, *Tenebrio* spp., *Tribolium* spp. and *Trogoderma* spp.;

from the order Diptera, for example,

*Aedes* spp., *Anopheles* spp, *Antherigona soccata*, *Bactrocea oleae*, *Bibio hortulanus*, *Bradysia* spp, *Calliphora erythrocephala*, *Ceratitis* spp., *Chrysomyia* spp., *Culex* spp., *Cuterebra* spp., *Dacus* spp., *Delia* spp, *Drosophila melanogaster*, *Fannia* spp., *Gastrophilus* spp., *Geomyza tripunctata*, *Glossina* spp., *Hypoderma* spp., *Hyppobosca* spp., *Liriomyza* spp., *Lucilia* spp., *Melanagromyza* spp., *Musca* spp., *Oestrus* spp., *Orseolia* spp., *Oscinella frit*, *Pegomyia hyoscyami*, *Phorbia* spp., *Rhagoletis* spp, *Rivelia quadrifasciata*, *Scatella* spp, *Sciara* spp., *Stomoxys* spp., *Tabanus* spp., *Tannia* spp. and *Tipula* spp.;

from the order Hemiptera, for example,

*Acanthocoris scabrator*, *Acrosternum* spp, *Adelphocoris lineolatus*, *Amblypelta nitida*, *Bathycoelia thalassina*, *Blissus* spp, *Cimex* spp., *Clavigralla tomentosicollis*, *Creontiades* spp, *Distantiella theobroma*, *Dichelops furcatus*, *Dysdercus* spp., *Edessa* spp, *Euchistus* spp., *Eurydema pulchrum*, *Eurygaster* spp., *Halyomorpha halys*, *Horcias nobilellus*, *Leptocorisa* spp., *Lygus* spp, *Margarodes* spp, *Murgantia histrionic*, *Neomegalotomus* spp, *Nesidiocoris tenuis*, *Nezara* spp., *Nysius simulans*, *Oebalus insularis*, *Piesma* spp., *Piezodorus* spp, *Rhodnius* spp., *Sahlbergella singularis*, *Scaptocoris castanea*, *Scotinophara* spp., *Thyanta* spp, *Triatoma* spp., *Vatiga illudens*;

*Acyrthosium pisum*, *Adalges* spp, *Agalliana ensigera*, *Agonoscena targionii*, *Aleurodicus* spp, *Aleurocanthus* spp, *Aleurolobus barodensis*, *Aleurothrixus floccosus*, *Aleyrodes brassicae*, *Amarasca biguttula*, *Amritodus atkinsoni*, *Aonidiella* spp., *Aphididae*, *Aphis* spp., *Aspidiotus* spp., *Aulacorthum solani*, *Bactericera cockerelli*, *Bemisia* spp, *Brachycaudus* spp, *Brevicoryne brassicae*, *Cacopsylla* spp, *Cavariella aegopodii* Scop., *Ceroplaster* spp., *Chrysomphalus aonidium*, *Chrysomphalus dictyospermi*, *Cicadella* spp, *Cofana spectra*, *Cryptomyzus* spp, *Cicadulina* spp, *Coccus hesperidum*, *Dalbulus maidis*, *Dialeurodes* spp, *Diaphorina citri*, *Diuraphis noxia*, *Dysaphis* spp, *Empoasca* spp., *Eriosoma larigerum*, *Erythroneura* spp., *Gascardia* spp., *Glycaspis brimblecombei*, *Hyadaphis pseudobrassicae*, *Hyalopterus* spp, *Hyperomyzus pallidus*, *Idioscopus clypealis*, *Jacobiasca lybica*, *Laodelphax* spp., *Lecanium corni*, *Lepidosaphes* spp., *Lopaphis erysimi*, *Lyogenys maidis*, *Macrosiphum* spp., *Mahanarva* spp, *Metcalfa pruinosa*, *Metopolophium dirhodum*, *Myndus crudus*, *Myzus* spp., *Neotoxoptera* sp, *Nephotettix* spp., *Nilaparvata* spp., *Nippolachnus piri* Mats, *Odonaspis ruthae*, *Oregma lanigera* Zehnter, *Parabemisia myricae*, *Paratrioza cockerelli*, *Parlatoria* spp., *Pemphigus* spp., *Peregrinus maidis*, *Perkinsiella* spp, *Phorodon humuli*, *Phylloxera* spp, *Planococcus* spp., *Pseudaulacaspis* spp., *Pseudococcus* spp., *Pseudatomoscelis seriatus*, *Psylla* spp., *Pulvinaria aethiopica*, *Quadraspidiotus* spp., *Quesada gigas*, *Recilia dorsalis*, *Rhopalosiphum* spp., *Saissetia* spp., *Scaphoideus* spp., *Schizaphis* spp., *Sitobion* spp., *Sogatella furcifera*, *Spissistilus festinus*, *Tarophagus Proserpina*, *Toxoptera* spp, *Trialeurodes* spp, *Tridiscus sporoboli*, *Trionymus* spp, *Trioza erytreae*, *Unaspis citri*, *Zygina flammigera*, *Zyginidia scutellaris*;

from the order Hymenoptera, for example,

*Acromyrmex*, *Arge* spp., *Atta* spp., *Cephus* spp., *Diprion* spp., *Diprionidae*, *Gilpinia polytoma*, *Hoplocampa* spp., *Lasius* spp., *Monomorium pharaonis*, *Neodiprion* spp., *Pogonomyrmex* spp, *Slenopsis invicta*, *Solenopsis* spp. and *Vespa* spp.;

from the order Isoptera, for example,

*Coptotermes* spp, *Corniternes cumulans*, *Incisitermes* spp, *Macrotermes* spp, *Mastotermes* spp, *Microtermes* spp, *Reticulitermes* spp.; *Solenopsis geminate* from the order Lepidoptera, for example,

*Acleris* spp., *Adoxophyes* spp., *Aegeria* spp., *Agrotis* spp., *Alabama argillaceae*, *Amylois* spp., *Anticarsia gemmatalis*, *Archips* spp., *Argyresthia* spp, *Argyrotaenia* spp., *Autographa* spp., *Bucculatrix thurberiella*, *Busseola fusca*, *Cadra cautella*, *Carposina nipponensis*, *Chilo* spp., *Choristoneura* spp., *Chrysoteuchia topiaria*, *Clysia ambiguella*,

*Cnaphalocrocis* spp., *Cnephasia* spp., *Cochylis* spp., *Coleophora* spp., *Colias lesbia, Cosmophila flava, Crambus* spp, *Crocidolomia binotalis, Cryptophlebia leucotreta, Cydalima perspectalis, Cydia* spp., *Diaphania perspectalis, Diatraea* spp., *Diparopsis castanea, Earias* spp., *Eldana saccharina, Ephestia* spp., *Epinotia* spp, *Estigmene acrea, Etiella zinckinella, Eucosma* spp., *Eupoecilia ambiguella, Euproctis* spp., *Euxoa* spp., *Feltia jaculiferia, Grapholita* spp., *Hedya nubiferana, Heliothis* spp., *Hellula undalis, Herpetogramma* spp, *Hyphantria cunea, Keiferia lycopersicella, Lasmopalpus lignosellus, Leucoptera scitella, Lithocollethis* spp., *Lobesia botrana, Loxostege bifidalis, Lymantria* spp., *Lyonetia* spp., *Malacosoma* spp., *Mamestra brassicae, Manduca sexta, Mythimna* spp, *Noctua* spp, *Operophtera* spp., *Orniodes indica, Ostrinia nubilalis, Pammene* spp., *Pandemis* spp., *Panolis flammea, Papaipema nebris, Pectinophora gossypiela, Perileucoptera coffeella, Pseudaletia unipuncta, Phthorimaea operculella, Pieris rapae, Pieris* spp., *Plutella xylostella, Prays* spp., *Pseudoplusia* spp, *Rachiplusia nu, Richia albicosta, Scirpophaga* spp., *Sesamia* spp., *Sparganothis* spp., *Spodoptera* spp., *Sylepta derogate, Synanthedon* spp., *Thaumetopoea* spp., *Tortrix* spp., *Trichoplusia ni, Tuta absoluta*, and *Yponomeuta* spp.;

from the order Mallophaga, for example,

*Damalinea* spp. and *Trichodectes* spp.;

from the order Orthoptera, for example,

*Blatta* spp., *Blattella* spp., *Gryllotalpa* spp., *Leucophaea maderae, Locusta* spp., *Neocurtilla hexadactyla, Periplaneta* spp., *Scapteriscus* spp, and *Schistocerca* spp.;

from the order Psocoptera, for example,

*Liposcelis* spp.;

from the order Siphonaptera, for example,

*Ceratophyllus* spp., *Ctenocephalides* spp. and *Xenopsylla cheopis;* from the order Thysanoptera, for example,

*Calliothrips phaseoli, Frankliniella* spp., *Heliothrips* spp, *Hercinothrips* spp., *Parthenothrips* spp, *Scirtothrips aurantii, Sericothrips variabilis, Taeniothrips* spp., *Thrips* spp;

from the order Thysanura, for example, *Lepisma saccharina*.

The active ingredients according to the invention can be used for controlling, i. e. containing or destroying, pests of the abovementioned type which occur in particular on plants, especially on useful plants and ornamentals in agriculture, in horticulture and in forests, or on organs, such as fruits, flowers, foliage, stalks, tubers or roots, of such plants, and in some cases even plant organs which are formed at a later point in time remain protected against these pests.

Suitable target crops are, in particular, cereals, such as wheat, barley, rye, oats, rice, maize or sorghum; beet, such as sugar or fodder beet; fruit, for example pomaceous fruit, stone fruit or soft fruit, such as apples, pears, plums, peaches, almonds, cherries or berries, for example strawberries, raspberries or blackberries; leguminous crops, such as beans, lentils, peas or soya; oil crops, such as oilseed rape, mustard, poppies, olives, sunflowers, coconut, castor, cocoa or ground nuts; cucurbits, such as pumpkins, cucumbers or melons; fibre plants, such as cotton, flax, hemp or jute; citrus fruit, such as oranges, lemons, grapefruit or tangerines; vegetables, such as spinach, lettuce, asparagus, cabbages, carrots, onions, tomatoes, potatoes or bell peppers; Lauraceae, such as avocado, Cinnamonium or camphor; and also tobacco, nuts, coffee, eggplants, sugarcane, tea, pepper, grapevines, hops, the plantain family, latex plants and ornamentals.

The active ingredients according to the invention are especially suitable for controlling *Aphis craccivora, Diabrotica balteata, Heliothis virescens, Myzus persicae, Plutella xylostella* and *Spodoptera littoralis* in cotton, vegetable, maize, rice and soya crops. The active ingredients according to the invention are further especially suitable for controlling *Mamestra* (preferably in vegetables), *Cydia pomonella* (preferably in apples), *Empoasca* (preferably in vegetables, vineyards), *Leptinotarsa* (preferably in potatos) and *Chilo supressalis* (preferably in rice).

In a further aspect, the invention may also relate to a method of controlling damage to plant and parts thereof by plant parasitic nematodes (Endoparasitic-, Semiendoparasitic- and Ectoparasitic nematodes), especially plant parasitic nematodes such as root knot nematodes, *Meloidogyne hapla, Meloidogyne incognita, Meloidogyne javanica, Meloidogyne arenaria* and other *Meloidogyne* species; cyst-forming nematodes, *Globodera rostochiensis* and other *Globodera* species; *Heterodera avenae, Heterodera glycines, Heterodera schachtii, Heterodera trifolii*, and other *Heterodera* species; Seed gall nematodes, *Anguina* species; Stem and foliar nematodes, *Aphelenchoides* species; Sting nematodes, *Belonolaimus longicaudatus* and other *Belonolaimus* species; Pine nematodes, *Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor, Ditylenchus dipsaci* and other *Ditylenchus* species; Awl nematodes, *Dolichodorus* species; Spiral nematodes, *Heliocotylenchus multicinctus* and other *Helicotylenchus* species; Sheath and sheathoid nematodes, *Hemicycliophora* species and *Hemicriconemoides* species; *Hirshmanniella* species; Lance nematodes, *Hoploaimus* species; false rootknot nematodes, *Nacobbus* species; Needle nematodes, *Longidorus elongatus* and other *Longidorus* species; Pin nematodes, *Pratylenchus* species; Lesion nematodes, *Pratylenchus neglectus, Pratylenchus penetrans, Pratylenchus curvitatus, Pratylenchus goodeyi* and other *Pratylenchus* species; Burrowing nematodes, *Radopholus similis* and other *Radopholus* species; Reniform nematodes, *Rotylenchus robustus, Rotylenchus reniformis* and other *Rotylenchus* species; *Scutellonema* species; Stubby root nematodes, *Trichodorus primitivus* and other *Trichodorus* species, *Paratrichodorus* species; Stunt nematodes, *Tylenchorhynchus claytoni, Tylenchorhynchus dubius* and other *Tylenchorhynchus* species; Citrus nematodes, *Tylenchulus* species; Dagger nematodes, *Xiphinema* species; and other plant parasitic nematode species, such as *Subanguina* spp., *Hypsoperine* spp., *Macroposthonia* spp., *Melinius* spp., *Punctodera* spp., and *Quinisulcius* spp.

The compounds of the invention may also have activity against the molluscs. Examples of which include, for example, Ampullariidae; *Arion* (*A. ater, A. circumscriptus, A. hortensis, A. rufus*); Bradybaenidae (*Bradybaena fruticum*); *Cepaea* (*C. hortensis, C. Nemoralis*); ochlodina; *Deroceras* (*D. agrestis, D. empiricorum, D. laeve, D. reticulatum*); *Discus* (*D. rotundatus*); Euomphalia; *Galba* (*G. trunculata*); *Helicelia* (*H. itala, H. obvia*); Helicidae *Helicigona arbustorum*); Helicodiscus; *Helix* (*H. aperta*); *Limax* (*L. cinereoniger, L. flavus, L. marginatus, L. maximus, L. tenellus*); Lymnaea; *Milax* (*M. gagates, M. marginatus, M. sowerbyi*); Opeas; *Pomacea* (*P. canaticulata*); Vallonia and Zanitoides.

The term "crops" is to be understood as including also crop plants which have been so transformed by the use of recombinant DNA techniques that they are capable of synthesising one or more selectively acting toxins, such as are known, for example, from toxin-producing bacteria, especially those of the genus Bacillus.

Toxins that can be expressed by such transgenic plants include, for example, insecticidal proteins, for example insecticidal proteins from *Bacillus cereus* or *Bacillus popilliae*; or insecticidal proteins from *Bacillus thuringiensis*, such as δ-endotoxins, e.g. Cry1Ab, Cry1Ac, Cry1F, Cry1Fa2, Cry2Ab, Cry3A, Cry3Bb1 or Cry9C, or vegetative insecticidal proteins (Vip), e.g. Vip1, Vip2, Vip3 or Vip3A; or insecticidal proteins of bacteria colonising nematodes, for example *Photorhabdus* spp. or *Xenorhabdus* spp., such as *Photorhabdus luminescens, Xenorhabdus nematophilus*; toxins produced by animals, such as scorpion toxins, arachnid toxins, wasp toxins and other insect-specific neurotoxins; toxins produced by fungi, such as Streptomycetes toxins, plant lectins, such as pea lectins, barley lectins or snowdrop lectins; agglutinins; proteinase inhibitors, such as trypsin inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyl-transferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

In the context of the present invention there are to be understood by δ-endotoxins, for example Cry1Ab, Cry1Ac, Cry1F, Cry1Fa2, Cry2Ab, Cry3A, Cry3Bb1 or Cry9C, or vegetative insecticidal proteins (Vip), for example Vip1, Vip2, Vip3 or Vip3A, expressly also hybrid toxins, truncated toxins and modified toxins. Hybrid toxins are produced recombinantly by a new combination of different domains of those proteins (see, for example, WO 02/15701). Truncated toxins, for example a truncated Cry1Ab, are known. In the case of modified toxins, one or more amino acids of the naturally occurring toxin are replaced. In such amino acid replacements, preferably non-naturally present protease recognition sequences are inserted into the toxin, such as, for example, in the case of Cry3A055, a cathepsin-G-recognition sequence is inserted into a Cry3A toxin (see WO 03/018810). Examples of such toxins or transgenic plants capable of synthesising such toxins are disclosed, for example, in EP-A-0 374 753, WO 93/07278, WO 95/34656, EP-A-0 427 529, EP-A-451 878 and WO 03/052073.

The processes for the preparation of such transgenic plants are generally known to the person skilled in the art and are described, for example, in the publications mentioned above. Cry1-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (Coleoptera), two-winged insects (Diptera) and moths (Lepidoptera).

Transgenic plants containing one or more genes that code for an insecticidal resistance and express one or more toxins are known and some of them are commercially available. Examples of such plants are: YieldGard® (maize variety that expresses a Cry1Ab toxin); YieldGard Rootworm® (maize variety that expresses a Cry3Bb1 toxin); YieldGard Plus® (maize variety that expresses a Cry1Ab and a Cry3Bb1 toxin); Starlink® (maize variety that expresses a Cry9C toxin); Herculex I® (maize variety that expresses a Cry1Fa2 toxin and the enzyme phosphinothricine N-acetyltransferase (PAT) to achieve tolerance to the herbicide glufosinate ammonium); NuCOTN 33B® (cotton variety that expresses a Cry1Ac toxin); Bollgard I® (cotton variety that expresses a Cry1Ac toxin); Bollgard II® (cotton variety that expresses a Cry1Ac and a Cry2Ab toxin); VipCot® (cotton variety that expresses a Vip3A and a Cry1Ab toxin); NewLeaf® (potato variety that expresses a Cry3A toxin); NatureGard®, Agrisure® GT Advantage (GA21 glyphosate-tolerant trait), Agrisure® CB Advantage (Bt11 corn borer (CB) trait) and Protecta®.

Further examples of such transgenic crops are:

1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated Cry1Ab toxin. Bt11 maize also transgenically expresses the enzyme PAT to achieve tolerance to the herbicide glufosinate ammonium.

2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a Cry1Ab toxin. Bt176 maize also transgenically expresses the enzyme PAT to achieve tolerance to the herbicide glufosinate ammonium.

3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified Cry3A toxin. This toxin is Cry3A055 modified by insertion of a cathepsin-G-protease recognition sequence. The preparation of such transgenic maize plants is described in WO 03/018810.

4. MON 863 Maize from Monsanto Europe S. A. 270-272 Avenue de Tervuren, B-1150 Brussels, Belgium, registration number C/DE/02/9. MON 863 expresses a Cry3Bb1 toxin and has resistance to certain Coleoptera insects.

5. IPC 531 Cotton from Monsanto Europe S. A. 270-272 Avenue de Tervuren, B-1150 Brussels, Belgium, registration number C/ES/96/02.

6. 1507 Maize from Pioneer Overseas Corporation, Avenue Tedesco, 7 B-1160 Brussels, Belgium, registration number C/NL/00/10. Genetically modified maize for the expression of the protein Cry1F for achieving resistance to certain Lepidoptera insects and of the PAT protein for achieving tolerance to the herbicide glufosinate ammonium.

7. NK603×MON 810 Maize from Monsanto Europe S. A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603× MON 810 Maize transgenically expresses the protein CP4 EPSPS, obtained from *Agrobacterium* sp. strain CP4, which imparts tolerance to the herbicide Roundup® (contains glyphosate), and also a Cry1Ab toxin obtained from *Bacillus thuringiensis* subsp. *kurstaki* which brings about tolerance to certain Lepidoptera, include the European corn borer.

Transgenic crops of insect-resistant plants are also described in BATS (Zentrum für Biosicherheit and Nachhaltigkeit, Zentrum BATS, Clarastrasse 13, 4058 Basel, Switzerland) Report 2003, (http://bats.ch).

The term "crops" is to be understood as including also crop plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225).

Examples of such antipathogenic substances and transgenic plants capable of synthesising such antipathogenic substances are known, for example, from EP-A-0 392 225, WO 95/33818 and EP-A-0 353 191. The methods of producing such transgenic plants are generally known to the person skilled in the art and are described, for example, in the publications mentioned above.

Crops may also be modified for enhanced resistance to fungal (for example *Fusarium*, Anthracnose, or *Phytophthora*), bacterial (for example *Pseudomonas*) or viral (for example potato leafroll virus, tomato spotted wilt virus, cucumber mosaic virus) pathogens.

Crops also include those that have enhanced resistance to nematodes, such as the soybean cyst nematode.

Crops that are tolerance to abiotic stress include those that have enhanced tolerance to drought, high salt, high temperature, chill, frost, or light radiation, for example through expression of NF-YB or other proteins known in the art.

Antipathogenic substances which can be expressed by such transgenic plants include, for example, ion channel blockers, such as blockers for sodium and calcium channels, for example the viral KP1, KP4 or KP6 toxins; stilbene synthases; bibenzyl synthases; chitinases; glucanases; the so-called "pathogenesis-related proteins" (PRPs; see e.g. EP-A-0 392 225); antipathogenic substances produced by microorganisms, for example peptide antibiotics or heterocyclic antibiotics (see e.g. WO 95/33818) or protein or polypeptide factors involved in plant pathogen defence (so-called "plant disease resistance genes", as described in WO 03/000906).

Further areas of use of the compositions according to the invention are the protection of stored goods and store ambients and the protection of raw materials, such as wood, textiles, floor coverings or buildings, and also in the hygiene sector, especially the protection of humans, domestic animals and productive livestock against pests of the mentioned type.

The present invention also provides a method for controlling pests (such as mosquitoes and other disease vectors; see also http://www.who.int/malaria/vector_control/irs/en/). In one embodiment, the method for controlling pests comprises applying the compositions of the invention to the target pests, to their locus or to a surface or substrate by brushing, rolling, spraying, spreading or dipping. By way of example, an IRS (indoor residual spraying) application of a surface such as a wall, ceiling or floor surface is contemplated by the method of the invention. In another embodiment, it is contemplated to apply such compositions to a substrate such as non-woven or a fabric material in the form of (or which can be used in the manufacture of) netting, clothing, bedding, curtains and tents. A further object of the invention is therefore a substrate selected from nonwoven and fabric material comprising a composition which contains a compound of formula I.

In one embodiment, the method for controlling such pests comprises applying a pesticidally effective amount of the compositions of the invention to the target pests, to their locus, or to a surface or substrate so as to provide effective residual pesticidal activity on the surface or substrate. Such application may be made by brushing, rolling, spraying, spreading or dipping the pesticidal composition of the invention. By way of example, an IRS application of a surface such as a wall, ceiling or floor surface is contemplated by the method of the invention so as to provide effective residual pesticidal activity on the surface. In another embodiment, it is contemplated to apply such compositions for residual control of pests on a substrate such as a fabric material in the form of (or which can be used in the manufacture of) netting, clothing, bedding, curtains and tents.

Substrates including non-woven, fabrics or netting to be treated may be made of natural fibres such as cotton, raffia, jute, flax, sisal, hessian, or wool, or synthetic fibres such as polyamide, polyester, polypropylene, polyacrylonitrile or the like. The polyesters are particularly suitable. The methods of textile treatment are known, e.g. WO 2008/151984, WO 2003/034823, U.S. Pat. No. 5,631,072, WO 2005/64072, WO 2006/128870, EP 1724392, WO 2005113886 or WO 2007/090739.

Further areas of use of the compositions according to the invention are the field of tree injection/trunk treatment for all ornamental trees as well all sort of fruit and nut trees.

In the field of tree injection/trunk treatment, the compounds according to the present invention are especially suitable against wood-boring insects from the order Lepidoptera as mentioned above and from the order Coleoptera, especially against woodborers listed in the following tables A and B:

TABLE A

Examples of exotic woodborers of economic importance.

| Family | Species | Host or Crop Infested |
|---|---|---|
| Buprestidae | *Agrilus planipennis* | Ash |
| Cerambycidae | *Anoplura glabripennis* | Hardwoods |
| Scolytidae | *Xylosandrus crassiusculus* | Hardwoods |
| | *X. mutilatus* | Hardwoods |
| | *Tomicus piniperda* | Conifers |

TABLE B

Examples of native woodborers of economic importance.

| Family | Species | Host or Crop Infested |
|---|---|---|
| Buprestidae | *Agrilus anxius* | Birch |
| | *Agrilus politus* | Willow, Maple |
| | *Agrilus sayi* | Bayberry, Sweetfern |
| | *Agrilus vittaticolllis* | Apple, Pear, Cranberry, Serviceberry, Hawthorn |
| | *Chrysobothris femorata* | Apple, Apricot, Beech, Boxelder, Cherry, Chestnut, Currant, Elm, Hawthorn, Hackberry, Hickory, Horsechestnut, Linden, Maple, Mountain-ash, Oak, Pecan, Pear, Peach, Persimmon, Plum, Poplar, Quince, Redbud, Serviceberry, Sycamore, Walnut, Willow |

TABLE B-continued

Examples of native woodborers of economic importance.

| Family | Species | Host or Crop Infested |
|---|---|---|
| | Texania campestris | Basswood, Beech, Maple, Oak, Sycamore, Willow, Yellow-poplar |
| Cerambycidae | Goes pulverulentus | Beech, Elm, Nuttall, Willow, Black oak, Cherrybark oak, Water oak, Sycamore |
| | Goes tigrinus | Oak |
| | Neoclytus acuminatus | Ash, Hickory, Oak, Walnut, Birch, Beech, Maple, Eastern hophornbeam, Dogwood, Persimmon, Redbud, Holly, Hackberry, Black locust, Honeylocust, Yellow-poplar, Chestnut, Osage-orange, Sassafras, Lilac, Mountain-mahogany, Pear, Cherry, Plum, Peach, Apple, Elm, Basswood, Sweetgum |
| | Neoptychodes trilineatus | Fig, Alder, Mulberry, Willow, Netleaf hackberry |
| | Oberea ocellata | Sumac, Apple, Peach, Plum, Pear, Currant, Blackberry |
| | Oberea tripunctata | Dogwood, Viburnum, Elm, Sourwood, Blueberry, Rhododendron, Azalea, Laurel, Poplar, Willow, Mulberry |
| | Oncideres cingulata | Hickory, Pecan, Persimmon, Elm, Sourwood, Basswood, Honeylocust, Dogwood, Eucalyptus, Oak, Hackberry, Maple, Fruit trees |
| | Saperda calcarata | Poplar |
| | Strophiona nitens | Chestnut, Oak, Hickory, Walnut, Beech, Maple |
| Scolytidae | Corthylus columbianus | Maple, Oak, Yellow-poplar, Beech, Boxelder, Sycamore, Birch, Basswood, Chestnut, Elm |
| | Dendroctonus frontalis | Pine |
| | Dryocoetes betulae | Birch, Sweetgum, Wild cherry, Beech, Pear |
| | Monarthrum fasciatum | Oak, Maple, Birch, Chestnut, Sweetgum, Blackgum, Poplar, Hickory, Mimosa, Apple, Peach, Pine |
| | Phloeotribus liminaris | Peach, Cherry, Plum, Black cherry, Elm, Mulberry, Mountain-ash |
| | Pseudopityophthorus pruinosus | Oak, American beech, Black cherry, Chickasaw plum, Chestnut, Maple, Hickory, Hornbeam, Hophornbeam |
| Sesiidae | Paranthrene simulans | Oak, American chestnut |
| | Sannina uroceriformis | Persimmon |
| | Synanthedon exitiosa | Peach, Plum, Nectarine, Cherry, Apricot, Almond, Black cherry |
| | Synanthedon pictipes | Peach, Plum, Cherry, Beach, Black Cherry |
| | Synanthedon rubrofascia | Tupelo |
| | Synanthedon scitula | Dogwood, Pecan, Hickory, Oak, Chestnut, Beech, Birch, Black cherry, Elm, Mountain-ash, Viburnum, Willow, Apple, Loquat, Ninebark, Bayberry |
| | Vitacea polistiformis | Grape |

The present invention may be also used to control any insect pests that may be present in turfgrass, including for example beetles, caterpillars, fire ants, ground pearls, millipedes, sow bugs, mites, mole crickets, scales, mealybugs ticks, spittlebugs, southern chinch bugs and white grubs. The present invention may be used to control insect pests at various stages of their life cycle, including eggs, larvae, nymphs and adults.

In particular, the present invention may be used to control insect pests that feed on the roots of turfgrass including white grubs (such as Cyclocephala spp. (e.g. masked chafer, C. lurida), Rhizotrogus spp. (e.g. European chafer, R. majalis), Cotinus spp. (e.g. Green June beetle, C. nitida), Popillia spp. (e.g. Japanese beetle, P. japonica), Phyllophaga spp. (e.g. May/June beetle), Ataenius spp. (e.g. Black turfgrass ataenius, A. spretulus), Maladera spp. (e.g. Asiatic garden beetle, M. castanea) and Tomarus spp.), ground pearls (Margarodes spp.), mole crickets (tawny, southern, and short-winged; Scapteriscus spp., Gryllotalpa africana) and leatherjackets (European crane fly, Tipula spp.).

The present invention may also be used to control insect pests of turfgrass that are thatch dwelling, including armyworms (such as fall armyworm Spodoptera frugiperda, and common armyworm Pseudaletia unipuncta), cutworms, billbugs (Sphenophorus spp., such as S. venatus verstitus and *S. parvulus*), and sod webworms (such as *Crambus* spp. and the tropical sod webworm, *Herpetogramma phaeopteralis*).

The present invention may also be used to control insect pests of turfgrass that live above the ground and feed on the turfgrass leaves, including chinch bugs (such as southern chinch bugs, *Blissus insularis*), Bermudagrass mite (*Eriophyes cynodoniensis*), rhodesgrass mealybug (*Antonina graminis*), two-lined spittlebug (*Propsapia bicincta*), leafhoppers, cutworms (Noctuidae family), and greenbugs.

The present invention may also be used to control other pests of turfgrass such as red imported fire ants (*Solenopsis invicta*) that create ant mounds in turf.

In the hygiene sector, the compositions according to the invention are active against ectoparasites such as hard ticks, soft ticks, mange mites, harvest mites, flies (biting and licking), parasitic fly larvae, lice, hair lice, bird lice and fleas.

Examples of such parasites are:

Of the order Anoplurida: *Haematopinus* spp., *Linognathus* spp., *Pediculus* spp. and *Phtirus* spp., *Solenopotes* spp.

Of the order Mallophagida: *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

Of the order Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

Of the order Siphonapterida, for example *Pulex* spp., *Ctenocephalides* spp., *Xenopsylla* spp., *Ceratophyllus* spp.

Of the order Heteropterida, for example *Cimex* spp., *Triatoma* spp., *Rhodnius* spp., *Panstrongylus* Spp.

Of the order Blattarida, for example *Blatta orientalis*, *Periplaneta americana*, *Blattelagermanica* and *Supella* spp.

Of the subclass Acaria (Acarida) and the orders Meta- and Meso-stigmata, for example *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

Of the orders Actinedida (Prostigmata) and Acaridida (Astigmata), for example *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The compositions according to the invention are also suitable for protecting against insect infestation in the case of materials such as wood, textiles, plastics, adhesives, glues, paints, paper and card, leather, floor coverings and buildings.

The compositions according to the invention can be used, for example, against the following pests: beetles such as *Hylotrupes bajulus*, *Chlorophorus pilosis*, *Anobium punctatum*, *Xestobium rufovillosum*, *Ptilinuspecticornis*, *Dendrobium pertinex*, *Ernobius mollis*, *Priobium carpini*, *Lyctus brunneus*, *Lyctus africanus*, *Lyctus planicollis*, *Lyctus linearis*, *Lyctus pubescens*, *Trogoxylon aequale*, *Minthesrugicollis*, *Xyleborus* spec., *Tryptodendron* spec., *Apate monachus*, *Bostrychus capucins*, *Heterobostrychus brunneus*, *Sinoxylon* spec. and *Dinoderus minutus*, and also hymenopterans such as *Sirex juvencus*, *Urocerus gigas*, *Urocerus gigas taignus* and *Urocerus augur*, and termites such as *Kalotermes flavicollis*, *Cryptotermes brevis*, *Heterotermes indicola*, *Reticulitermes flavipes*, *Reticulitermes santonensis*, *Reticulitermes lucifugus*, *Mastotermes darwiniensis*, *Zootermopsis nevadensis* and *Coptotermes formosanus*, and bristletails such as *Lepisma saccharina*.

The compounds according to the invention can be used as pesticidal agents in unmodified form, but they are generally formulated into compositions in various ways using formulation adjuvants, such as carriers, solvents and surface-active substances. The formulations can be in various physical forms, e.g. in the form of dusting powders, gels, wettable powders, water-dispersible granules, water-dispersible tablets, effervescent pellets, emulsifiable concentrates, microemulsifiable concentrates, oil-in-water emulsions, oil-flowables, aqueous dispersions, oily dispersions, suspoemulsions, capsule suspensions, emulsifiable granules, soluble liquids, water-soluble concentrates (with water or a water-miscible organic solvent as carrier), impregnated polymer films or in other forms known e.g. from the Manual on Development and Use of FAO and WHO Specifications for Pesticides, United Nations, First Edition, Second Revision (2010). Such formulations can either be used directly or diluted prior to use. The dilutions can be made, for example, with water, liquid fertilisers, micronutrients, biological organisms, oil or solvents.

The formulations can be prepared e.g. by mixing the active ingredient with the formulation adjuvants in order to obtain compositions in the form of finely divided solids, granules, solutions, dispersions or emulsions. The active ingredients can also be formulated with other adjuvants, such as finely divided solids, mineral oils, oils of vegetable or animal origin, modified oils of vegetable or animal origin, organic solvents, water, surface-active substances or combinations thereof.

The active ingredients can also be contained in very fine microcapsules. Microcapsules contain the active ingredients in a porous carrier. This enables the active ingredients to be released into the environment in controlled amounts (e.g. slow-release). Microcapsules usually have a diameter of from 0.1 to 500 microns. They contain active ingredients in an amount of about from 25 to 95% by weight of the capsule weight. The active ingredients can be in the form of a monolithic solid, in the form of fine particles in solid or liquid dispersion or in the form of a suitable solution. The encapsulating membranes can comprise, for example, natural or synthetic rubbers, cellulose, styrene/butadiene copolymers, polyacrylonitrile, polyacrylate, polyesters, polyamides, polyureas, polyurethane or chemically modified polymers and starch xanthates or other polymers that are known to the person skilled in the art. Alternatively, very fine microcapsules can be formed in which the active ingredient is contained in the form of finely divided particles in a solid matrix of base substance, but the microcapsules are not themselves encapsulated.

The formulation adjuvants that are suitable for the preparation of the compositions according to the invention are known per se. As liquid carriers there may be used: water, toluene, xylene, petroleum ether, vegetable oils, acetone, methyl ethyl ketone, cyclohexanone, acid anhydrides, acetonitrile, acetophenone, amyl acetate, 2-butanone, butylene carbonate, chlorobenzene, cyclohexane, cyclohexanol, alkyl esters of acetic acid, diacetone alcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethylformamide, dimethyl sulfoxide, 1,4-dioxane, dipropylene glycol, dipropylene glycol methyl ether, dipropylene glycol dibenzoate, diproxitol, alkylpyrrolidone, ethyl acetate, 2-ethylhexanol, ethylene carbonate, 1,1,1-trichloroethane, 2-heptanone, alpha-pinene, d-limonene, ethyl lactate, ethylene glycol, ethylene glycol butyl ether, ethylene glycol methyl ether, gamma-butyrolactone, glycerol, glycerol acetate, glycerol diacetate, glycerol triacetate, hexadecane, hexylene glycol, isoamyl acetate, isobornyl acetate, isooctane, isophorone, isopropylbenzene, isopropyl myristate, lactic acid, laurylamine, mesityl oxide, methoxypropanol, methyl isoamyl ketone, methyl isobutyl ketone, methyl laurate, methyl octanoate, methyl oleate, methylene chloride, m-xylene, n-hexane, n-octylamine, octadecanoic acid, octylamine acetate, oleic acid, oleylamine, o-xylene, phenol, polyethylene glycol, propionic acid, propyl lactate, propylene carbonate, propylene glycol, propylene glycol methyl ether, p-xylene, toluene, triethyl phosphate, triethylene glycol, xylenesulfonic acid, paraffin, mineral oil, trichloroethylene, perchloroethylene, ethyl acetate, amyl acetate, butyl acetate, propylene glycol methyl ether, diethylene glycol methyl ether, methanol, ethanol, isopropanol, and alcohols of higher molecular weight, such as amyl alcohol, tetrahydrofurfuryl alcohol, hexanol, octanol, ethylene glycol, propylene glycol, glycerol, N-methyl-2-pyrrolidone and the like.

Suitable solid carriers are, for example, talc, titanium dioxide, pyrophyllite clay, silica, attapulgite clay, kieselguhr, limestone, calcium carbonate, bentonite, calcium montmorillonite, cottonseed husks, wheat flour, soybean flour, pumice, wood flour, ground walnut shells, lignin and similar substances.

A large number of surface-active substances can advantageously be used in both solid and liquid formulations, especially in those formulations which can be diluted with a carrier prior to use. Surface-active substances may be anionic, cationic, non-ionic or polymeric and they can be used as emulsifiers, wetting agents or suspending agents or for other purposes. Typical surface-active substances include, for example, salts of alkyl sulfates, such as diethanolammonium lauryl sulfate; salts of alkylarylsulfonates, such as calcium dodecylbenzenesulfonate; alkylphenol/alkylene oxide addition products, such as nonylphenol ethoxylate; alcohol/alkylene oxide addition products, such as tridecylalcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryltrimethylammonium chloride, polyethylene glycol esters of fatty acids, such as polyethylene glycol stearate; block copolymers of ethylene oxide and propylene oxide; and salts of mono- and di-alkylphosphate esters; and also further substances described e.g. in McCutcheon's Detergents and Emulsifiers Annual, MC Publishing Corp., Ridgewood N.J. (1981).

Further adjuvants that can be used in pesticidal formulations include crystallisation inhibitors, viscosity modifiers, suspending agents, dyes, anti-oxidants, foaming agents, light absorbers, mixing auxiliaries, antifoams, complexing agents, neutralising or pH-modifying substances and buffers, corrosion inhibitors, fragrances, wetting agents, take-up enhancers, micronutrients, plasticisers, glidants, lubricants, dispersants, thickeners, antifreezes, microbicides, and liquid and solid fertilisers.

The compositions according to the invention can include an additive comprising an oil of vegetable or animal origin, a mineral oil, alkyl esters of such oils or mixtures of such oils and oil derivatives. The amount of oil additive in the composition according to the invention is generally from 0.01 to 10%, based on the mixture to be applied. For example, the oil additive can be added to a spray tank in the desired concentration after a spray mixture has been prepared. Preferred oil additives comprise mineral oils or an oil of vegetable origin, for example rapeseed oil, olive oil or sunflower oil, emulsified vegetable oil, alkyl esters of oils of vegetable origin, for example the methyl derivatives, or an oil of animal origin, such as fish oil or beef tallow. Preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid (methyl laurate, methyl palmitate and methyl oleate, respectively). Many oil derivatives are known from the Compendium of Herbicide Adjuvants, $10^{th}$ Edition, Southern Illinois University, 2010.

The inventive compositions generally comprise from 0.1 to 99% by weight, especially from 0.1 to 95% by weight, of compounds of the present invention and from 1 to 99.9% by weight of a formulation adjuvant which preferably includes from 0 to 25% by weight of a surface-active substance.

Whereas commercial products may preferably be formulated as concentrates, the end user will normally employ dilute formulations.

The rates of application vary within wide limits and depend on the nature of the soil, the method of application, the crop plant, the pest to be controlled, the prevailing climatic conditions, and other factors governed by the method of application, the time of application and the target crop. As a general guideline compounds may be applied at a rate of from 1 to 2000 l/ha, especially from 10 to 1000 l/ha.

Preferred formulations can have the following compositions (weight %):

Emulsifiable Concentrates:
active ingredient: 1 to 95%, preferably 60 to 90%
surface-active agent: 1 to 30%, preferably 5 to 20%
liquid carrier: 1 to 80%, preferably 1 to 35%
Dusts:
active ingredient: 0.1 to 10%, preferably 0.1 to 5%
solid carrier: 99.9 to 90%, preferably 99.9 to 99%
Suspension Concentrates:
active ingredient: 5 to 75%, preferably 10 to 50%
water: 94 to 24%, preferably 88 to 30%
surface-active agent: 1 to 40%, preferably 2 to 30%
Wettable Powders:
active ingredient: 0.5 to 90%, preferably 1 to 80%
surface-active agent: 0.5 to 20%, preferably 1 to 15%
solid carrier: 5 to 95%, preferably 15 to 90%
Granules:
active ingredient: 0.1 to 30%, preferably 0.1 to 15%
solid carrier: 99.5 to 70%, preferably 97 to 85%

The following Examples further illustrate, but do not limit, the invention.

| Wettable powders | a) | b) | c) |
| --- | --- | --- | --- |
| active ingredients | 25% | 50% | 75% |
| sodium lignosulfonate | 5% | 5% | — |
| sodium lauryl sulfate | 3% | — | 5% |

| Wettable powders | a) | b) | c) |
|---|---|---|---|
| sodium diisobutylnaphthalenesulfonate | — | 6% | 10% |
| phenol polyethylene glycol ether (7-8 mol of ethylene oxide) | — | 2% | — |
| highly dispersed silicic acid | 5% | 10% | 10% |
| Kaolin | 62% | 27% | — |

The combination is thoroughly mixed with the adjuvants and the mixture is thoroughly ground in a suitable mill, affording wettable powders that can be diluted with water to give suspensions of the desired concentration.

| Powders for dry seed treatment | a) | b) | c) |
|---|---|---|---|
| active ingredients | 25% | 50% | 75% |
| light mineral oil | 5% | 5% | 5% |
| highly dispersed silicic acid | 5% | 5% | — |
| Kaolin | 65% | 40% | — |
| Talcum | — | — | 20 |

The combination is thoroughly mixed with the adjuvants and the mixture is thoroughly ground in a suitable mill, affording powders that can be used directly for seed treatment.

| Emulsifiable concentrate | |
|---|---|
| active ingredients | 10% |
| octylphenol polyethylene glycol ether (4-5 mol of ethylene oxide) | 3% |
| calcium dodecylbenzenesulfonate | 3% |
| castor oil polyglycol ether (35 mol of ethylene oxide) | 4% |
| Cyclohexanone | 30% |
| xylene mixture | 50% |

Emulsions of any required dilution, which can be used in plant protection, can be obtained from this concentrate by dilution with water.

| Dusts | a) | b) | c) |
|---|---|---|---|
| Active ingredients | 5% | 6% | 4% |
| Talcum | 95% | — | — |
| Kaolin | — | 94% | — |
| mineral filler | — | — | 96% |

Ready-for-use dusts are obtained by mixing the combination with the carrier and grinding the mixture in a suitable mill. Such powders can also be used for dry dressings for seed.

| Extruder granules | |
|---|---|
| Active ingredients | 15% |
| sodium lignosulfonate | 2% |
| carboxymethylcellulose | 1% |
| Kaolin | 82% |

The combination is mixed and ground with the adjuvants, and the mixture is moistened with water. The mixture is extruded and then dried in a stream of air.

| Coated granules | |
|---|---|
| Active ingredients | 8% |
| polyethylene glycol (mol. wt. 200) | 3% |
| Kaolin | 89% |

The finely ground combination is uniformly applied, in a mixer, to the kaolin moistened with polyethylene glycol. Non-dusty coated granules are obtained in this manner.

| Suspension concentrate | |
|---|---|
| active ingredients | 40% |
| propylene glycol | 10% |
| nonylphenol polyethylene glycol ether (15 mol of ethylene oxide) | 6% |
| Sodium lignosulfonate | 10% |
| carboxymethylcellulose | 1% |
| silicone oil (in the form of a 75% emulsion in water) | 1% |
| Water | 32% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

| Flowable concentrate for seed treatment | |
|---|---|
| active ingredients | 40% |
| propylene glycol | 5% |
| copolymer butanol PO/EO | 2% |
| Tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Slow Release Capsule Suspension 28 parts of the combination are mixed with 2 parts of an aromatic solvent and 7 parts of toluene diisocyanate/polymethylene-polyphenylisocyanate-mixture (8:1). This mixture is emulsified in a mixture of 1.2 parts of polyvinylalcohol, 0.05 parts of a defoamer and 51.6 parts of water until the desired particle size is achieved. To this emulsion a mixture of 2.8 parts 1,6-diaminohexane in 5.3 parts of water is added. The mixture is agitated until the polymerization reaction is completed. The obtained capsule suspension is stabilized by adding 0.25 parts of a thickener and 3 parts of a dispersing agent.

The capsule suspension formulation contains 28% of the active ingredients. The medium capsule diameter is 8-15 microns. The resulting formulation is applied to seeds as an aqueous suspension in an apparatus suitable for that purpose.

Formulation types include an emulsion concentrate (EC), a suspension concentrate (SC), a suspo-emulsion (SE), a capsule suspension (CS), a water dispersible granule (WG), an emulsifiable granule (EG), an emulsion, water in oil (EO), an emulsion, oil in water (EW), a micro-emulsion (ME), an oil dispersion (OD), an oil miscible flowable (OF), an oil miscible liquid (OL), a soluble concentrate (SL), an ultra-low volume suspension (SU), an ultra-low volume liquid (UL), a technical concentrate (TK), a dispersible concentrate (DC), a wettable powder (WP), a soluble granule (SG) or any technically feasible formulation in combination with agriculturally acceptable adjuvants.

PREPARATORY EXAMPLES

"Mp" means melting point in ° C. Free radicals represent methyl groups. $^1$H and $^{19}$F NMR measurements were recorded on Brucker 400 MHz or 300 MHz spectrometers, chemical shifts are given in ppm relevant to a TMS standard. Spectra measured in deuterated solvents as indicated.

LCMS Methods:

Method A—Standard: (SQD-ZDQ-ZCQ)

Spectra were recorded on a Mass Spectrometer from Waters (SQD or ZQ Single quadrupole mass spectrometer) equipped with an electrospray source (Polarity: positive or negative ions, Capillary: 3.00 kV, Cone range: 30-60 V, Extractor: 2.00 V, Source Temperature: 150° C., Desolvation Temperature: 350° C., Cone Gas Flow: 0 L/Hr, Desolvation Gas Flow: 650 L/Hr, Mass range: 100 to 900 Da) and an Acquity UPLC from Waters: Binary pump, heated column compartment and diode-array detector. Solvent degasser, binary pump, heated column compartment and diode-array detector. Column: Waters UPLC HSS T3, 1.8 µm, 30×2.1 mm, Temp: 60° C., DAD Wavelength range (nm): 210 to 500, Solvent Gradient: A=water+5% MeOH+0.05% HCOOH, B=Acetonitrile+0.05% HCOOH: gradient: gradient: 0 min 0% B, 100% A; 1.2-1.5 min 100% B; Flow (ml/min) 0.85

Method B—Standard long: (SQD-ZDQ-ZCQ)

Spectra were recorded on a Mass Spectrometer from Waters (SQD or ZQ Single quadrupole mass spectrometer) equipped with an electrospray source (Polarity: positive or negative ions, Capillary: 3.00 kV, Cone range: 30-60 V, Extractor: 2.00 V, Source Temperature: 150° C., Desolvation Temperature: 350° C., Cone Gas Flow: 0 L/Hr, Desolvation Gas Flow: 650 L/Hr, Mass range: 100 to 900 Da) and an Acquity UPLC from Waters: Binary pump, heated column compartment and diode-array detector. Solvent degasser, binary pump, heated column compartment and diode-array detector. Column: Waters UPLC HSS T3, 1.8 µm, 30×2.1 mm, Temp: 60° C., DAD Wavelength range (nm): 210 to 500, Solvent Gradient: A=water+5% MeOH+0.05% HCOOH, B=Acetonitrile+0.05% HCOOH: gradient: gradient: 0 min 0% B, 100% A; 2.7-3.0 min 100% B; Flow (ml/min) 0.85

Method C—unpolar: (SQD-ZDQ-ZCQ)

Spectra were recorded on a Mass Spectrometer from Waters (SQD or ZQ Single quadrupole mass spectrometer) equipped with an electrospray source (Polarity: positive or negative ions, Capillary: 3.00 kV, Cone range: 30-60 V, Extractor: 2.00 V, Source Temperature: 150° C., Desolvation Temperature: 350° C., Cone Gas Flow: 0 L/Hr, Desolvation Gas Flow: 650 L/Hr, Mass range: 100 to 900 Da) and an Acquity UPLC from Waters: Binary pump, heated column compartment and diode-array detector. Solvent degasser, binary pump, heated column compartment and diode-array detector. Column: Waters UPLC HSS T3, 1.8 µm, 30×2.1 mm, Temp: 60° C., DAD Wavelength range (nm): 210 to 500, Solvent Gradient: A=water+5% MeOH+0.05% HCOOH, B=Acetonitrile+0.05% HCOOH: gradient: gradient: 0 min 40% B, 60% A; 1.2-1.5 min 100% B; Flow (ml/min) 0.85

Synthesis of Intermediates:

Example I1

4-amino-1-cyclopropyl-3-(methylamino)-6-(trifluoromethyl)pyridin-2-one

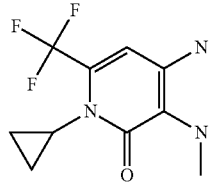 [SMILES: CNc1c(N)cc(C(F)(F)F)n(C2CC2)c1=O]

Step A: 1-cyclopropyl-3-(amino)-6-(trifluoromethyl)pyridin-2-one

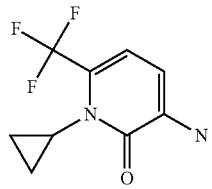 [SMILES: Nc1ccc(C(F)(F)F)n(C2CC2)c1=O]

A sealed bomb was charged with N-[2-oxo-6-(trifluoromethyl)pyran-3-yl]benzamide (commercially available, CAS Registry Number 312615-59-1, 30 g, 105.9 mmol), tetrahydrofuran (132.4 mL, 1620 mmol) and cyclopropylamine (8.24 mL, 116.5 mmol). The mixture was stirred for overnight at 70° C. The sealed vial was cooled and the reaction mixture was dissolved with water and ethyl acetate (250 ml/250 ml).The aqueous phase was extracted with ethyl acetate (3×) and the combined organic layer was dried over sodium sulfate, filtered, concentrated under vacuum. The residue was purified by column chromatography using cyclohexane-ethyl acetate to give the starting material and 23 g of N-[1-cyclopropyl-2-hydroxy-6-oxo-2-(trifluoromethyl)-3H-pyridin-5-yl]benzamide. The N-[1-cyclopropyl-2-hydroxy-6-oxo-2-(trifluoromethyl)-3H-pyridin-5-yl]benzamide was dissolved in hydrogen chloride (563 g, 473.1 mL, 5710 mmol) and the mixture was stirred at 100° C. for 18 hours. The precipitate of Benzoic acid was filtered off and the filtrate was basified to pH 7-8 with a solution of sodium hydroxyl conc. Then the water phase was extracted (3×) with AcOEt and the combined organic layers were dried over sodium sulfate, filtered, concentrated under vacuum. The residue was purified by column chromatography using cyclohexane-ethyl acetate to give 12 g of 1-cyclopropyl-3-(amino)-6-(trifluoromethyl)pyridin-2-one. LC-MS (Method A): RT 0.79, 219 (M$^+$H$^+$). $^1$H NMR (400 MHz, CDCl$_3$) δ ppm 6.59 (d, 1H), 6.33 (d, 1H), 4.60 (sb, 2H), 3.07 (m, 1H), 1.24 (m, 2H), 1.02 (m, 2H).

Step B: 1-cyclopropyl-3-(methylamino)-6-(trifluoromethyl)pyridin-2-one

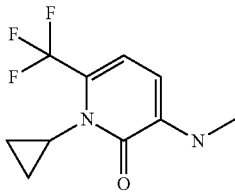 [SMILES: CNc1ccc(C(F)(F)F)n(C2CC2)c1=O]

The 1-cyclopropyl-3-(methylamino)-4-nitro-6-(trifluoromethyl)pyridin-2-one was prepared as for Example 14, step A. LC-MS (Method A): RT 0.93, 233 (M+H⁺).

Step C: 1-cyclopropyl-3-(methylamino)-4-nitro-6-(trifluoromethyl)pyridin-2-one

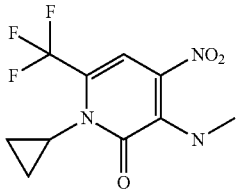 [SMILES: CNc1c([N+](=O)[O-])cc(C(F)(F)F)n(C2CC2)c1=O]

The 1-cyclopropyl-3-(methylamino)-4-nitro-6-(trifluoromethyl)pyridin-2-one was prepared as for Example 12, step C. LC-MS (Method A): RT 0.98, 278 (M+H⁺).

Step D: 4-amino-1-cyclopropyl-3-(methylamino)-6-(trifluoromethyl)pyridin-2-one

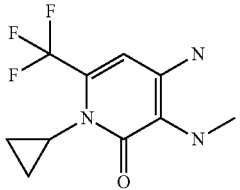 [SMILES: CNc1c(N)cc(C(F)(F)F)n(C2CC2)c1=O]

The 4-amino-1-cyclopropyl-3-(methylamino)-6-(trifluoromethyl)pyridin-2-one was prepared as for Example 12, step D. LC-MS (Method A): RT 0.52, 247 (M+H⁺). Alternatively, the 4-amino-1-cyclopropyl-3-(methylamino)-6-(trifluoromethyl)pyridin-2-one could be prepared via hydrogenation in presence of Pd/C in ethanol using classical reaction. 1H NMR (400 MHz, CDCl3) δ ppm 6.28 (s, 1H), 4.08 (sb, 2H), 3.81 (sb, 1H), 2.97 (m, 1H), 2.63 (s, 3H), 1.18 (m, 2H), 0.98 (m, 2H).

Example I2

3-ethylsulfanyl-5-[3-(trifluoromethyl)pyrazol-1-yl]pyridine-2-carboxylic acid

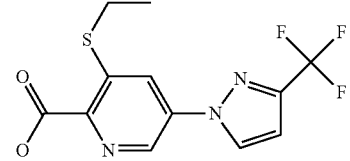

Step A: methyl 3-chloro-5-[3-(trifluoromethyl)pyrazol-1-yl]pyridine-2-carboxylate

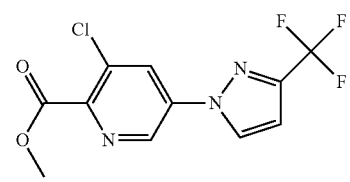 [SMILES: COC(=O)c1ncc(-n2ccc(C(F)(F)F)n2)cc1Cl]

A solution of 2-pyridinecarboxylic acid, 5-bromo-3-chloro-, methyl ester (commercially available, 40.0 g, 160 mmol) in dioxane (1000 mL) was added 3-trifluoromethyl-1H-pyrazole (32.6 g, 240 mmol), (1R,2R)-N1,N2-dimethylcyclohexane-1,2-diamine (5.30 mL, 31.9 mmol), potassium carbonate (48.4 g, 479 mmol) and copper(I) iodide (15.2 g, 79.8 mmol). The reaction mixture was stirred at 100° C. for 24 hours. The reaction mixture was filtered through an Hyflo pad, which was rinsed with methanol, then the dark green reaction mixture was concentrated under vacuum. The residue was subjected to column chromatography over silica gel, eluting with ethyl acetate/cyclohexane. The selected fractions were evaporated and the solid was dissolved in ethyl acetate and washed with HCl 0.5N (to remove the 3-trifluoromethyl-1H-pyrazole that co-migrate with the title product). The ethyl acetate is evaporated to yield the title compound (16 g). LC-MS (Method A): RT 0.98, 306 (M+H⁺).

Step B: 3-ethylsulfanyl-5-[3-(trifluoromethyl)pyrazol-1-yl]pyridine-2-carboxylic acid

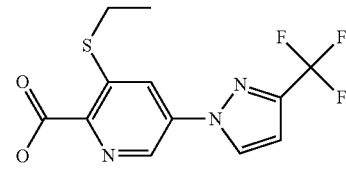 [SMILES: CCSc1cc(-n2ccc(C(F)(F)F)n2)cnc1C(=O)O]

A solution of methyl 3-chloro-5-[3-(trifluoromethyl)pyrazol-1-yl]pyridine-2-carboxylate (preparation described before, 18.0 g, 58.9 mmol) in DMF (200 mL) was added ethanethiol sodium salt (27.4 g, 290 mmol). The reaction mixture was stirred at ambient temperature for 1 h. The reaction mixture was diluted with Ice then water and TBME were added. The organic phase was remove and the aqueous phase was acidified with acetic acid and extracted with TBME and EtOAc (5 times). The combined organic phases dried over sodium sulfate and concentrated under vacuum. The solid was suspended in iPrOH (80 mL) and refluxed for 1.5 hours. It was filtered and the filtrate was allowed to cool down under stirring. The precipitate was filtered to yield the title compound (4.18 g, 22% yield). This compound was used without extra purification. LC-MS (Method A): RT 0.91, 318 (M+H$^+$), 316 (M−H$^+$).

Example P1

N-[1-cyclopropyl-3-(methylamino)-2-oxo-6-(trifluoromethyl)-4-pyridyl]-3-ethylsulfonyl-5-(trifluoromethyl)pyridine-2-carboxamide and N-[4-amino-1-cyclopropyl-2-oxo-6-(trifluoromethyl)-3-pyridyl]-3-ethylsulfonyl-N-methyl-5-(trifluoromethyl)pyridine-2-carboxamide

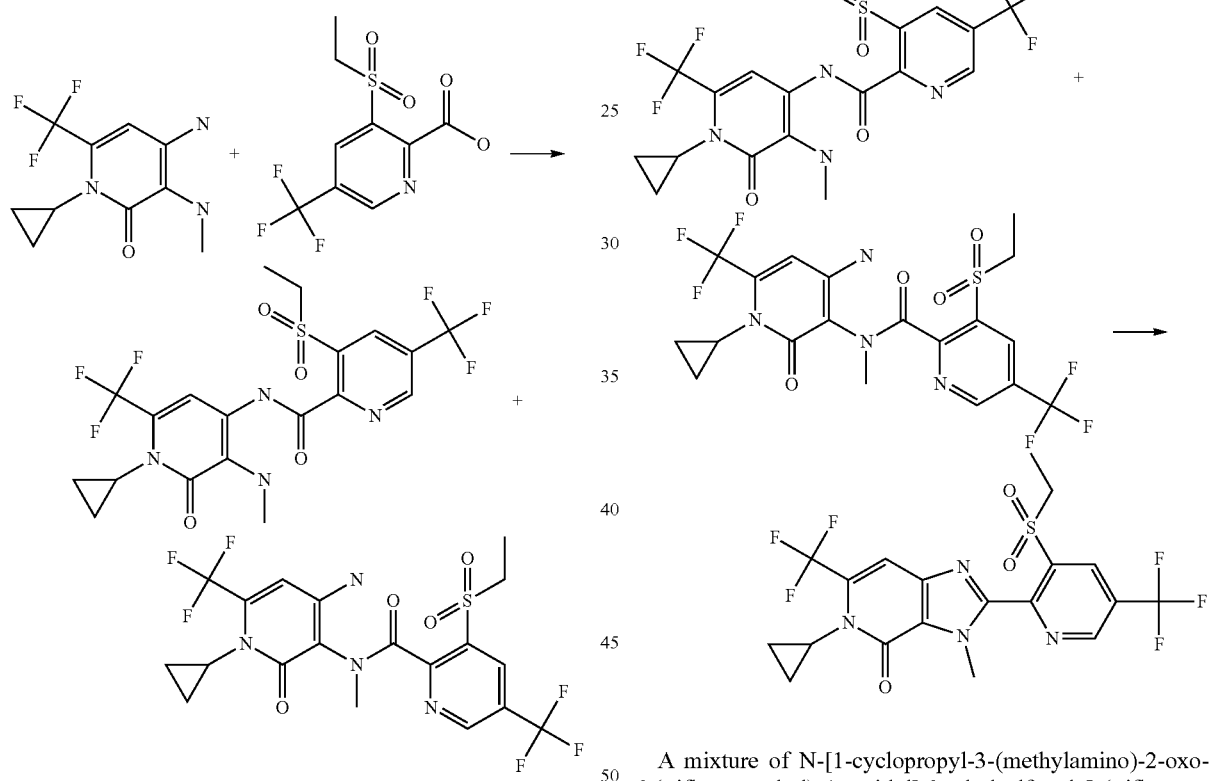

To a suspension of 5-bromo-3-ethylsulfonyl-pyridine-2-carboxylic acid (0.126 g, 0.445 mmol) in dichloromethane (0.9 ml) was added one drop of N,N-dimethylformamide, followed by oxalyl chloride (0.079 mL, 0.89 mmol). After 30 minutes at room temperature, the reaction was stirred 30 minutes at reflux. Then the solvent was removed and dried by vacuum. The 3-ethylsulfonyl-5-(trifluoromethyl)pyridine-2-carbonyl chloride was diluted in 3 mL of tetrahydrofuran and added to a solution of 4-amino-1-cyclopropyl-3-(methylamino)-6-(trifluoromethyl)pyridin-2-one (0.1 g, 0.405 mmol) in tetrahydrofuran (0.81 mL 9 and pyridine (0.1 mL, 1.21 mmol). The mixture was stirred at reflux for 3 hours. The solution was neutralized by addition of a saturated aqueous solution of sodium bicarbonate and the product was extracted twice with ethyl acetate. The organic solution was dried over sodium sulfate and evaporated under reduced pressure to yield the crude product. The residue was purified by column chromatography using cyclohexane-ethyl acetate to give a mixture of N-[1-cyclopropyl-3-(methylamino)-2-oxo-6-(trifluoromethyl)-4-pyridyl]-3-ethylsulfonyl-5-(trifluoromethyl) pyridine-2-carboxamide and N-[4-amino-1-cyclopropyl-2-oxo-6-(trifluoromethyl)-3-pyridyl]-3-ethylsulfonyl-N-methyl-5-(trifluoromethyl)pyridine-2-carboxamide (0.167 g). This mixture was used without extra purification for the next step. LC-MS (Method A): RT 0.94, 513 (M+H$^+$).

Step B: 5-cyclopropyl-2-[3-ethylsulfonyl-5-(trifluoromethyl)-2-pyridyl]-3-methyl-6-(trifluoromethyl) imidazo[4,5-c]pyridin-4-one A1

A mixture of N-[1-cyclopropyl-3-(methylamino)-2-oxo-6-(trifluoromethyl)-4-pyridyl]-3-ethylsulfonyl-5-(trifluoromethyl)pyridine-2-carboxamide and N-[4-amino-1-cyclopropyl-2-oxo-6-(trifluoromethyl)-3-pyridyl]-3-ethylsulfonyl-N-methyl-5-(trifluoromethyl)pyridine-2-carboxamide (0.167 g, 0.3259 mmol, the product of step A) in 1.63 ml of acetic acid AcOH was heated at 150° C. for 2 h and 45 minutes under microwave. A mixture of water (10 mL) and AcOEt (10 mL) was added and the product was extracted twice with ethyl acetate. The combinated organic phases were dried over sodium sulfate and evaporated under reduced pressure. The residue was purified by column chromatography using cyclohexane-ethyl acetate to give 5-cyclopropyl-2-[3-ethylsulfonyl-5-(trifluoromethyl)-2-pyridyl]-3-methyl-6-(trifluoromethyl) imidazo[4,5-c]pyridin-4-one A1 (93 mg). $^1$H NMR (400 MHz, CDCl$_3$) δ ppm: 9.21 (s, 1H); 8.74 (s, 1H); 7.19 (s, 1H); 4.11 (s, 3H); 3.88 (q, 2H); 3.11 (m, 1H); 1.37 (t, 3H); 1.27 (m, 2H); 1.07 (m, 2H).

Example P2

5-cyclopropyl-2-[3-ethylsulfanyl-5-[3-(trifluoromethyl)pyrazol-1-yl]-2-pyridyl]-3-methyl-6-(trifluoromethyl)imidazo[4,5-c]pyridin-4-one A2

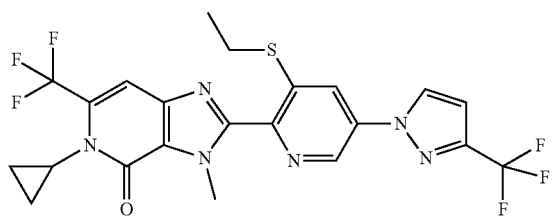 [SMILES: CCSc1cc(-n2ccc(C(F)(F)F)n2)cnc1-c1nc2cc(C(F)(F)F)n(C3CC3)c(=O)c2n1C]

Step A: The 5-cyclopropyl-2-[3-ethylsulfanyl-5-[3-(trifluoromethyl)pyrazol-1-yl]-2-pyridyl]-3-methyl-6-(trifluoromethyl)imidazo[4,5-c]pyridin-4-one A2 was prepared using the step A and step B of the example P1 and the 3-ethylsulfanyl-5-[3-(trifluoromethyl)pyrazol-1-yl]pyridine-2-carboxylic acid (Example I2) as starting material. $^{1}$H-NMR (CDCl$_3$, ppm) 8.78 m, 1H), 8.15 (d, 1H), 8.10 (d, 1H), 7.31 (s, 1H), 6.83 (d, 1H), 6.83 (d, 1H), 4.21 (s, 3H), 3.12 (m, 1H), 3.05 (q, 2H), 1.41 (t, 3H), 1.28 (m, 2H), 1.05 (m, 2H).

Example P3

5-cyclopropyl-2-[3-ethylsulfonyl-5-[3-(trifluoromethyl)pyrazol-1-yl]-2-pyridyl]-3-methyl-6-(trifluoromethyl)imidazo[4,5-c]pyridin-4-one A3

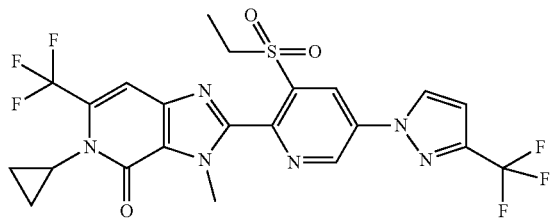 [SMILES: CCS(=O)(=O)c1cc(-n2ccc(C(F)(F)F)n2)cnc1-c1nc2cc(C(F)(F)F)n(C3CC3)c(=O)c2n1C]

A solution of: 5-cyclopropyl-2-[3-ethylsulfanyl-5-[3-(trifluoromethyl)pyrazol-1-yl]-2-pyridyl]-3-methyl-6-(trifluoromethyl)imidazo[4,5-c]pyridin-4-one A2 (preparation described before) in dichloromethane (3.7 ml) was added mCPBA (70 wt % in water) (112 mg, 0.45 mmol) in one portion and mixture was stirred at ambient temperature for 2 hours. The reaction mixture was diluted with dichloromethane and water, then after separation, the organic phase was washed with a solution of 10% NaHSO$_3$, then with a solution of NaOH 1M. The organic phase is dried over sodium sulfate and concentrated under vacuum. The residue was purified over silica by flash column chromatography (ethyl acetate-cyclohexane). The fractions containing product were combined and concentrated to afford the title compound (92 mg) as a solid. $^{1}$H NMR (400 MHz, CDCl$_3$) δ ppm 1.07 (m, 2H), 1.27-1.33 (m, 2H), 1.40 (t, 3H), 3.11 (m, 1H), 3.88 (q, 2H), 4.07 (s, 3H), 6.90 (d, 1H), 7.19 (s, 1H), 8.20 (s, 1H), 8.79 (s, 1H), 9.43 (s, 1H).

Example P4

2-(5-bromo-3-ethylsulfanyl-2-pyridyl)-5-cyclopropyl-3-methyl-6-(trifluoromethyl)imidazo[4,5-c]pyridin-4-one A4

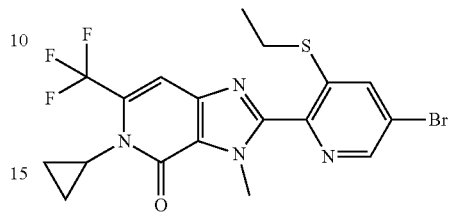

Step A: Preparation of 5-bromo-N-[1-cyclopropyl-3-(methylamino)-2-oxo-6-(trifluoromethyl)-4-pyridyl]-3-ethylsulfanyl-pyridine-2-carboxamide and N-[4-amino-1-cyclopropyl-2-oxo-6-(trifluoromethyl)-3-pyridyl]-5-bromo-3-ethylsulfanyl-N-methyl-pyridine-2-carboxamide

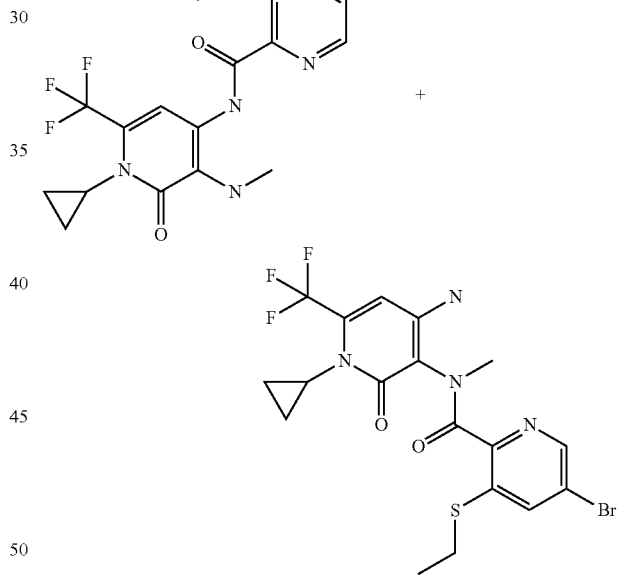

The mixture of 5-bromo-N-[1-cyclopropyl-3-(methylamino)-2-oxo-6-(trifluoromethyl)-4-pyridyl]-3-ethylsulfanyl-pyridine-2-carboxamide and N-[4-amino-1-cyclopropyl-2-oxo-6-(trifluoromethyl)-3-pyridyl]-5-bromo-3-ethylsulfanyl-N-methyl-pyridine-2-carboxamide was prepared using the step A of the example P1. LC-MS (Method A): RT 0.92, 491 (M+H$^+$).

Step B: Preparation of 2-(5-bromo-3-ethylsulfanyl-2-pyridyl)-5-cyclopropyl-3-methyl-6-(trifluoromethyl)imidazo[4,5-c]pyridin-4-one A4

A solution of a mixture of 5-bromo-N-[1-cyclopropyl-3-(methylamino)-2-oxo-6-(trifluoromethyl)-4-pyridyl]-3-ethylsulfanyl-pyridine-2-carboxamide and N-[4-amino-1-cyclopropyl-2-oxo-6-(trifluoromethyl)-3-pyridyl]-5-bromo-3-ethylsulfanyl-N-methyl-pyridine-2-carboxamide (0.05 g, 0.10 mmol, the product of step A) in 1.9 ml of 1,2-dichloroethane was charged with p-toluenesulfonic acid monohydrate (0.009 g, 0.051 mmol) and heated at 150° C. for 30 minutes under microwaves. Then, the solvent was evaporated under reduced pressure and the residue was submitted to flash chromatography over silica gel (ethyl acetate/cyclohexane) and the selected fractions evaporated to yield 2-(5-bromo-3-ethylsulfanyl-2-pyridyl)-5-cyclopropyl-3-methyl-6-(trifluoromethyl)imidazo[4,5-c]pyridin-4-one A4 (0.032 g). $^1$H NMR (400 MHz, CDCl$_3$) δ ppm: 8.52 (d, 1H); 8.32 (d, 1H); 7.29 (s, 1H); 4.17 (s, 3H), 3.10 (m, 1H), 2.94 (q, 2H); 1.35 (t, 3H); 1.27 (m, 2H), 1.04 (m, 2H).

Example P5

5-cyclopropyl-2-[5-(3,5-difluorophenyl)-3-ethylsulfonyl-2-pyridyl]-3-methyl-6-(trifluoromethyl)imidazo[4,5-c]pyridin-4-one A6

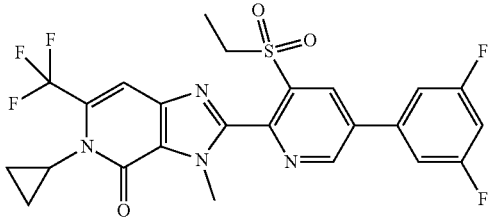 [SMILES: CCS(=O)(=O)c1cc(-c2cc(F)cc(F)c2)cnc1-c1nc2cc(C(F)(F)F)n(C3CC3)c(=O)c2n1C]

in A 20 mL sealed vial flushed with Argon was charged with 2-(5-bromo-3-ethylsulfonyl-2-pyridyl)-5-cyclopropyl-3-methyl-6-(trifluoromethyl)imidazo[4,5-c]pyridin-4-one A5 (preparation described before: see table, 0.15 g, 0.30 mmol), then 3,5-difluorophenyl)boronic acid (0.048 g, 0.30 mmol), tetrakis (triphenylphosphine) palladium(0) (0.011 g, 0.0090 mmol), sodium hydrogen carbonate (1.30 g, 0.59 mmol) in isopropanol (5.9 mL).The mixture flushed with Ar, then, stirred for 4 hours at 100° C. The reaction was stopped by addition of a mixture of water and ethyl acetate. The water layer was extracted, three times, with ethyl acetate. The combined organic layers were dried on magnesium sulfate and concentrated under vacuum. The residue was purified by flash chromatography (cyclohexane/ethyl acetate) to give the title compound (0.082 g). $^1$H NMR (400 MHz, CDCl$_3$) d ppm 9.14 (d, 1H), 8.62 (d, 1H), 7.25 (m, 2H), 7.19 (s, 1H), 6.99 (m, 1H), 4.08 (s, 3H), 3.83 (q, 2H), 3.11 (m, 1H), 1.40 (t, 3H), 1.28 (m, 2H), 1.07 (m, 2H).

Example P6

5-cyclopropyl-2-[3-ethylsulfonyl-5-[4-(trifluoromethyl)-2-pyridyl]-2-pyridyl]-3-methyl-6-(trifluoromethyl)imidazo[4,5-c]pyridin-4-one A7

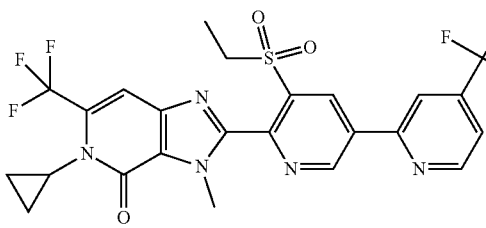

Step A: 5-cyclopropyl-2-[3-ethylsulfonyl-5-(4,4,5,5-tetramethyl-1,3,2-dioxaborolan-2-yl)-2-pyridyl]-3-methyl-6-(trifluoromethyl)imidazo[4,5-c]pyridin-4-one

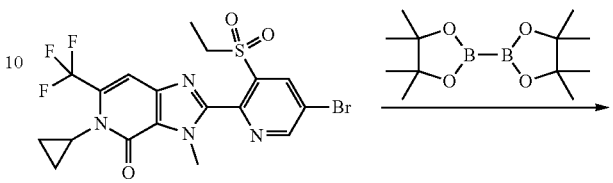

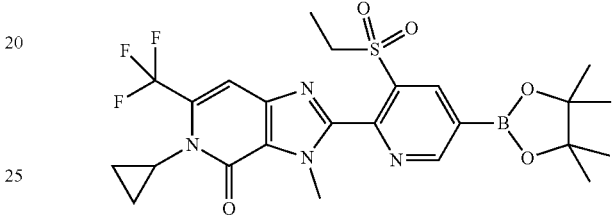

A mixture of A5 (preparation described above) (0.5 g, 0.99 mmol), potassium acetate (0.491 g, 4.95 mmol) and 4,4,5,5-tetramethyl-2-(4,4,5,5-tetramethyl-1,3,2-dioxaborolan-2-yl)-1,3,2-dioxaborolane (0.754 g, 2.97 mmol) in dioxane (3 mL) was gently flushed with argon, then 1,1'-bis (diphenylphosphino)-ferrocene) dichloropalladium-dichloromethane (1:1) complex (0.0148 g, 0.0198 mmol) was added and the pale yellow mixture was heated at 110° C. for 30 min. under microwave. After consumption of the starting bromide, the dark reaction mixture was diluted with water (30 ml) and extracted twice with ethyl acetate (3×30 mL). The combined organic phases were dried over sodium sulfate and concentrated under reduced pressure. The residue was subjected to column chromatography over silica gel, eluting with ethyl acetate/cyclohexane. The selected fractions were evaporated to yield the title compound (0.52 g). $^1$H NMR (400 MHz, CDCl$_3$) δ ppm 1.08 (m, 2H), 1.24-1.43 (m, 17H), 3.10 (m, 1H), 3.72 (q, 2H), 4.01 (s, 3H), 7.19 (s, 1H), 8.83 (s, 1H), 9.23 (s, 1H).The compound was used without extra purification in the next step.

Step B: 5-cyclopropyl-2-[3-ethylsulfonyl-5-[4-(trifluoromethyl)-2-pyridyl]-2-pyridyl]-3-methyl-6-(trifluoromethyl)imidazo[4,5-c]pyridin-4-one A7

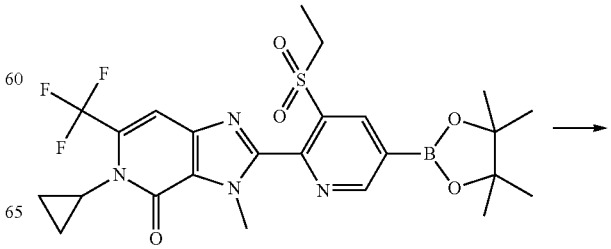

-continued

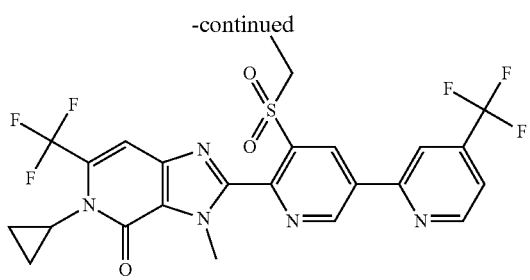

A 5 mL microwave vial flushed with Argon was charged with 2-bromo-4-(trifluoromethyl)pyridine (0.0923 mL, 0.724 mmol), 5-cyclopropyl-2-[3-ethylsulfonyl-5-(4,4,5,5-tetramethyl-1,3,2-dioxaborolan-2-yl)-2-pyridyl]-3-methyl-6-(trifluoromethyl)imidazo[4,5-c]pyridin-4-one (Step A, 0.2 g), tetrakis (triphenylphosphine) palladium(0) (0.042 g, 0.036 mmol), potassium phosphate tribasic (0.48 g, 2.17 mmol), toluene (2.9 mL) and water (2.9 mL). The mixture was then heated 30' at 110° C. under microwave. The reaction mixture was diluted with water and ethyl acetate then, after separation of the phases, the aqueous phase was extracted two time with ethyl acetate. The combined organic phases were dried over sodium sulfate and concentrated under vacuum. The residue was subjected to column chromatography over silica gel, eluting with ethyl acetate/cyclohexane. The selected fractions were evaporated to yield the title compound as a white solid (0.11 g). $^1$H NMR (400 MHz, CDCl$_3$) δ ppm 1.08 (m, 2H), 1.30 (m, 2H), 1.40 (t, 3H), 3.11 (m, 1H), 3.85 (q, 2H), 4.09 (s, 3H), 7.20 (s, 1H), 7.65 (d, 1H), 8.11 (s, 1H), 9.00 (d, 1H), 9.11 (s, 1H).

Example P7

Preparation of Compounds A10 to A29

1. Boronic acids (2 eq.) are weighed manually into a conical microwave vial. 0.5 mL DME is added with a multipipette.
2. A stock solution of 2-(5-bromo-3-ethylsulfonyl-2-pyridyl)-5-cyclopropyl-3-methyl-6-(trifluoromethyl)imidazo[4,5-c]pyridin-4-one A5 (preparation described before) was prepared by mixing 265 mg in 7.8 mL DME.
3. A stock suspension of the X-Phos precatalyst Buchwald 2 d Generation (0.1 eq.) is done by mixing 48 mg in 6 mL.
0.3 mL of solution 2. was added into vials. followed by 0.3 mL water, 40 uL of a solution of sodium carbonate (2 M) and 0.2 mL of solution 3. The vials were flushed with argon and capped. Then, the vials were heat in a microwave oven at 100° C. for 7 min. The solvents were evaporated and a mixture of water and ethyl acetate were added to the vial. The aqueous phase was extracted 3× with ethyl acetate. The combined organic layers were dried on magnesium sulfate and concentrated under vacuum. The residue was purified by reverse phase preparative system.

LC-MS Method for Analytic:
ACQUITY SQD Mass Spectrometer from Waters (Single quadrupole mass spectrometer)
Ionisation method: Electrospray
Polarity: positive ions
Capillary (kV) 3.00, Cone (V) 60.00, Extractor (V) 3.00, Source Temperature (° C.) 150, Desolvation Temperature (° C.) 400, Cone Gas Flow (L/Hr) 60, Desolvation Gas Flow (L/Hr) 700
Mass range: 100 to 800 Da
DAD Wavelength range (nm): 210 to 400

Method Waters ACQUITY UPLC with the following HPLC gradient conditions (Solvent A: Water/Methanol 9:1, 0.1% formic acid and Solvent B: Acetonitrile, 0.1% formic acid)

| Time (minutes) | A (%) | B (%) | Flow rate (ml/min) |
|---|---|---|---|
| 0 | 100 | 0 | 0.75 |
| 2.5 | 0 | 100 | 0.75 |
| 2.8 | 0 | 100 | 0.75 |
| 3.0 | 100 | 0 | 0.75 |

Type of column: Waters ACQUITY UPLC HSS T3; Column length: 30 mm; Internal diameter of column: 2.1 mm; Particle Size: 1.8 micron; Temperature: 60° C.

| | RT | M (calculated) | (M + H)$^+$ (measured) |
|---|---|---|---|
| A10 | 2.02 | 638.10 | 639.43 |
| A11 | 1.75 | 520.12 | 521.40 |
| A12 | 1.45 | 534.13 | 535.41 |
| A13 | 1.32 | 504.12 | 505.38 |
| A14 | 1.29 | 503.12 | 504.39 |
| A15 | 1.93 | 586.11 | 587.43 |
| A16 | 1.86 | 548.12 | 549.41 |
| A17 | 1.88 | 570.12 | 571.42 |
| A18 | 1.96 | 570.05 | 571.35 |
| A19 | 1.99 | 570.05 | 571.36 |
| A20 | 1.75 | 550.13 | 551.43 |
| A21 | 1.71 | 571.11 | 572.42 |
| A22 | 1.76 | 520.12 | 521.40 |
| A23 | 1.93 | 586.11 | 587.42 |
| A24 | 1.78 | 538.11 | 539.40 |
| A25 | 1.84 | 556.10 | 557.40 |
| A26 | 1.78 | 538.11 | 539.39 |
| A27 | 1.93 | 588.11 | 589.42 |
| A28 | 1.90 | 554.08 | 555.37 |
| A29 | 1.75 | 502.13 | 503.38 |

Example P8

Preparation of 1-[6-[5-cyclopropyl-3-methyl-4-oxo-6-(trifluoromethyl)imidazo[4,5-c]pyridin-2-yl]-5-ethylsulfonyl-3-pyridyl]cyclopropanecarbonitrile A31

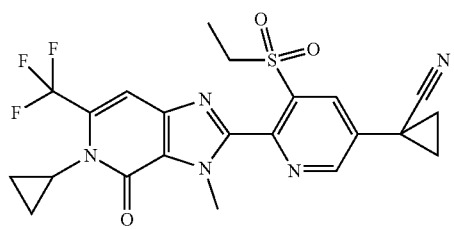 [SMILES: CCS(=O)(=O)c1cc(C2(C#N)CC2)cnc1-c1nc2cc(C(F)(F)F)n(C3CC3)c(=O)c2n1C]

Step 1: Preparation of methyl 5-bromo-3-ethylsulfanyl-pyridine-2-carboxylate

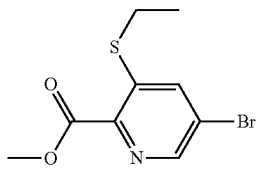

To a solution of methyl 5-bromo-3-chloro-pyridine-2-carboxylate (0.100 g, 0.399 mmol) (commercial product) in THF, stirred at 0° C., was added sodium ethanolate (0.034 g, 0.399 mmol). After 1 hour at that temperature, the ice bath was removed and stirring was continued for 20 hours. The reaction mixture was then poured onto water (15 ml) and extracted twice with EtOAc. The combined organic phases were dried over sodium sulfate and the solvent was removed in vacuo. The residue was submitted to flash chromatography over silica gel and the selected fractions evaporated to yield methyl 5-bromo-3-ethylsulfanyl-pyridine-2-carboxylate as a colorless solid.

LCMS (method 1): 276, 278 (M+H); retention time: 0.92 min.

$^1$H NMR (400 MHz, CDCl$_3$) δ ppm: 8.46 (s, 1H); 7.79 (s, 1H); 4.00 (s, 3H); 2.94 (q, 2H); 1.42 (t, 3H).

Step 2: Preparation of Methyl 5-bromo-3-ethylsulfonyl-pyridine-2-carboxylate

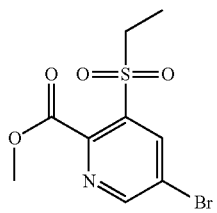 [SMILES: CCS(=O)(=O)c1cc(Br)cnc1C(=O)OC]

Methyl-5-bromo-3-ethylsulfanyl-pyridine-2-carboxylate (24.4 g, 88.4 mmol) was suspended in dichloromethane (250 mL), cooled to 0° C., and treated portion wise with MCPBA (37.6 g, 185.7 mmol). The mixture was stirred at ambient temperature for 18 hours. The mixture was diluted with water and dichloromethane, the aqueous phase was back extracted with dichloromethane (2×), and the combined organic phases washed with Na$_2$S$_2$O$_4$, dried over Na$_2$SO$_4$. Partial concentration of the solvent, led to a solid (the desired title compound) that was filtered. The filtrate was evaporated to dryness, which was purified by chromatography on silica to give further pure title compound as white solid.

LCMS (method A): 308/310 (M+H)$^+$; retention time: 0.76 min.

1H NMR: (d$^6$-DMSO, 400 MHz): 9.08 (d, 1H), 8.58 (d, 1H), 3.87 (s, 3H), 3.52 (q, 2H), 1.18 (t, 3H).

Step 3: Preparation of Methyl 5-(cyanomethyl)-3-ethylsulfonyl-pyridine-2-carboxylate

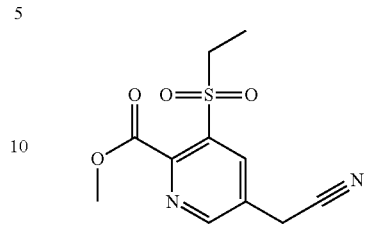

A solution of methyl-5-bromo-3-ethylsulfonyl-pyridine-2-carboxylate, (2.00 g, 6.49 mmol) in DMF (13.0 mL) was treated with TMS-acetonitrile (2.25 g, 2.71 mL, 19.5 mmol), difluorozinc (0.403 g, 3.89 mmol), Xantphos (0.153 g, 0.260 mmol) and Pd$_2$(dba)$_3$ (0.119 g, 0.130 mmol) under argon. The resulting mixture was stirred for 5 hours at 100° C. LCMS after this time showed no further reaction progression. The mixture was cooled, diluted with EtOAc, and filtered over hyflo. The filtrate was washed with water/NH4Cl, brine, dried over Na$_2$SO$_4$, filtered and concentrated in vacuo. The crude product was purified by combi flash chromatography with a column of 40 g and a gradient cyclohexane+0-50% ethyl acetate. This gave the title compound as yellow oil.

LCMS (method A): 269 (M+H)$^+$; retention time: 0.58 min.

$^1$H NMR (400 MHz, CHLOROFORM-d) δ ppm: 1.38 (t, 3H), 3.58 (q, 2H), 3.95 (s, 2H), 4.06 (s, 3H), 8.37 (d, 1H), 8.86 (d, 1H).

Step 4: Preparation of Methyl 5-(1-cyanocyclopropyl)-3-ethylsulfonyl-pyridine-2-carboxylate

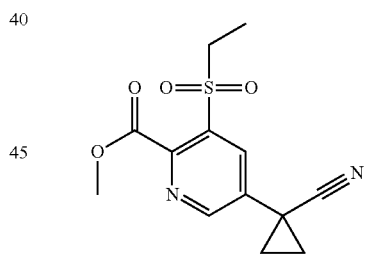

Methyl 5-(cyanomethyl)-3-ethylsulfonyl-pyridine-2-carboxylate (0.63 g, 2.3 mmol) was dissolved in acetonitrile (19 mL) and cesium carbonate (2.3 g, 7.0 mmol) was added to the colorless solution (solution darkened), followed by addition of 1,2-dibromoethane (0.90 g, 0.41 mL, 4.7 mmol) The brown solution was stirred at 80° C. bath temperature. LC/MS detected desired mass at 0.73 after 1.5 h.

The reaction mixture was concentrated in vacuo and diluted with EtOAc and water. The organic layer was separated, washed successively with water and brine, dried over Na$_2$SO$_4$, filtered and concentrated in vacuo. The crude product was dissolved in dichloromethane and adsorbed onto TEFLON BULK SORBENTS. Purification over a silica gel cartridge (Rf200) eluting with cyclohexane/EtOAc, gave the title compound as a beige resin.

LCMS (method A): 295 (M+H)$^+$; retention time: 0.72 min.

$^1$H NMR (400 MHz, CHLOROFORM-d) δ ppm: 1.36 (t, 3H), 1.57-1.62 (m, 2H), 1.95-2.00 (m, 2H), 2.05 (s, 2H), 4.04 (s, 4H), 8.13 (d, 1H), 8.87 (d, 1H).

Step 5: Preparation of 5-(1-cyanocyclopropyl)-3-ethylsulfonyl-pyridine-2-carboxylic acid

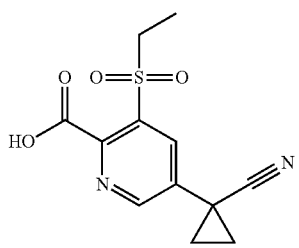 [SMILES: CCS(=O)(=O)c1cc(C2(C#N)CC2)cnc1C(=O)O]

A solution of methyl 5-(1-cyanocyclopropyl)-3-ethylsulfonyl-pyridine-2-carboxylate (0.27 g, 0.92 mmol) was dissolved in THF (4 mL) and water (1.5 mL) (red solution), and then treated with LiOH.H$_2$O (0.058 g, 1.4 mmol) The mixture was stirred at ambient temperature for 2 hours by which time LCMS analysis showed reaction completion (only desired product at Rt=0.32, method 1). The THF was evaporated in vacuo and the residue was acidified with 1M HCl and extracted with EtOAc. The organic layer was washed with brine, dried over Na$_2$SO$_4$ filtrated and concentrated in vacuo to give pure title product as beige solid.

LCMS (method A): 281 (M+H)$^+$; retention time: 0.30 min.

$^1$H NMR (400 MHz, methanol-d$_4$) δ ppm: 1.31 (t, 3H), 1.71-1.78 (m, 2H), 1.92-1.98 (m, 2H), 3.60 (q, 2H), 8.28 (d, 1H), 8.83 (d, 1H).

Step 5: Preparation of 1-[6-[5-cyclopropyl-3-methyl-4-oxo-6-(trifluoromethyl)imidazo[4,5-c]pyridin-2-yl]-5-ethylsulfonyl-3-pyridyl]cyclopropanecarbonitrile A31: the compound A31 was prepared using a protocol similar at the one used in Example P4 (Step A and Step B): LCMS (method A): 492 (M+H)$^+$; retention time: 0.97 min.

Example P9

Preparation of 2-[5-(3-chloro-1,2,4-triazol-1-yl)-3-ethylsulfanyl-2-pyridyl]-5-cyclopropyl-3-methyl-6-(trifluoromethyl)imidazo[4,5-c]pyridin-4-one A33 and 2-[5-(3-chloro-1,2,4-triazol-1-yl)-3-ethylsulfonyl-2-pyridyl]-5-cyclopropyl-3-methyl-6-(trifluoromethyl)imidazo[4,5-c]pyridin-4-one A34

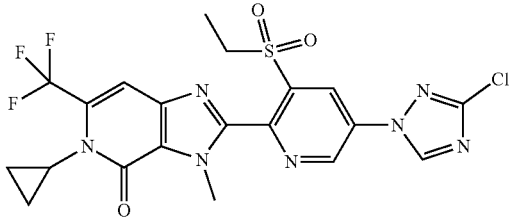

A34

Step A: 2-[5-(3-chloro-1,2,4-triazol-1-yl)-3-ethylsulfanyl-2-pyridyl]-5-cyclopropyl-3-methyl-6-(trifluoromethyl)imidazo[4,5-c]pyridin-4-one A33

A solution 2-(5-bromo-3-ethylsulfanyl-2-pyridyl)-5-cyclopropyl-3-methyl-6-(trifluoromethyl)imidazo[4,5-c]pyridin-4-one A4 (Prepared as described before, 150 mg, 0.3169 mmol) in N,N-dimethylformamide (0.3169 mL) was added 3-chloro-1H-1,2,4-triazole (36.09 mg, 0.3486 mmol), (1R, 2R)-N1,N2-dimethylcyclohexane-1,2-diamine (2.822 mg, 0.00341 mL, 0.03169 mmol), potassium carbonate (8.760 mg, 0.064 mmol) and copper(I) iodide (3.018 mg, 0.01585 mmol). The reaction mixture was stirred at reflux overnight. Same quantity of N,N'-dimethylethylenediamine, copper(I) iodide and potassium carbonate were added at the mixture and the mixture was stirred at 120° C. overnight. The reaction mixture was filtered through an Hyflo pad, which was rinsed with methanol, then the reaction mixture was concentrated under vacuum. The residue was subjected to column chromatography over silica gel, eluting with ethyl acetate/cyclohexane. The selected fractions were evaporated to yield the title compound (30% yield). LC-MS (Method A): RT 1.08, 476 (M+H$^+$).

Step B: 2-[5-(3-chloro-1,2,4-triazol-1-yl)-3-ethylsulfonyl-2-pyridyl]-5-cyclopropyl-3-methyl-6-(trifluoromethyl)imidazo[4,5-c]pyridin-4-one A34

A34 was prepared as described in Example P3 (via oxidation of the sulfur of A33): LC-MS (Method A) RT 1.02, 528 (MH+). $^1$H NMR (400 MHz, methanol-d$_4$) δ ppm: 9.35 (d, 1H), 8.76 (d, 1H), 8.72 (s, 1H), 7.19 (s, 1H), 4.09 (s, 3H), 3.90 (q, 2H), 3.11 (m, 1H), 1.42 (t, 3H), 1.28 (m, 2H), 1.07 (m, 2H).

Table A: This table discloses compounds of the formula I-1a. "Ph" represents the phenyl group:

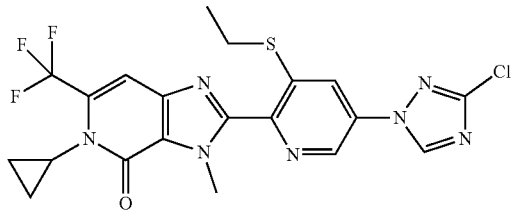

A33

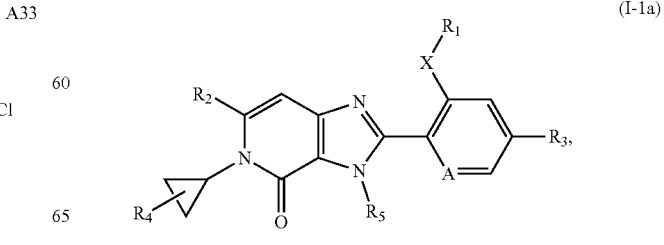

(I-1a)

TABLE A

| Comp. No. | X | R₁ | R₃ | A | R₂ | R₄ | R₅ | Analytical data |
|---|---|---|---|---|---|---|---|---|
| A1 (1.004) | SO$_2$ | CH$_2$CH$_3$ | CF$_3$ | N | CF$_3$ | H | CH$_3$ | See preparatory examples |
| A2 (1.019) | S | CH$_2$CH$_3$ | 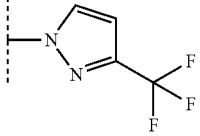 | N | CF$_3$ | H | CH$_3$ | See preparatory examples |
| A3 (1.020) | SO$_2$ | CH$_2$CH$_3$ | 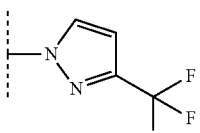 | N | CF$_3$ | H | CH$_3$ | See preparatory examples |
| A4 | S | CH$_2$CH$_3$ | Br | N | CF$_3$ | H | CH$_3$ | See preparatory examples |
| A5 | SO$_2$ | CH$_2$CH$_3$ | Br | N | CF$_3$ | H | CH$_3$ | Prepared as described in Example P3 from A4: ¹H NMR (400 MHz, CDCl$_3$) δ ppm: 9.01 (d, 1 H); 8.62 (d, 1 H); 7.17 (s, 1H); 4.04 (s, 3H); 3.80 (q, 2H); 3.10 (m, 1H), 1.36 (t, 3H), 1.28 (m, 2H), 1.06 (m, 2H). |
| A6 (1.010) | SO$_2$ | CH$_2$CH$_3$ | 3,5-diF—Ph | N | CF$_3$ | H | CH$_3$ | See preparatory examples |
| A7 | SO$_2$ | CH$_2$CH$_3$ | 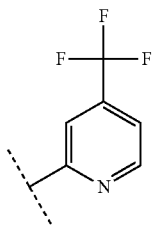 | N | CF$_3$ | H | CH$_3$ | See preparatory examples |
| A8 (1.006) | SO$_2$ | CH$_2$CH$_3$ | 4-Cl—Ph | N | CF$_3$ | H | CH$_3$ | Prepared as described in Example P5 from A5: : LC-MS (Method A) RT 1.19, 537 (MH+) |
| A9 (1.008) | SO$_2$ | CH$_2$CH$_3$ | 3-CF$_3$Ph | N | CF$_3$ | H | CH$_3$ | Prepared as described in Example P5 from A5: LC-MS (Method A) RT 1.20, 571 (MH+) |
| A10 | SO$_2$ | CH$_2$CH$_3$ | 3,5-di(CF$_3$)—Ph | N | CF$_3$ | H | CH$_3$ | See preparatory examples |
| A11 | SO$_2$ | CH$_2$CH$_3$ | 4-F—Ph | N | CF$_3$ | H | CH$_3$ | See preparatory examples |
| A12 | SO$_2$ | CH$_2$CH$_3$ | (6-OMe)-pyrimidin-3yl | N | CF$_3$ | H | CH$_3$ | See preparatory examples |
| A13 | SO$_2$ | CH$_2$CH$_3$ | pyrimidin-3yl | N | CF$_3$ | H | CH$_3$ | See preparatory examples |
| A14 | SO$_2$ | CH$_2$CH$_3$ | 4-pyridinyl | N | CF$_3$ | H | CH$_3$ | See preparatory examples |
| A15 | SO$_2$ | CH$_2$CH$_3$ | 3-(OCF$_3$)Ph | N | CF$_3$ | H | CH$_3$ | See preparatory examples |
| A16 | SO$_2$ | CH$_2$CH$_3$ | 3-(SCH$_3$)Ph | N | CF$_3$ | H | CH$_3$ | See preparatory examples |
| A17 | SO$_2$ | CH$_2$CH$_3$ | 2-CF$_3$Ph | N | CF$_3$ | H | CH$_3$ | See preparatory examples |
| A18 | SO$_2$ | CH$_2$CH$_3$ | 4,3-di-Cl—Ph | N | CF$_3$ | H | CH$_3$ | See preparatory examples |
| A19 | SO$_2$ | CH$_2$CH$_3$ | 4,2-di-Cl—Ph | N | CF$_3$ | H | CH$_3$ | See preparatory examples |
| A20 | SO$_2$ | CH$_2$CH$_3$ | 4-MeO, 3-F—Ph | N | CF$_3$ | H | CH$_3$ | See preparatory examples |
| A21 | SO$_2$ | CH$_2$CH$_3$ | 4-CF$_3$-pyridin-3-yl | N | CF$_3$ | H | CH$_3$ | See preparatory examples |
| A22 | SO$_2$ | CH$_2$CH$_3$ | 3-F—Ph | N | CF$_3$ | H | CH$_3$ | See preparatory examples |
| A23 | SO$_2$ | CH$_2$CH$_3$ | 4-(OCF$_3$)Ph | N | CF$_3$ | H | CH$_3$ | See preparatory examples |
| A24 | SO$_2$ | CH$_2$CH$_3$ | 4,3-di-F—Ph | N | CF$_3$ | H | CH$_3$ | See preparatory examples |
| A25 | SO$_2$ | CH$_2$CH$_3$ | 5,4,3-tri-F—Ph | N | CF$_3$ | H | CH$_3$ | See preparatory examples |
| A26 | SO$_2$ | CH$_2$CH$_3$ | 5,2-di-F—Ph | N | CF$_3$ | H | CH$_3$ | See preparatory examples |
| A27 | SO$_2$ | CH$_2$CH$_3$ | 4-CF$_3$, 2-F—Ph | N | CF$_3$ | H | CH$_3$ | See preparatory examples |
| A28 | SO$_2$ | CH$_2$CH$_3$ | 5-F,3-Cl—Ph | N | CF$_3$ | H | CH$_3$ | See preparatory examples |
| A29 | SO$_2$ | CH$_2$CH$_3$ | Ph | N | CF$_3$ | H | CH$_3$ | See preparatory examples |
| A30 (1.014) | SO$_2$ | CH$_2$CH$_3$ | pyrimidin-2-yl | N | CF$_3$ | H | CH$_3$ | Prepared as described in Example P6: LC-MS (Method A) RT 1.01, 505 (MH+) |
| A31 (1.012) | SO$_2$ | CH$_2$CH$_3$ | 1-cyclopropane-carbonitrile | N | CF$_3$ | H | CH$_3$ | See preparatory examples. |

TABLE A-continued

| Comp. No. | X | R₁ | R₃ | A | R₂ | R₄ | R₅ | Analytical data |
|---|---|---|---|---|---|---|---|---|
| A32 (1.002) | SO₂ | CH₂CH₃ | H | N | CF₃ | H | CH₃ | Prepared using methods described in preparatory examples: LC-MS (Method A) RT 0.91, 427 (MH+) |
| A33 | SO | CH₂CH₃ | 3-chloro-1,2,4-triazole-1-yl | N | CF₃ | H | CH₃ | See preparatory examples. |
| A34 | SO₂ | CH₂CH₃ | 3-chloro-1,2,4-triazole-1-yl | N | CF₃ | H | CH₃ | See preparatory examples. |
| A35 | S | CH₂CH₃ |  | N | CF₃ | H | CH₃ | Prepared by analogy with Example P9, Step A: LC-MS (Method A) RT 1.05, 486 (MH+). |
| A36 | SO₂ | CH₂CH₃ | 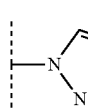 | N | CF₃ | H | CH₃ | Prepared by analogy with Example P3 (via oxidation of the sulfur of A35) : LC-MS (Method A) RT 1.01, 517 (MH+). |
| A37 | SO₂ | CH₂CH₃ | 3-CH₃S—5-CF₃Ph | N | CF₃ | H | CH₃ | Prepared by analogy with Example P5 (from A5): LC-MS (Method A) RT 1.23, 617 (MH+) |
| A38 | SO₂ | CH₂CH₃ | 3,5-di-Cl—4-F—Ph | N | CF₃ | H | CH₃ | Prepared by analogy with Example P5 (from A5): ¹H NMR (400 MHz, CDCl₃) δ ppm: 9.12 (s, 1 H); 8.58 (s, 1 H); 7.66 (m, 2H); 7.18(s, 1H); 4.08 (s, 3H), 3.84 (q, 2H); 3.12 (m, 1H), 1.38 (t, 3H), 1.28 (m, 2H), 1.06 (m, 2H). |
| A39 | SO₂ | CH₂CH₃ | 4-F-pyridine-2-yl | N | CF₃ | H | CH₃ | A39 was synthesised by analogy with protocols described before. LC-MS (Method A) RT 1.07, 522 (MH+) |
| A40 | SO₂ | CH₂CH₃ | 5-F-pyridine-3-yl | N | CF₃ | H | CH₃ | A40 was synthesised by analogy with protocols described before. LC-MS (Method A) RT 1.00, 522 (MH+) |
| A41 | SO₂ | CH₂CH₃ | 6-F-pyridine-2-yl | N | CF₃ | H | CH₃ | A41 was synthesised by analogy with protocols described before. LC-MS (Method A) RT 1.08, 522 (MH+) |
| A42 | SO₂ | CH₂CH₃ | cyclopropyl | N | CF₃ | H | CH₃ | A42 was synthesised by analogy with protocols described before. LC-MS (Method A) RT 1.03, 467 (MH+) |
| A43 | SO₂ | CH₂CH₃ | H | C | CF₃ | H | CH₃ | A43 was prepared using, by analogy protocols described before and the commercially available 2-(Ethylsulfonyl)benzoic acid (CAS: 161058-27-1). LC-MS (Method A) RT 0.93, 426 (MH+) |

The activity of the compositions according to the invention can be broadened considerably, and adapted to prevailing circumstances, by adding other insecticidally, acaricidally and/or fungicidally active ingredients. The mixtures of the compounds of formula I with other insecticidally, acaricidally and/or fungicidally active ingredients may also have further surprising advantages which can also be described, in a wider sense, as synergistic activity. For example, better tolerance by plants, reduced phytotoxicity, insects can be controlled in their different development stages or better behaviour during their production, for example during grinding or mixing, during their storage or during their use.

Suitable additions to active ingredients here are, for example, representatives of the following classes of active ingredients: organophosphorus compounds, nitrophenol derivatives, thioureas, juvenile hormones, formamidines, benzophenone derivatives, ureas, pyrrole derivatives, carbamates, pyrethroids, chlorinated hydrocarbons, acylureas, pyridylmethyleneamino derivatives, macrolides, neonicotinoids and *Bacillus thuringiensis* preparations.

The following mixtures of the compounds of formula I with active ingredients are preferred (the abbreviation "TX" means "one compound selected from the group consisting of the compounds described in Table 1 and A of the present invention"):

an adjuvant selected from the group of substances consisting of petroleum oils (628)+TX, an acaricide selected from the group of substances consisting of 1,1-bis(4-chlorophenyl)-2-ethoxyethanol (IUPAC name) (910)+TX, 2,4-dichlorophenyl benzenesulfonate (IUPAC/Chemical Abstracts name) (1059)+TX, 2-fluoro-N-methyl-N-1-naphthylacetamide (IUPAC name) (1295)+TX, 4-chlorophenyl phenyl sulfone (IUPAC name) (981)+TX, abamectin (1)+TX, acequinocyl (3)+TX, acetoprole [CCN]+TX, acrinathrin (9)+TX, aldicarb (16)+TX, aldoxycarb (863)+TX, alpha-cypermethrin (202)+TX, amidithion (870)+TX, amidoflumet [CCN]+TX, amidothioate (872)+TX, amiton (875)+TX, amiton hydrogen oxalate (875)+TX, amitraz (24)+TX, aramite (881)+TX, arsenous oxide (882)+TX, AVI 382 (compound code)+TX, AZ 60541 (compound code)+TX, azinphos-ethyl (44)+TX, azinphos-methyl (45)+TX, azobenzene (IUPAC name) (888)+TX, azocyclotin (46)+TX, azothoate (889)+TX, benomyl (62)+TX, benoxafos [CCN]+TX, benzoximate (71)+TX, benzyl benzoate (IUPAC name) [CCN]+TX, bifenazate (74)+TX, bifenthrin (76)+TX, binapacryl (907)+TX, brofenvalerate+TX, bromocyclen (918)+TX, bromophos (920)+TX, bromophos-ethyl (921)+TX, bromopropylate (94)+TX, buprofezin (99)+TX, butocarboxim (103)+TX, butoxycarboxim (104)+TX, butylpyridaben+TX, calcium polysulfide (IUPAC name) (111)+TX, camphechlor (941)+TX, carbanolate (943)+TX, carbaryl (115)+TX, carbofuran (118)+TX, carbophenothion (947)+TX, CGA 50'439 (development code) (125)+TX, chinomethionat (126)+TX, chlorbenside (959)+TX, chlordimeform (964)+TX, chlordimeform hydrochloride (964)+TX, chlorfenapyr (130)+TX, chlorfenethol (968)+TX, chlorfenson (970)+TX, chlorfensulfide (971)+TX, chlorfenvinphos (131)+TX, chlorobenzilate (975)+TX, chloromebuform (977)+TX, chloromethiuron (978)+TX, chloropropylate (983)+TX, chlorpyrifos (145)+TX, chlorpyrifos-methyl (146)+TX, chlorthiophos (994)+TX, cinerin I (696)+TX, cinerin II (696)+TX, cinerins (696)+TX, clofentezine (158)+TX, closantel [CCN]+TX, coumaphos (174)+TX, crotamiton [CCN]+TX, crotoxyphos (1010)+TX, cufraneb (1013)+TX, cyanthoate (1020)+TX, cyflumetofen (CAS Reg. No.: 400882-07-7)+TX, cyhalothrin (196)+TX, cyhexatin (199)+TX, cypermethrin (201)+TX, DCPM (1032)+TX, DDT (219)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulfon (1039)+TX, diafenthiuron (226)+TX, dialifos (1042)+TX, diazinon (227)+TX, dichlofluanid (230)+TX, dichlorvos (236)+TX, dicliphos+TX, dicofol (242)+TX, dicrotophos (243)+TX, dienochlor (1071)+TX, dimefox (1081)+TX, dimethoate (262)+TX, dinactin (653)+TX, dinex (1089)+TX, dinex-diclexine (1089)+TX, dinobuton (269)+TX, dinocap (270)+TX, dinocap-4 [CCN]+TX, dinocap-6 [CCN]+TX, dinocton (1090)+TX, dinopenton (1092)+TX, dinosulfon (1097)+TX, dinoterbon (1098)+TX, dioxathion (1102)+TX, diphenyl sulfone (IUPAC name) (1103)+TX, disulfiram [CCN]+TX, disulfoton (278)+TX, DNOC (282)+TX, dofenapyn (1113)+TX, doramectin [CCN]+TX, endosulfan (294)+TX, endothion (1121)+TX, EPN (297)+TX, eprinomectin [CCN]+TX, ethion (309)+TX, ethoate-methyl (1134)+TX, etoxazole (320)+TX, etrimfos (1142)+TX, fenazaflor (1147)+TX, fenazaquin (328)+TX, fenbutatin oxide (330)+TX, fenothiocarb (337)+TX, fenpropathrin (342)+TX, fenpyrad+TX, fenpyroximate (345)+TX, fenson (1157)+TX, fentrifanil (1161)+TX, fenvalerate (349)+TX, fipronil (354)+TX, fluacry-pyrim (360)+TX, fluazuron (1166)+TX, flubenzimine (1167)+TX, flucycloxuron (366)+TX, flucythrinate (367)+TX, fluenetil (1169)+TX, flufenoxuron (370)+TX, flumethrin (372)+TX, fluorbenside (1174)+TX, fluvalinate (1184)+TX, FMC 1137 (development code) (1185)+TX, formetanate (405)+TX, formetanate hydrochloride (405)+TX, formothion (1192)+TX, formparanate (1193)+TX, gamma-HCH (430)+TX, glyodin (1205)+TX, halfenprox (424)+TX, heptenophos (432)+TX, hexadecyl cyclopropanecarboxylate (IUPAC/Chemical Abstracts name) (1216)+TX, hexythiazox (441)+TX, iodomethane (IUPAC name) (542)+TX, isocarbophos (473)+TX, isopropyl O-(methoxyaminothiophosphoryl)salicylate (IUPAC name) (473)+TX, ivermectin [CCN]+TX, jasmolin I (696)+TX, jasmolin II (696)+TX, jodfenphos (1248)+TX, lindane (430)+TX, lufenuron (490)+TX, malathion (492)+TX, malonoben (1254)+TX, mecarbam (502)+TX, mephosfolan (1261)+TX, mesulfen [CCN]+TX, methacrifos (1266)+TX, methamidophos (527)+TX, methidathion (529)+TX, methiocarb (530)+TX, methomyl (531)+TX, methyl bromide (537)+TX, metolcarb (550)+TX, mevinphos (556)+TX, mexacarbate (1290)+TX, milbemectin (557)+TX, milbemycin oxime [CCN]+TX, mipafox (1293)+TX, monocrotophos (561)+TX, morphothion (1300)+TX, moxidectin [CCN]+TX, naled (567)+TX, NC-184 (compound code)+TX, NC-512 (compound code)+TX, nifluridide (1309)+TX, nikkomycins [CCN]+TX, nitrilacarb (1313)+TX, nitrilacarb 1:1 zinc chloride complex (1313)+TX, NNI-0101 (compound code)+TX, NNI-0250 (compound code)+TX, omethoate (594)+TX, oxamyl (602)+TX, oxydeprofos (1324)+TX, oxydisulfoton (1325)+TX, pp'-DDT (219)+TX, parathion (615)+TX, permethrin (626)+TX, petroleum oils (628)+TX, phenkapton (1330)+TX, phenthoate (631)+TX, phorate (636)+TX, phosalone (637)+TX, phosfolan (1338)+TX, phosmet (638)+TX, phosphamidon (639)+TX, phoxim (642)+TX, pirimiphos-methyl (652)+TX, polychloroterpenes (traditional name) (1347)+TX, polynactins (653)+TX, proclonol (1350)+TX, profenofos (662)+TX, promacyl (1354)+TX, propargite (671)+TX, propetamphos (673)+TX, propoxur (678)+TX, prothidathion (1360)+TX, prothoate (1362)+TX, pyrethrin I (696)+TX, pyrethrin II (696)+TX, pyrethrins (696)+TX, pyridaben (699)+TX, pyridaphenthion (701)+TX, pyrimidifen (706)+TX, pyrimitate (1370)+TX, quinalphos (711)+TX, quintiofos (1381)+TX, R-1492 (development code) (1382)+TX, RA-17 (development code) (1383)+TX, rotenone (722)+TX, schradan (1389)+TX, sebufos+TX, selamectin [CCN]+TX, SI-0009 (compound code)+TX, sophamide (1402)+TX, spirodiclofen (738)+TX, spiromesifen (739)+TX, SSI-121 (development code) (1404)+TX, sulfiram [CCN]+TX, sulfluramid (750)+TX, sulfotep (753)+TX, sulfur (754)+TX, SZI-121 (development code) (757)+TX, tau-fluvalinate (398)+TX, tebufenpyrad (763)+TX, TEPP (1417)+TX, terbam+TX, tetrachlorvinphos (777)+TX, tetradifon (786)+TX, tetranactin (653)+TX, tetrasul (1425)+TX, thiafenox+TX, thiocarboxime (1431)+TX, thiofanox (800)+TX, thiometon (801)+TX, thioquinox (1436)+TX, thuringiensin [CCN]+TX, triamiphos (1441)+TX, triarathene (1443)+TX, triazophos (820)+TX, triazuron+TX, trichlorfon (824)+TX, trifenofos (1455)+TX, trinactin (653)+TX, vamidothion (847)+TX, vaniliprole [CCN] and YI-5302 (compound code)+TX, an algicide selected from the group of substances consisting of bethoxazin [CCN]+TX, copper dioctanoate (IUPAC name) (170)+TX, copper sulfate (172)+TX, cybutryne [CCN]+TX, dichlone (1052)+TX, dichlorophen (232)+TX, endothal (295)+TX, fentin (347)+TX, hydrated lime [CCN]+TX, nabam (566)+TX, quinoclamine (714)+TX, quinonamid (1379)+TX, simazine (730)+TX, triphenyltin acetate (IUPAC name) (347) and triphenyltin hydroxide (IUPAC name) (347)+TX, an anthelmintic selected from the group of substances consisting of abamectin (1)+TX, crufomate (1011)+TX, doramectin [CCN]+TX, emamectin (291)+TX, emamectin benzoate (291)+TX, eprinomectin [CCN]+TX, ivermectin [CCN]+TX, milbemycin oxime [CCN]+TX, moxidectin [CCN]+TX, piperazine [CCN]+TX, selamectin [CCN]+TX, spinosad (737) and thiophanate (1435)+TX, an avicide selected from the group of substances consisting of chloralose (127)+TX, endrin (1122)+TX, fenthion (346)+TX, pyridin-4-amine (IUPAC name) (23) and strychnine (745)+TX, a bactericide selected from the group of substances consisting of 1-hydroxy-1H-pyridine-2-thione (IUPAC name) (1222)+TX, 4-(quinoxalin-2-ylamino)benzenesulfonamide (IUPAC name) (748)+TX, 8-hydroxyquinoline sulfate (446)+TX, bronopol (97)+TX, copper dioctanoate (IUPAC name) (170)+TX, copper hydroxide (IUPAC name) (169)+TX, cresol [CCN]+TX, dichlorophen (232)+TX, dipyrithione (1105)+TX, dodicin (1112)+TX, fenaminosulf (1144)+TX, formaldehyde (404)+TX, hydrargaphen [CCN]+TX, kasugamycin (483)+TX, kasugamycin hydrochloride hydrate (483)+TX, nickel bis(dimethyldithiocarbamate) (IUPAC name) (1308)+TX, nitrapyrin (580)+TX, octhilinone (590)+TX, oxolinic acid (606)+TX, oxytetracycline (611)+TX, potassium hydroxyquinoline sulfate (446)+TX, probenazole (658)+TX, streptomycin (744)+TX, streptomycin sesquisulfate (744)+TX, tecloftalam (766)+TX, and thiomersal [CCN]+TX, a biological agent selected from the group of substances consisting of *Adoxophyes orana* GV (12)+TX, *Agrobacterium radiobacter* (13)+TX, *Amblyseius* spp. (19)+TX, *Anagrapha falcifera* NPV (28)+TX, *Anagrus atomus* (29)+TX, *Aphelinus abdominalis* (33)+TX, *Aphidius colemani* (34)+TX, *Aphidoletes aphidimyza* (35)+TX, *Autographa californica* NPV (38)+TX, *Bacillus firmus* (48)+TX, *Bacillus sphaericus* Neide (scientific name) (49)+TX, *Bacillus thuringiensis* Berliner (scientific name) (51)+TX, *Bacillus thuringiensis* subsp. *aizawai* (scientific name) (51)+TX, *Bacillus thuringiensis* subsp. *israelensis* (scientific name) (51)+TX, *Bacillus thuringiensis* subsp. *japonensis* (scientific name) (51)+TX, *Bacillus thuringiensis* subsp. *kurstaki* (scientific name) (51)+TX, *Bacillus thuringiensis* subsp. *tenebrionis* (scientific name) (51)+TX, *Beauveria bassiana* (53)+TX, *Beauveria brongniartii* (54)+TX, *Chrysoperla carnea* (151)+TX, *Cryptolaemus montrouzieri* (178)+TX, *Cydia pomonella* GV (191)+TX, *Dacnusa sibirica* (212)+TX, *Diglyphus isaea* (254)+TX, *Encarsia formosa* (scientific name) (293)+TX, *Eretmocerus eremicus* (300)+TX, *Helicoverpa zea* NPV (431)+TX, *Heterorhabditis bacteriophora* and *H. megidis* (433)+TX, *Hippodamia convergens* (442)+TX, *Leptomastix dactylopii* (488)+TX, *Macrolophus caliginosus* (491)+TX, *Mamestra brassicae* NPV (494)+TX, *Metaphycus helvolus* (522)+TX, *Metarhizium anisopliae* var. *acridum* (scientific name) (523)+TX, *Metarhizium anisopliae* var. *anisopliae* (scientific name) (523)+TX, *Neodiprion sertifer* NPV and *N. lecontei* NPV (575)+TX, *Orius* spp. (596)+TX, *Paecilomyces fumosoroseus* (613)+TX, *Phytoseiulus persimilis* (644)+TX, *Spodoptera exigua* multicapsid nuclear polyhedrosis virus (scientific name) (741)+TX, *Steinemema bibionis* (742)+TX, *Steinemema carpocapsae* (742)+TX, *Steinemema feltiae* (742)+TX, *Steinemema glaseri* (742)+TX, *Steinemema riobrave* (742)+TX, *Steinemema riobravis* (742)+TX, *Steinemema scapterisci* (742)+TX, *Steinemema* spp. (742)+TX, *Trichogramma* spp. (826)+TX, *Typhlodromus occidentalis* (844) and *Verticillium lecanii* (848)+TX, a soil sterilant selected from the group of substances consisting of iodomethane (IUPAC name) (542) and methyl bromide (537)+TX, a chemosterilant selected from the group of substances consisting of apholate [CCN]+TX, bisazir [CCN]+TX, busulfan [CCN]+TX, diflubenzuron (250)+TX, dimatif [CCN]+TX, hemel [CCN]+TX, hempa [CCN]+TX, metepa [CCN]+TX, methiotepa [CCN]+TX, methyl apholate [CCN]+TX, morzid [CCN]+TX, penfluron [CCN]+TX, tepa [CCN]+TX, thiohempa [CCN]+TX, thiotepa [CCN]+TX, tretamine [CCN] and uredepa [CCN]+TX, an insect pheromone selected from the group of substances consisting of (E)-dec-5-en-1-yl acetate with (E)-dec-5-en-1-ol (IUPAC name) (222)+TX, (E)-tridec-4-en-1-yl acetate (IUPAC name) (829)+TX, (E)-6-methylhept-2-en-4-ol (IUPAC name) (541)+TX, (E,Z)-tetradeca-4,10-dien-1-yl acetate (IUPAC name) (779)+TX, (Z)-dodec-7-en-1-yl acetate (IUPAC name) (285)+TX, (Z)-hexadec-11-enal (IUPAC name) (436)+TX, (Z)-hexadec-11-en-1-yl acetate (IUPAC name) (437)+TX, (Z)-hexadec-13-en-11-yn-1-yl acetate (IUPAC name) (438)+TX, (Z)-icos-13-en-10-one (IUPAC name) (448)+TX, (Z)-tetradec-7-en-1-al (IUPAC name) (782)+TX, (Z)-tetradec-9-en-1-ol (IUPAC name) (783) +TX, (Z)-tetradec-9-en-1-yl acetate (IUPAC name) (784)+TX, (7E,9Z)-dodeca-7,9-dien-1-yl acetate (IUPAC name) (283)+TX, (9Z,11E)-tetradeca-9,11-dien-1-yl acetate (IUPAC name) (780)+TX, (9Z,12E)-tetradeca-9,12-dien-1-yl acetate (IUPAC name) (781)+TX, 14-methyloctadec-1-ene (IUPAC name) (545)+TX, 4-methylnonan-5-ol with 4-methylnonan-5-one (IUPAC name) (544)+TX, alpha-multistriatin [CCN]+TX, brevicomin [CCN]+TX, codlelure [CCN]+TX, codlemone (167)+TX, cuelure (179)+TX, disparlure (277)+TX, dodec-8-en-1-yl acetate (IUPAC name) (286)+TX, dodec-9-en-1-yl acetate (IUPAC name) (287)+TX, dodeca-8+TX, 10-dien-1-yl acetate (IUPAC name) (284)+TX, dominicalure [CCN]+TX, ethyl 4-methyloctanoate (IUPAC name) (317)+TX, eugenol [CCN]+TX, frontalin [CCN]+TX, gossyplure (420)+TX, grandlure (421)+TX, grandlure I (421)+TX, grandlure II (421)+TX, grandlure III (421)+TX, grandlure IV (421)+TX, hexalure [CCN]+TX, ipsdienol [CCN]+TX, ipsenol [CCN]+TX, japonilure (481)+TX, lineatin [CCN]+TX, litlure [CCN]+TX, looplure [CCN]+TX, medlure [CCN]+TX, megatomoic acid [CCN]+TX, methyl eugenol (540)+TX, muscalure (563)+TX, octadeca-2,13-dien-1-yl acetate (IUPAC name) (588)+TX, octadeca-3,13-dien-1-yl acetate (IUPAC name) (589)+TX, orfralure [CCN]+TX, oryctalure (317)+TX, ostramone [CCN]+TX, siglure [CCN]+TX, sordidin (736)+TX, sulcatol [CCN]+TX, tetradec-11-en-1-yl acetate (IUPAC name) (785)+TX, trimedlure (839)+TX, trimedlure A (839)+TX, trimedlure B$_1$ (839)+TX, trimedlure B$_2$ (839)+TX, trimedlure C (839) and trunc-call [CCN]+TX, an insect repellent selected from the group of substances consisting of 2-(octylthio)ethanol (IUPAC name) (591)+TX, butopyronoxyl (933)+TX, butoxy(polypropylene glycol) (936)+TX, dibutyl adipate (IUPAC name) (1046)+TX, dibutyl phthalate (1047)+TX, dibutyl succinate (IUPAC name) (1048)+TX, diethyltoluamide [CCN]+TX, dimethyl carbate [CCN]+TX, dimethyl phthalate [CCN]+TX, ethyl hexanediol (1137)+TX, hexamide [CCN]+TX, methoquin-butyl (1276)+TX, methylneodecanamide [CCN]+TX, oxamate [CCN] and picaridin [CCN]+TX, an insecticide selected from the group of substances consisting of 1-dichloro-1-nitroethane (IUPAC/Chemical Abstracts name) (1058)+TX, 1,1-dichloro-2,2-bis(4-ethylphenyl)ethane (IUPAC name) (1056),+TX, 1,2-dichloropropane (IUPAC/Chemical Abstracts name) (1062)+TX, 1,2-dichloropropane with 1,3-dichloropropene (IUPAC name) (1063)+TX, 1-bromo-2-chloroethane (IUPAC/Chemical Abstracts name) (916)+TX, 2,2,2-trichloro-1-(3,4-dichlorophenyl)ethyl acetate (IUPAC name) (1451)+TX, 2,2-dichlorovinyl 2-ethylsulfinylethyl methyl phosphate (IUPAC name) (1066)+TX, 2-(1,3-dithiolan-2-yl)phenyl dimethylcarbamate (IUPAC/Chemical Abstracts name) (1109)+TX, 2-(2-butoxyethoxy)ethyl thiocyanate (IUPAC/Chemical Abstracts name) (935)+TX, 2-(4,5-dimethyl-1,3-dioxolan-2-yl)phenyl methylcarbamate (IUPAC/Chemical Abstracts name) (1084)+TX, 2-(4-chloro-3,5-xylyloxy)ethanol (IUPAC name) (986)+TX, 2-chlorovinyl diethyl phosphate (IUPAC name) (984)+TX, 2-imidazolidone (IUPAC name) (1225)+TX, 2-isovalerylindan-1,3-dione (IUPAC name) (1246)+TX, 2-methyl(prop-2-ynyl)aminophenyl methylcarbamate (IUPAC name) (1284)+TX, 2-thiocyanatoethyl laurate (IUPAC name) (1433)+TX, 3-bromo-1-chloroprop-1-ene (IUPAC name) (917)+TX, 3-methyl-1-phenylpyrazol-5-yl dimethylcarbamate (IUPAC name) (1283)+TX, 4-methyl(prop-2-ynyl)amino-3,5-xylyl methylcarbamate (IUPAC name) (1285)+TX, 5,5-dimethyl-3-oxocyclohex-1-enyl dimethylcarbamate (IUPAC name) (1085)+TX, abamectin (1)+TX, acephate (2)+TX, acetamiprid (4)+TX, acethion [CCN]+TX, acetoprole [CCN]+TX, acrinathrin (9)+TX, acrylonitrile (IUPAC name) (861)+TX, alanycarb (15)+TX, aldicarb (16)+TX, aldoxycarb (863)+TX, aldrin (864)+TX, allethrin (17)+TX, allosamidin [CCN]+TX, allyxycarb (866)+TX, alpha-cypermethrin (202)+TX, alpha-ecdysone [CCN]+TX, aluminium phosphide (640)+TX, amidithion (870)+TX, amidothioate (872)+TX, aminocarb (873)+TX, amiton (875)+TX, amiton hydrogen oxalate (875)+TX, amitraz (24)+TX, anabasine (877)+TX, athidathion (883)+TX, AVI 382 (compound code)+TX, AZ 60541 (compound code)+TX, azadirachtin (41)+TX, azamethiphos (42)+TX, azinphos-ethyl (44)+TX, azinphos-methyl (45)+TX, azothoate (889)+TX, *Bacillus thuringiensis* delta endotoxins (52)+TX, barium hexafluorosilicate [CCN]+TX, barium polysulfide (IUPAC/Chemical Abstracts name) (892)+TX, barthrin [CCN]+TX, Bayer 22/190 (development code) (893)+TX, Bayer 22408 (development code) (894)+TX, bendiocarb (58)+TX, benfuracarb (60)+TX, bensultap (66)+TX, beta-cyfluthrin (194)+TX, beta-cypermethrin (203)+TX, bifenthrin (76)+TX, bioallethrin (78)+TX, bioallethrin S-cyclopentenyl isomer (79)+TX, bioethanomethrin [CCN]+TX, biopermethrin (908)+TX, bioresmethrin (80)+TX, bis(2-chloroethyl) ether (IUPAC name) (909)+TX, bistrifluron (83)+TX, borax (86)+TX, brofenvalerate+TX, bromfenvinfos (914)+TX, bromocyclen (918)+TX, bromo-DDT [CCN]+TX, bromophos (920)+TX, bromophos-ethyl (921)+TX, bufencarb (924)+TX, buprofezin (99)+TX, butacarb (926)+TX, butathiofos (927)+TX, butocarboxim (103)+TX, butonate (932)+TX, butoxycarboxim (104)+TX, butylpyridaben+TX, cadusafos (109)+TX, calcium arsenate [CCN]+TX, calcium cyanide (444)+TX, calcium polysulfide (IUPAC name) (111)+TX, camphechlor (941)+TX, carbanolate (943)+TX, carbaryl (115)+TX, carbofuran (118)+TX, carbon disulfide (IUPAC/Chemical Abstracts name) (945)+TX, carbon tetrachloride (IUPAC name) (946)+TX, carbophenothion (947)+TX, carbosulfan (119)+TX, cartap (123)+TX, cartap hydrochloride (123)+TX, cevadine (725)+TX, chlorbicyclen (960)+TX, chlordane (128)+TX, chlordecone (963)+TX, chlordimeform (964)+TX, chlordimeform hydrochloride (964)+TX, chlorethoxyfos (129)+TX, chlorfenapyr (130)+TX, chlorfenvinphos (131)+TX, chlorfluazuron (132)+TX, chlormephos (136)+TX, chloroform [CCN]+TX, chloropicrin (141)+TX, chlorphoxim (989)+TX, chlorprazophos (990)+TX, chlorpyrifos (145)+TX, chlorpyrifos-methyl (146)+TX, chlorthiophos (994)+TX, chromafenozide (150)+TX, cinerin I (696)+TX, cinerin II (696)+TX, cinerins (696)+TX, cis-resmethrin+TX, cismethrin (80)+TX, clocythrin+TX, cloethocarb (999)+TX, closantel [CCN]+TX, clothianidin (165)+TX, copper acetoarsenite [CCN]+TX, copper arsenate [CCN]+TX, copper oleate [CCN]+TX, coumaphos (174)+TX, coumithoate (1006)+TX, crotamiton [CCN]+TX, crotoxyphos (1010)+TX, crufomate (1011)+TX, cryolite (177)+TX, CS 708 (development code) (1012)+TX, cyanofenphos (1019)+TX, cyanophos (184)+TX, cyanthoate (1020)+TX, cyclethrin [CCN]+TX, cycloprothrin (188)+TX, cyfluthrin (193)+TX, cyhalothrin (196)+TX, cypermethrin (201)+TX, cyphenothrin (206)+TX, cyromazine (209)+TX, cythioate [CCN]+TX, d-limonene [CCN]+TX, d-tetramethrin (788)+TX, DAEP (1031)+TX, dazomet (216)+TX, DDT (219)+TX, decarbofuran (1034)+TX, deltamethrin (223)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulphon (1039)+TX, diafenthiuron (226)+TX, dialifos (1042)+TX, diamidafos (1044)+TX, diazinon (227)+TX, dicapthon (1050)+TX, dichlofenthion (1051)+TX, dichlorvos (236)+TX, dicliphos+TX, dicresyl [CCN]+TX, dicrotophos (243)+TX, dicyclanil (244)+TX, dieldrin (1070)+TX, diethyl 5-methylpyrazol-3-yl phosphate (IUPAC name) (1076)+TX, diflubenzuron (250)+TX, dilor [CCN]+TX, dimefluthrin [CCN]+TX, dimefox (1081)+TX, dimetan (1085)+TX, dimethoate (262)+TX, dimethrin (1083)+TX, dimethylvinphos (265)+TX, dimetilan (1086)+TX, dinex (1089)+TX, dinex-diclexine (1089)+TX, dinoprop (1093)+TX, dinosam (1094)+TX, dinoseb (1095)+TX, dinotefuran (271)+TX, diofenolan (1099)+TX, dioxabenzofos (1100)+TX, dioxacarb (1101)+TX, dioxathion (1102)+TX, disulfoton (278)+TX, dithicrofos (1108)+TX, DNOC (282)+TX, doramectin [CCN]+TX, DSP (1115)+TX, ecdysterone [CCN]+TX, EI 1642 (development code) (1118)+TX, emamectin (291)+TX, emamectin benzoate (291)+TX, EMPC (1120)+TX, empenthrin (292)+TX, endosulfan (294)+TX, endothion (1121)+TX, endrin (1122)+TX, EPBP (1123)+TX, EPN (297)+TX, epofenonane (1124)+TX, eprinomectin [CCN]+TX, esfenvalerate (302)+TX, etaphos [CCN]+TX, ethiofencarb (308)+TX, ethion (309)+TX, ethiprole (310)+TX, ethoatemethyl (1134)+TX, ethoprophos (312)+TX, ethyl formate (IUPAC name) [CCN]+TX, ethyl-DDD (1056)+TX, ethylene dibromide (316)+TX, ethylene dichloride (chemical name) (1136)+TX, ethylene oxide [CCN]+TX, etofenprox (319)+TX, etrimfos (1142)+TX, EXD (1143)+TX, famphur (323)+TX, fenamiphos (326)+TX, fenazaflor (1147)+TX, fenchlorphos (1148)+TX, fenethacarb (1149)+TX, fenfluthrin (1150)+TX, fenitrothion (335)+TX, fenobucarb (336)+TX, fenoxacrim (1153)+TX, fenoxycarb (340)+TX, fenpirithrin (1155)+TX, fenpropathrin (342)+TX, fenpyrad+TX, fensulfothion (1158)+TX, fenthion (346)+TX, fenthionethyl [CCN]+TX, fenvalerate (349)+TX, fipronil (354)+TX, flonicamid (358)+TX, flubendiamide (CAS. Reg. No.: 272451-65-7)+TX, flucofuron (1168)+TX, flucycloxuron (366)+TX, flucythrinate (367)+TX, fluenetil (1169)+TX, flufenerim [CCN]+TX, flufenoxuron (370)+TX, flufenprox (1171)+TX, flumethrin (372)+TX, fluvalinate (1184)+TX, FMC 1137 (development code) (1185)+TX, fonofos (1191)+TX, formetanate (405)+TX, formetanate hydrochloride (405)+TX, formothion (1192)+TX, formparanate (1193)+TX, fosmethilan (1194)+TX, fospirate (1195)+TX, fosthiazate (408)+TX, fosthietan (1196)+TX, furathiocarb (412)+TX, furethrin (1200)+TX, gamma-cyhalothrin (197)+TX, gamma-HCH (430)+TX, guazatine (422)+TX, guazatine acetates (422)+TX, GY-81 (development code) (423)+TX, halfenprox (424)+TX, halofenozide (425)+TX, HCH (430)+TX, HEOD (1070)+TX, heptachlor (1211)+TX, heptenophos (432)+TX, heterophos [CCN]+TX, hexaflumuron (439)+TX, HHDN (864)+TX, hydramethylnon (443)+TX, hydrogen cyanide (444)+TX, hyprene (445)+TX, hyquincarb (1223)+TX, imidacloprid (458)+TX, imiprothrin (460)+TX, indoxacarb (465)+TX, iodomethane (IUPAC name) (542)+TX, IPSP (1229)+TX, isazofos (1231)+TX, isobenzan (1232)+TX, isocarbophos (473)+TX, isodrin (1235)+TX, isofenphos (1236)+TX, isolane (1237)+TX, isoprocarb (472)+TX, isopropyl O-(methoxyaminothiophosphoryl)salicylate (IUPAC name) (473)+TX, isoprothiolane (474)+TX, isothioate (1244)+TX, isoxathion (480)+TX, ivermectin [CCN]+TX, jasmolin I (696)+TX, jasmolin II (696)+TX, jodfenphos (1248)+TX, juvenile hormone I [CCN]+TX, juvenile hormone II [CCN]+TX, juvenile hormone III [CCN]+TX, kelevan (1249)+TX, kinoprene (484)+TX, lambda-cyhalothrin (198)+TX, lead arsenate [CCN]+TX, lepimectin (CCN)+TX, leptophos (1250)+TX, lindane (430)+TX, lirimfos (1251)+TX, lufenuron (490)+TX, lythidathion (1253)+TX, m-cumenyl methylcarbamate (IUPAC name) (1014)+TX, magnesium phosphide (IUPAC name) (640)+TX, malathion (492)+TX, malonoben (1254)+TX, mazidox (1255)+TX, mecarbam (502)+TX, mecarphon (1258)+TX, menazon (1260)+TX, mephosfolan (1261)+TX, mercurous chloride (513)+TX, mesulfenfos (1263)+TX, metaflumizone (CCN)+TX, metam (519)+TX, metam-potassium (519)+TX, metam-sodium (519)+TX, methacrifos (1266)+TX, methamidophos (527)+TX, methanesulfonyl fluoride (IUPAC/Chemical Abstracts name) (1268)+TX, methidathion (529)+TX, methiocarb (530)+TX, methocrotophos (1273)+TX, methomyl (531)+TX, methoprene (532)+TX, methoquin-butyl (1276)+TX, methothrin (533)+TX, methoxychlor (534)+TX, methoxyfenozide (535)+TX, methyl bromide (537)+TX, methyl isothiocyanate (543)+TX, methylchloroform [CCN]+TX, methylene chloride [CCN]+TX, metofluthrin [CCN]+TX, metolcarb (550)+TX, metoxadiazone (1288)+TX, mevinphos (556)+TX, mexacarbate (1290)+TX, milbemectin (557)+TX, milbemycin oxime [CCN]+TX, mipafox (1293)+TX, mirex (1294)+TX, monocrotophos (561)+TX, morphothion (1300)+TX, moxidectin [CCN]+TX, naftalofos [CCN]+TX, naled (567)+TX, naphthalene (IUPAC/Chemical Abstracts name) (1303)+TX, NC-170 (development code) (1306)+TX, NC-184 (compound code)+TX, nicotine (578)+TX, nicotine sulfate (578)+TX, nifluridide (1309)+TX, nitenpyram (579)+TX, nithiazine (1311)+TX, nitrilacarb (1313)+TX, nitrilacarb 1:1 zinc chloride complex (1313)+TX, NNI-0101 (compound code)+TX, NNI-0250 (compound code)+TX, nornicotine (traditional name) (1319)+TX, novaluron (585)+TX, noviflumuron (586)+TX, O-5-dichloro-4-iodophenyl O-ethyl ethylphosphonothioate (IUPAC name) (1057)+TX, O,O-diethyl O-4-methyl-2-oxo-2H-chromen-7-yl phosphorothioate (IUPAC name) (1074)+TX, O,O-diethyl O-6-methyl-2-propylpyrimidin-4-yl phosphorothioate (IUPAC name) (1075)+TX, O,O,O',O'-tetrapropyl dithiopyrophosphate (IUPAC name) (1424)+TX, oleic acid (IUPAC name) (593)+TX, omethoate (594)+TX, oxamyl (602)+TX, oxydemeton-methyl (609)+TX, oxydeprofos (1324)+TX, oxydisulfoton (1325)+TX, pp'-DDT (219)+TX, para-dichlorobenzene [CCN]+TX, parathion (615)+TX, parathion-methyl (616)+TX, penfluron [CCN]+TX, pentachlorophenol (623)+TX, pentachlorophenyl laurate (IUPAC name) (623)+TX, permethrin (626)+TX, petroleum oils (628)+TX, PH 60-38 (development code) (1328)+TX, phenkapton (1330)+TX, phenothrin (630)+TX, phenthoate (631)+TX, phorate (636)+TX, phosalone (637)+TX, phosfolan (1338)+TX, phosmet (638)+TX, phosnichlor (1339)+TX, phosphamidon (639)+TX, phosphine (IUPAC name) (640)+TX, phoxim (642)+TX, phoxim-methyl (1340)+TX, pirimetaphos (1344)+TX, pirimicarb (651)+TX, pirimiphos-ethyl (1345)+TX, pirimiphos-methyl (652)+TX, polychlorodicyclopentadiene isomers (IUPAC name) (1346)+TX, polychloroterpenes (traditional name) (1347)+TX, potassium arsenite [CCN]+TX, potassium thiocyanate [CCN]+TX, prallethrin (655)+TX, precocene I [CCN]+TX, precocene II [CCN]+TX, precocene III [CCN]+TX, primidophos (1349)+TX, profenofos (662)+TX, profluthrin [CCN]+TX, promacyl (1354)+TX, promecarb (1355)+TX, propaphos (1356)+TX, propetamphos (673)+TX, propoxur (678)+TX, prothidathion (1360)+TX, prothiofos (686)+TX, prothoate (1362)+TX, protrifenbute [CCN]+TX, pymetrozine (688)+TX, pyraclofos (689)+TX, pyrazophos (693)+TX, pyresmethrin (1367)+TX, pyrethrin I (696)+TX, pyrethrin II (696)+TX, pyrethrins (696)+TX, pyridaben (699)+TX, pyridalyl (700)+TX, pyridaphenthion (701)+TX, pyrimidifen (706)+TX, pyrimitate (1370)+TX, pyriproxyfen (708)+TX, quassia [CCN]+TX, quinalphos (711)+TX, quinalphos-methyl (1376)+TX, quinothion (1380)+TX, quintiofos (1381)+TX, R-1492 (development code) (1382)+TX, rafoxanide [CCN]+TX, resmethrin (719)+TX, rotenone (722)+TX, RU 15525 (development code) (723)+TX, RU 25475 (development code) (1386)+TX, ryania (1387)+TX, ryanodine (traditional name) (1387)+TX, sabadilla (725)+TX, schradan (1389)+TX, sebufos+TX, selamectin [CCN]+TX, SI-0009 (compound code)+TX, SI-0205 (compound code)+TX, SI-0404 (compound code)+TX, SI-0405 (compound code)+TX, silafluofen (728)+TX, SN 72129 (development code) (1397)+TX, sodium arsenite [CCN]+TX, sodium cyanide (444)+TX, sodium fluoride (IUPAC/Chemical Abstracts name) (1399)+TX, sodium hexafluorosilicate (1400)+TX, sodium pentachlorophenoxide (623)+TX, sodium selenate (IUPAC name) (1401)+TX, sodium thiocyanate [CCN]+TX, sophamide (1402)+TX, spinosad (737)+TX, spiromesifen (739)+TX, spirotetrmat (CCN)+TX, sulcofuron (746)+TX, sulcofuron-sodium (746)+TX, sulfluramid (750)+TX, sulfotep (753)+TX, sulfuryl fluoride (756)+TX, sulprofos (1408)+TX, tar oils (758)+TX, tau-fluvalinate (398)+TX, tazimcarb (1412)+TX, TDE (1414)+TX, tebufenozide (762)+TX, tebufenpyrad (763)+TX, tebupirimfos (764)+TX, teflubenzuron (768)+TX, tefluthrin (769)+TX, temephos (770)+TX, TEPP (1417)+TX, terallethrin (1418)+TX, terbam+TX, terbufos (773)+TX, tetrachloroethane [CCN]+TX, tetrachlorvinphos (777)+TX, tetramethrin (787)+TX, theta-cypermethrin (204)+TX, thiacloprid (791)+TX, thiafenox+TX, thiamethoxam (792)+TX, thicrofos (1428)+TX, thiocarboxime (1431)+TX, thiocyclam (798)+TX, thiocyclam hydrogen oxalate (798)+TX, thiodicarb (799)+TX, thiofanox (800)+TX, thiometon (801)+TX, thionazin (1434)+TX, thiosultap (803)+TX, thiosultap-sodium (803)+TX, thuringiensin [CCN]+TX, tolfenpyrad (809)+TX, tralomethrin (812)+TX, transfluthrin (813)+TX, transpermethrin (1440)+TX, triamiphos (1441)+TX, triazamate (818)+TX, triazophos (820)+TX, triazuron+TX, trichlorfon (824)+TX, trichlormetaphos-3 [CCN]+TX, trichloronat (1452)+TX, trifenofos (1455)+TX, triflumuron (835)+TX, trimethacarb (840)+TX, triprene (1459)+TX, vamidothion (847)+TX, vaniliprole [CCN]+TX, veratridine (725)+TX, veratrine (725)+TX, XMC (853)+TX, xylylcarb (854)+TX, YI-5302 (compound code)+TX, zeta-cypermethrin (205)+TX, zetamethrin+TX, zinc phosphide (640)+TX, zolaprofos (1469) and ZXI 8901 (development code) (858)+TX, cyantraniliprole [736994-63-19+TX, chlorantraniliprole [500008-45-7]+TX, cyenopyrafen [560121-52-0]+TX, cyflumetofen [400882-07-7]+TX, pyrifluquinazon [337458-27-2]+TX, spinetoram [187166-40-1+187166-15-0]+TX, spirotetramat [203313-25-1]+TX, sulfoxaflor [946578-00-3]+TX, flufiprole [704886-18-0]+TX, meperfluthrin [915288-13-0]+TX, tetramethylfluthrin [84937-88-2]+TX, triflumezopyrim (disclosed in WO 2012/092115)+TX, a molluscicide selected from the group of substances consisting of bis(tributyltin) oxide (IUPAC name) (913)+TX, bromoacetamide [CCN]+TX, calcium arsenate [CCN]+TX, cloethocarb (999)+TX, copper acetoarsenite [CCN]+TX, copper sulfate (172)+TX, fentin (347)+TX, ferric phosphate (IUPAC name) (352)+TX, metaldehyde (518)+TX, methiocarb (530)+TX, niclosamide (576)+TX, niclosamide-olamine (576)+TX, pentachlorophenol (623)+TX, sodium pentachlorophenoxide (623)+TX, tazimcarb (1412)+TX, thiodicarb (799)+TX, tributyltin oxide (913)+TX, trifenmorph (1454)+TX, trimethacarb (840)+TX, triphenyltin acetate (IUPAC name) (347) and triphenyltin hydroxide (IUPAC name) (347)+TX, pyriprole [394730-71-3]+TX, a nematicide selected from the group of substances consisting of AKD-3088 (compound code)+TX, 1,2-dibromo-3-chloropropane (IUPAC/Chemical Abstracts name) (1045)+TX, 1,2-dichloropropane (IUPAC/Chemical Abstracts name) (1062)+TX, 1,2-dichloropropane with 1,3-dichloropropene (IUPAC name) (1063)+TX, 1,3-dichloropropene (233)+TX, 3,4-dichlorotetrahydrothiophene 1,1-dioxide (IUPAC/Chemical Abstracts name) (1065)+TX, 3-(4-chlorophenyl)-5-methylrhodanine (IUPAC name) (980)+TX, 5-methyl-6-thioxo-1,3,5-thiadiazinan-3-ylacetic acid (IUPAC name) (1286)+TX, 6-isopentenylaminopurine (210)+TX, abamectin (1)+TX, acetoprole [CCN]+TX, alanycarb (15)+TX, aldicarb (16)+TX, aldoxycarb (863)+TX, AZ 60541 (compound code)+TX, benclothiaz [CCN]+TX, benomyl (62)+TX, butylpyridaben+TX, cadusafos (109)+TX, carbofuran (118)+TX, carbon disulfide (945)+TX, carbosulfan (119)+TX, chloropicrin (141)+TX, chlorpyrifos (145)+TX, cloethocarb (999)+TX, cytokinins (210)+TX, dazomet (216)+TX, DBCP (1045)+TX, DCIP (218)+TX, diamidafos (1044)+TX, dichlofenthion (1051)+TX, dicliphos+TX, dimethoate (262)+TX, doramectin [CCN]+TX, emamectin (291)+TX, emamectin benzoate (291)+TX, eprinomectin [CCN]+TX, ethoprophos (312)+TX, ethylene dibromide (316)+TX, fenamiphos (326)+TX, fenpyrad+TX, fensulfothion (1158)+TX, fosthiazate (408)+TX, fosthietan (1196)+TX, furfural [CCN]+TX, GY-81 (development code) (423)+TX, heterophos [CCN]+TX, iodomethane (IUPAC name) (542)+TX, isamidofos (1230)+TX, isazofos (1231)+TX, ivermectin [CCN]+TX, kinetin (210)+TX, mecarphon (1258)+TX, metam (519)+TX, metam-potassium (519)+TX, metam-sodium (519)+TX, methyl bromide (537)+TX, methyl isothiocyanate (543)+TX, milbemycin oxime [CCN]+TX, moxidectin [CCN]+TX, *Myrothecium verrucaria* composition (565)+TX, NC-184 (compound code)+TX, oxamyl (602)+TX, phorate (636)+TX, phosphamidon (639)+TX, phosphocarb [CCN]+TX, sebufos+TX, selamectin [CCN]+TX, spinosad (737)+TX, terbam+TX, terbufos (773)+TX, tetrachlorothiophene (IUPAC/Chemical Abstracts name) (1422)+TX, thiafenox+TX, thionazin (1434)+TX, triazophos (820)+TX, triazuron+TX, xylenols [CCN]+TX, YI-5302 (compound code) and zeatin (210)+TX, fluensulfone [318290-98-1]+TX, a nitrification inhibitor selected from the group of substances consisting of potassium ethylxanthate [CCN] and nitrapyrin (580)+TX, a plant activator selected from the group of substances consisting of acibenzolar (6)+TX, acibenzolar-S-methyl (6)+TX, probenazole (658) and *Reynoutria sachalinensis* extract (720)+TX, a rodenticide selected from the group of substances consisting of 2-isovalerylindan-1,3-dione (IUPAC name) (1246)+TX, 4-(quinoxalin-2-ylamino)benzenesulfonamide (IUPAC name) (748)+TX, alpha-chlorohydrin [CCN]+TX, aluminium phosphide (640)+TX, antu (880)+TX, arsenous oxide (882)+TX, barium carbonate (891)+TX, bisthiosemi (912)+TX, brodifacoum (89)+TX, bromadiolone (91)+TX, bromethalin (92)+TX, calcium cyanide (444)+TX, chloralose (127)+TX, chlorophacinone (140)+TX, cholecalciferol (850)+TX, coumachlor (1004)+TX, coumafuryl (1005)+TX, coumatetralyl (175)+TX, crimidine (1009)+TX, difenacoum (246)+TX, difethialone (249)+TX, diphacinone (273)+TX, ergocalciferol (301)+TX, flocoumafen (357)+TX, fluoroacetamide (379)+TX, flupropadine (1183)+TX, flupropadine hydrochloride (1183)+TX, gamma-HCH (430)+TX, HCH (430)+TX, hydrogen cyanide (444)+TX, iodomethane (IUPAC name) (542)+TX, lindane (430)+TX, magnesium phosphide (IUPAC name) (640)+TX, methyl bromide (537)+TX, norbormide (1318)+TX, phosacetim (1336)+TX, phosphine (IUPAC name) (640)+TX, phosphorus [CCN]+TX, pindone (1341)+TX, potassium arsenite [CCN]+TX, pyrinuron (1371)+TX, scilliroside (1390)+TX, sodium arsenite [CCN]+TX, sodium cyanide (444)+TX, sodium fluoroacetate (735)+TX, strychnine (745)+TX, thallium sulfate [CCN]+TX, warfarin (851) and zinc phosphide (640)+TX, a synergist selected from the group of substances consisting of 2-(2-butoxyethoxy)ethyl piperonylate (IUPAC name) (934)+TX, 5-(1,3-benzodioxol-5-yl)-3-hexylcyclohex-2-enone (IUPAC name) (903)+TX, farnesol with nerolidol (324)+TX, MB-599 (development code) (498)+TX, MGK 264 (development code) (296)+TX, piperonyl butoxide (649)+TX, piprotal (1343)+TX, propyl isomer (1358)+TX, S421 (development code) (724)+TX, sesamex (1393)+TX, sesasmolin (1394) and sulfoxide (1406)+TX, an animal repellent selected from the group of substances consisting of anthraquinone (32)+TX, chloralose (127)+TX, copper naphthenate [CCN]+TX, copper oxychloride (171)+TX, diazinon (227)+TX, dicyclopentadiene (chemical name) (1069)+TX, guazatine (422)+TX, guazatine acetates (422)+TX, methiocarb (530)+TX, pyridin-4-amine (IUPAC name) (23)+TX, thiram (804)+TX, trimethacarb (840)+TX, zinc naphthenate [CCN] and ziram (856)+TX, a virucide selected from the group of substances consisting of imanin [CCN] and ribavirin [CCN]+TX, a wound protectant selected from the group of substances consisting of mercuric oxide (512)+TX, octhilinone (590) and thiophanate-methyl (802)+TX, and biologically active compounds selected from the group consisting of azaconazole (60207-31-0]+TX, bitertanol [70585-36-3]+TX, bromuconazole [116255-48-2]+TX, cyproconazole [94361-06-5]+TX, difenoconazole [119446-68-3]+TX, diniconazole [83657-24-3]+TX, epoxiconazole [106325-08-0]+TX, fenbuconazole [114369-43-6]+TX, fluquinconazole [136426-54-5]+TX, flusilazole [85509-19-9]+TX, flutriafol [76674-21-0]+TX, hexaconazole [79983-

71-4]+TX, imazalil [35554-44-0]+TX, imibenconazole [86598-92-7]+TX, ipconazole [125225-28-7]+TX, metconazole [125116-23-6]+TX, myclobutanil [88671-89-0]+TX, pefurazoate [101903-30-4]+TX, penconazole [66246-88-6]+TX, prothioconazole [178928-70-6]+TX, pyrifenox [88283-41-4]+TX, prochloraz [67747-09-5]+TX, propiconazole [60207-90-1]+TX, simeconazole [149508-90-7]+TX, tebuconazole [107534-96-3]+TX, tetraconazole [112281-77-3]+TX, triadimefon [43121-43-3]+TX, triadimenol [55219-65-3]+TX, triflumizole [99387-89-0]+TX, triticonazole [131983-72-7]+TX, ancymidol [12771-68-5]+TX, fenarimol [60168-88-9]+TX, nuarimol [63284-71-9]+TX, bupirimate [41483-43-6]+TX, dimethirimol [5221-53-4]+TX, ethirimol [23947-60-6]+TX, dodemorph [1593-77-7]+TX, fenpropidine [67306-00-7]+TX, fenpropimorph [67564-91-4]+TX, spiroxamine [118134-30-8]+TX, tridemorph [81412-43-3]+TX, cyprodinil [121552-61-2]+TX, mepanipyrim [110235-47-7]+TX, pyrimethanil [53112-28-0]+TX, fenpiclonil [74738-17-3]+TX, fludioxonil [131341-86-1]+TX, benalaxyl [71626-11-4]+TX, furalaxyl [57646-30-7]+TX, meta-laxyl [57837-19-1]+TX, R-metalaxyl [70630-17-0]+TX, ofurace [58810-48-3]+TX, oxadixyl [77732-09-3]+TX, benomyl [17804-35-2]+TX, carbendazim [10605-21-7]+TX, debacarb [62732-91-6]+TX, fuberidazole [3878-19-1]+TX, thiabendazole [148-79-8]+TX, chlozolinate [84332-86-5]+TX, dichlozoline [24201-58-9]+TX, iprodione [36734-19-7]+TX, myclozoline [54864-61-8]+TX, procymidone [32809-16-8]+TX, vinclozoline [50471-44-8]+TX, boscalid [188425-85-6]+TX, carboxin [5234-68-4]+TX, fenfuram [24691-80-3]+TX, flutolanil [66332-96-5]+TX, mepronil [55814-41-0]+TX, oxycarboxin [5259-88-1]+TX, penthiopyrad [183675-82-3]+TX, thifluzamide [130000-40-7]+TX, guazatine [108173-90-6]+TX, dodine [2439-10-3] [112-65-2] (free base)+TX, iminoctadine [13516-27-3]+TX, azoxystrobin [131860-33-8]+TX, dimoxystrobin [149961-52-4]+TX, enestroburin {Proc. BCPC, Int. Congr., Glasgow, 2003, 1, 93}+TX, fluoxastrobin [361377-29-9]+TX, kresoxim-methyl [143390-89-0]+TX, metominostrobin [133408-50-1]+TX, trifloxystrobin [141517-21-7]+TX, orysastrobin [248593-16-0]+TX, picoxystrobin [117428-22-5]+TX, pyraclostrobin [175013-18-0]+TX, ferbam [14484-64-1]+TX, mancozeb [8018-01-7]+TX, maneb [12427-38-2]+TX, metiram [9006-42-2]+TX, propineb [12071-83-9]+TX, thiram [137-26-8]+TX, zineb [12122-67-7]+TX, ziram [137-30-4]+TX, captafol [2425-06-1]+TX, captan [133-06-2]+TX, dichlofluanid [1085-98-9]+TX, fluoroimide [41205-21-4]+TX, folpet [133-07-3]+TX, tolylfluanid [731-27-1]+TX, bordeaux mixture [8011-63-0]+TX, copperhydroxid [20427-59-2]+TX, copperoxychlorid [1332-40-7]+TX, coppersulfat [7758-98-7]+TX, copperoxid [1317-39-1]+TX, mancopper [53988-93-5]+TX, oxine-copper [10380-28-6]+TX, dinocap [131-72-6]+TX, nitrothal-isopropyl [10552-74-6]+TX, edifenphos [17109-49-8]+TX, iprobenphos [26087-47-8]+TX, isoprothiolane [50512-35-1]+TX, phosdiphen [36519-00-3]+TX, pyrazophos [13457-18-6]+TX, tolclofos-methyl [57018-04-9]+TX, acibenzo-lar-S-methyl [135158-54-2]+TX, anilazine [101-05-3]+TX, benthiavalicarb [413615-35-7]+TX, blasticidin-S [2079-00-7]+TX, chinomethionat [2439-01-2]+TX, chloroneb [2675-77-6]+TX, chlorothalonil [1897-45-6]+TX, cyflufenamid [180409-60-3]+TX, cymoxanil [57966-95-7]+TX, dichlone [117-80-6]+TX, diclocymet [139920-32-4]+TX, diclomezine [62865-36-5]+TX, dicloran [99-30-9]+TX, diethofencarb [87130-20-9]+TX, dimethomorph [110488-70-5]+TX, SYP-L190 (Flumorph) [211867-47-9]+TX, dithianon [3347-22-6]+TX, ethaboxam [162650-77-3]+TX, etridiazole [2593-15-9]+TX, famoxadone [131807-57-3]+TX, fenamidone [161326-34-7]+TX, fenoxanil [115852-48-7]+TX, fentin [668-34-8]+TX, ferimzone [89269-64-7]+TX, fluazinam [79622-59-6]+TX, fluopicolide [239110-15-7]+TX, flusulfamide [106917-52-6]+TX, fenhexamid [126833-17-8]+TX, fosetyl-aluminium [39148-24-8]+TX, hymexazol [10004-44-1]+TX, iprovalicarb [140923-17-7]+TX, IKF-916 (Cyazofamid) [120116-88-3]+TX, kasugamycin [6980-18-3]+TX, methasulfocarb [66952-49-6]+TX, metrafenone [220899-03-6]+TX, pencycuron [66063-05-6]+TX, phthalide [27355-22-2]+TX, polyoxins [11113-80-7]+TX, probenazole [27605-76-1]+TX, propamocarb [25606-41-1]+TX, proquinazid [189278-12-4]+TX, pyroquilon [57369-32-1]+TX, quinoxyfen [124495-18-7]+TX, quintozene [82-68-8]+TX, sulfur [7704-34-9]+TX, tiadinil [223580-51-6]+TX, triazoxide [72459-58-6]+TX, tricyclazole [41814-78-2]+TX, triforine [26644-46-2]+TX, validamycin [37248-47-8]+TX, zoxamide (RH7281) [156052-68-5]+TX, mandipropamid [374726-62-2]+TX, isopyrazam [881685-58-1]+TX, sedaxane [874967-67-6]+TX, 3-difluoromethyl-1-methyl-1H-pyrazole-4-carboxylic acid (9-dichloromethylene-1,2,3,4-tetrahydro-1,4-methano-naphthalen-5-yl)-amide (dislosed in WO 2007/048556)+TX, 3-difluoromethyl-1-methyl-1H-pyrazole-4-carboxylic acid (3',4',5'-trifluoro-biphenyl-2-yl)-amide (disclosed in WO 2006/087343)+TX, [(3S,4R,4aR,6S,6aS,12R,12aS,12bS)-3-[(cyclopropylcarbonyl)oxy]-1,3,4,4a,5,6,6a,12,12a,12b-decahydro-6,12-dihydroxy-4,6a,12b-trimethyl-11-oxo-9-(3-pyridinyl)-2H,11Hnaphtho[2,1-b]pyrano[3,4-e]pyran-4-yl] methyl-cyclopropanecarboxylate [915972-17-7]+TX and 1,3,5-trimethyl-N-(2-methyl-1-oxopropyl)-N-[3-(2-methylpropyl)-4-[2,2,2-trifluoro-1-methoxy-1-(trifluoromethyl) ethyl]phenyl]-1H-pyrazole-4-carboxamide [926914-55-8]+TX, lancotrione [1486617-21-3]+TX, florpyrauxifen [943832-81-3]]+TX, ipfentrifluconazole[1417782-08-1]+TX, mefentrifluconazole [1417782-03-6]+TX, quinofumelin [861647-84-9]+TX, chloroprallethrin [399572-87-3]+TX, cyhalodiamide [1262605-53-7]]+TX, fluazaindolizine [1254304-22-7]+TX, fluxametamide [928783-29-3]+TX, epsilon-metofluthrin [240494-71-7]+TX, epsilon-momfluorothrin [1065124-65-3]+TX, pydiflumetofen [1228284-64-7]+TX, kappa-bifenthrin [439680-76-9]+TX, broflanilide [1207727-04-5]+TX, dicloromezotiaz [1263629-39-5]+TX, dipymetitrone [16114-35-5]+TX, pyraziflumid [942515-63-1]+TX and kappa-tefluthrin [391634-71-2]+TX; and microbials including: *Acinetobacter lwoffii*+TX, *Acremonium alternatum*+TX+TX, *Acremonium cephalosporium*+TX+TX, *Acremonium diospyri*+TX, *Acremonium obclavatum*+TX, *Adoxophyes orana granulovirus* (AdoxGV) (Capex®)+TX, *Agrobacterium radiobacter* strain K84 (Galltrol-A®)+TX, *Alternaria alternate*+TX, *Alternaria cassia*+TX, *Alternaria destruens* (Smolder®)+TX, *Ampelomyces quisqualis* (AQ10®)+TX, *Aspergillus flavus* AF36 (AF36®)+TX, *Aspergillus flavus* NRRL 21882 (Aflaguard®)+TX, *Aspergillus* spp.+TX, *Aureobasidium pullulans*+TX, *Azospirillum*+TX, (MicroAZ®+TX, TAZO B®)+TX, *Azotobacter*+TX, *Azotobacter chroococcum* (Azotomeal®)+TX, *Azotobacter* cysts (Bionatural Blooming Blossoms®)+TX, *Bacillus amyloliquefaciens*+TX, *Bacillus cereus*+TX, *Bacillus chitinosporus* strain CM-1+TX, *Bacillus chitinosporus* strain AQ746+TX, *Bacillus licheniformis* strain HB-2 (Biostart™ Rhizoboost®)+TX, *Bacillus licheniformis* strain 3086 (EcoGuard®+TX, Green Releaf®)+TX, *Bacillus circulans*+TX, *Bacillus firmus* (BioSafe®, BioNem-WP®, VOTiVO®)+TX, *Bacillus firmus* strain 1-1582+TX, *Bacillus macerans*+TX, *Bacillus marismortui*+TX, *Bacillus megaterium*+TX, *Bacillus mycoides* strain AQ726+TX, *Bacillus papillae* (Milky Spore Powder®)+TX, *Bacillus pumilus* spp.+TX, *Bacillus pumilus* strain GB34 (Yield Shield®)+TX, *Bacillus pumilus* strain AQ717+TX, *Bacillus pumilus* strain QST 2808 (Sonata®+TX, Ballad Plus®)+TX, *Bacillus spahericus* (VectoLex®)+TX, *Bacillus* spp.+TX, *Bacillus* spp. strain AQ175+TX, *Bacillus* spp. strain AQ177+TX, *Bacillus* spp. strain AQ178+TX, *Bacillus subtilis* strain QST 713 (CEASE®+TX, Serenade®+TX, Rhapsody®)+TX, *Bacillus subtilis* strain QST 714 (JAZZ®)+TX, *Bacillus subtilis* strain AQ153+TX, *Bacillus subtilis* strain AQ743+TX, *Bacillus subtilis* strain QST3002+TX, *Bacillus subtilis* strain QST3004+TX, *Bacillus subtilis* var. *amyloliquefaciens* strain FZB24 (Taegro®+TX, Rhizopro®)+TX, *Bacillus thuringiensis* Cry 2Ae+TX, *Bacillus thuringiensis* Cry1Ab+TX, *Bacillus thuringiensis aizawai* GC 91 (Agree®)+TX, *Bacillus thuringiensis israelensis* (BMP123®+TX, Aquabac®+TX, VectoBac®)+TX, *Bacillus thuringiensis kurstaki* (Javelin®+TX, Deliver®+TX, CryMax®+TX, Bonide®+TX, Scutella WP®+TX, Turilav WP®+TX, Astuto®+TX, Dipel WP®+TX, Biobit®+TX, Foray®)+TX, *Bacillus thuringiensis kurstaki* BMP 123 (Baritone®)+TX, *Bacillus thuringiensis kurstaki* HD-1 (Bioprotec-CAF/3P®)+TX, *Bacillus thuringiensis* strain BD #32+TX, *Bacillus thuringiensis* strain AQ52+TX, *Bacillus thuringiensis* var. *aizawai* (XenTari®+TX, DiPel®)+TX, bacteria spp. (GROWMEND®+TX, GROWSWEET®+TX, Shootup®)+TX, bacteriophage of *Clavipacter michiganensis* (AgriPhage®)+TX, Bakflor®+TX, *Beauveria bassiana* (Beaugenic®+TX, Brocaril WP®)+TX, *Beauveria bassiana* GHA (Mycotrol ES®+TX, Mycotrol O®+TX, BotaniGuard®)+TX, *Beauveria brongniartii* (Engerlingspilz®+TX, Schweizer Beauveria®+TX, Melocont®)+TX, *Beauveria* spp.+TX, *Botrytis cineria*+TX, *Bradyrhizobium japonicum* (TerraMax®)+TX, *Brevibacillus brevis*+TX, *Bacillus thuringiensis tenebrionis* (Novodor®)+TX, BtBooster+TX, *Burkholderia cepacia* (Deny®+TX, Intercept®+TX, Blue Circle®)+TX, *Burkholderia gladii*+TX, *Burkholderia gladioli*+TX, *Burkholderia* spp.+TX, Canadian thistle fungus (CBH Canadian Bioherbicide®)+TX, *Candida butyri*+TX, *Candida famata*+TX, *Candida fructus*+TX, *Candida glabrata*+TX, *Candida guilliermondii*+TX, *Candida melibiosica*+TX, *Candida oleophila* strain O+TX, *Candida parapsilosis*+TX, *Candida pelliculosa*+TX, *Candida pulcherrima*+TX, *Candida reukaufii*+TX, *Candida saitoana* (Bio-Coat®+TX, Biocure®)+TX, *Candida sake*+TX, *Candida* spp.+TX, *Candida tenius*+TX, *Cedecea dravisae*+TX, *Cellulomonas flavigena*+TX, *Chaetomium cochliodes* (Nova-Cide®)+TX, *Chaetomium globosum* (Nova-Cide®)+TX, *Chromobacterium subtsugae* strain PRAA4-1T (Grandevo®)+TX, *Cladosporium cladosporioides*+TX, *Cladosporium oxysporum*+TX, *Cladosporium chlorocephalum*+TX, *Cladosporium* spp.+TX, *Cladosporium tenuissimum*+TX, *Clonostachys rosea* (EndoFine®)+TX, *Colletotrichum acutatum*+TX, *Coniothyrium minitans* (Cotans WG®)+TX, *Coniothyrium* spp.+TX, *Cryptococcus albidus* (YIELDPLUS®)+TX, *Cryptococcus humicola*+TX, *Cryptococcus infirmo-miniatus*+TX, *Cryptococcus laurentii*+TX, *Cryptophlebia leucotreta* granulovirus (Cryptex®)+TX, *Cupriavidus campinensis*+TX, *Cydia pomonella* granulovirus (CYD-X®)+TX, *Cydia pomonella* granulovirus (Madex®+TX, Madex Plus®+TX, Madex Max/Carpovirusine®)+TX, *Cylindrobasidium laeve* (Stumpout®)+TX, *Cylindrocladium*+TX, *Debaryomyces hansenii*+TX, *Drechslera hawaiinensis*+TX, *Enterobacter cloacae*+TX, *Enterobacteriaceae*+TX, *Entomophtora virulenta* (Vektor®)+TX, *Epicoccum nigrum*+TX, *Epicoccum purpurascens*+TX, *Epicoccum* spp.+TX, *Filobasidium floriforme*+TX, *Fusarium acuminatum*+TX, *Fusarium chlamydosporum*+TX, *Fusarium oxysporum* (Fusaclean®/Biofox C®)+TX, *Fusarium proliferatum*+TX, *Fusarium* spp.+TX, *Galactomyces geotrichum*+TX, *Gliocladium catenulatum* (Primastop®+TX, Prestop®)+TX, *Gliocladium roseum*+TX, *Gliocladium* spp. (SoilGard®)+TX, *Gliocladium virens* (Soilgard®)+TX, *Granulovirus* (Granupom®)+TX, *Halobacillus halophilus*+TX, *Halobacillus litoralis*+TX, *Halobacillus trueperi*+TX, *Halomonas* spp.+TX, *Halomonas subglaciescola*+TX, *Halovibrio variabilis*+TX, *Hanseniaspora uvarum*+TX, *Helicoverpa armigera* nucleopolyhedrovirus (Helicovex®)+TX, *Helicoverpa zea* nuclear polyhedrosis virus (Gemstar®)+TX, Isoflavone—formononetin (Myconate®)+TX, *Kloeckera apiculata*+TX, *Kloeckera* spp.+TX, *Lagenidium giganteum* (Laginex®)+TX, *Lecanicillium longisporum* (Vertiblast®)+TX, *Lecanicillium muscarium* (Vertikil®)+TX, *Lymantria Dispar* nucleopolyhedrosis virus (Disparvirus®)+TX, *Marinococcus halophilus*+TX, *Meira geulakonigii*+TX, *Metarhizium anisopliae* (Met52®)+TX, *Metarhizium anisopliae* (Destruxin WP®)+TX, *Metschnikowia fruticola* (Shemer®)+TX, *Metschnikowia pulcherrima*+TX, *Microdochium dimerum* (Antibot®)+TX, *Micromonospora coerulea*+TX, *Microsphaeropsis ochracea*+TX, *Muscodor albus* 620 (Muscudor®)+TX, *Muscodor roseus* strain A3-5+TX, *Mycorrhizae* spp. (AMykor®+TX, Root Maximizer®)+TX, *Myrothecium verrucaria* strain AARC-0255 (DiTera®)+TX, BROS PLUS®+TX, *Ophiostoma piliferum* strain D97 (Sylvanex®)+TX, *Paecilomyces farinosus*+TX, *Paecilomyces fumosoroseus* (PFR-97®+TX, PreFeRal®)+TX, *Paecilomyces linacinus* (Biostat WP®)+TX, *Paecilomyces lilacinus* strain 251 (MeloCon WG®)+TX, *Paenibacillus polymyxa*+TX, *Pantoea agglomerans* (BlightBan C9-1®)+TX, *Pantoea* spp.+TX, *Pasteuria* spp. (Econem®)+TX, *Pasteuria nishizawae*+TX, *Penicillium aurantiogriseum*+TX, *Penicillium billai* (Jumpstart®+TX, TagTeam®)+TX, *Penicillium brevicompactum*+TX, *Penicillium frequentans*+TX, *Penicillium griseofulvum*+TX, *Penicillium purpurogenum*+TX, *Penicillium* spp.+TX, *Penicillium viridicatum*+TX, *Phlebiopsis gigantean* (Rotstop®)+TX, phosphate solubilizing bacteria (Phosphomeal®)+TX, *Phytophthora cryptogea*+TX, *Phytophthora palmivora* (Devine®)+TX, *Pichia anomala*+TX, *Pichia guilermondii*+TX, *Pichia membranaefaciens*+TX, *Pichia onychis*+TX, *Pichia stipites*+TX, *Pseudomonas aeruginosa*+TX, *Pseudomonas aureofasciens* (Spot-Less Biofungicide®)+TX, *Pseudomonas cepacia*+TX, *Pseudomonas chlororaphis* (AtEze®)+TX, *Pseudomonas corrugate*+TX, *Pseudomonas fluorescens* strain A506 (BlightBan A506®)+TX, *Pseudomonas putida*+TX, *Pseudomonas reactans*+TX, *Pseudomonas* spp.+TX, *Pseudomonas syringae* (Bio-Save®)+TX, *Pseudomonas viridiflava*+TX, *Pseudomons fluorescens* (Zequanox®)+TX, *Pseudozyma flocculosa* strain PF-A22 UL (Sporodex L®)+TX, *Puccinia canaliculata*+TX, *Puccinia thlaspeos* (Wood Warrior®)+TX, *Pythium paroecandrum*+TX, *Pythium oligandrum* (Polygandron®+TX, Polyversum®)+TX, *Pythium periplocum*+TX, *Rhanella aquatilis*+TX, *Rhanella* spp.+TX, *Rhizobia* (Dormal®+TX, Vault®)+TX, *Rhizoctonia*+TX, *Rhodococcus globerulus* strain AQ719+TX, *Rhodosporidium diobovatum*+TX, *Rhodosporidium toruloides*+TX, *Rhodotorula* spp.+TX, *Rhodotorula glutinis*+TX, *Rhodotorula graminis*+TX, *Rhodotorula mucilagnosa*+TX, *Rhodotorula rubra*+TX, *Saccharomyces cerevisiae*+TX, *Salinococcus roseus*+TX, *Sclerotinia minor*+TX, *Sclerotinia minor* (SARRITOR®)+TX, *Scytalidium* spp.+TX, *Scytalidium uredinicola*+TX, *Spodoptera exigua* nuclear polyhedrosis virus (Spod-X®+TX, Spexit®)+TX, *Serratia* marcescens+TX, *Serratia plymuthica*+TX, *Serratia* spp.+TX, *Sordaria fimicola*+TX, *Spodoptera littoralis* nucleopolyhedrovirus (Littovir®)+TX, *Sporobolomyces roseus*+TX, *Stenotrophomonas maltophilia*+TX, *Streptomyces ahygroscopicus*+TX, *Streptomyces albaduncus*+TX, *Streptomyces exfoliates*+TX, *Streptomyces galbus*+TX, *Streptomyces griseoplanus*+TX, *Streptomyces griseoviridis* (Mycostop®)+TX, *Streptomyces lydicus* (Actinovate®)+TX, *Streptomyces lydicus* WYEC-108 (ActinoGrow®)+TX, *Streptomyces violaceus*+TX, *Tilletiopsis minor*+TX, *Tilletiopsis* spp.+TX, *Trichoderma asperellum* (T34 Biocontrol®)+TX, *Trichoderma gamsii* (Tenet®)+TX, *Trichoderma atroviride* (Plantmate®)+TX, *Trichoderma hamatum* TH 382+TX, *Trichoderma harzianum rifai* (Mycostar®)+TX, *Trichoderma harzianum* T-22 (Trianum-P®+TX, PlantShield HC®+TX, RootShield®+TX, Trianum-G®)+TX, *Trichoderma harzianum* T-39 (Trichodex®)+TX, *Trichoderma inhamatum*+TX, *Trichoderma koningii*+TX, *Trichoderma* spp. LC 52 (Sentinel®)+TX, *Trichoderma lignorum*+TX, *Trichoderma longibrachiatum*+TX, *Trichoderma polysporum* (Binab T®)+TX, *Trichoderma taxi*+TX, *Trichoderma virens*+TX, *Trichoderma virens* (formerly *Gliocladium virens* GL-21) (SoilGuard®)+TX, *Trichoderma viride*+TX, *Trichoderma viride* strain ICC 080 (Remedier®)+TX, *Trichosporon pullulans*+TX, *Trichosporon* spp.+TX, *Trichothecium* spp.+TX, *Trichothecium roseum*+TX, *Typhula phacorrhiza* strain 94670+TX, *Typhula phacorrhiza* strain 94671+TX, *Ulocladium atrum*+TX, *Ulocladium oudemansii* (Botry-Zen®)+TX, *Ustilago maydis*+TX, various bacteria and supplementary micronutrients (Natural II®)+TX, various fungi (Millennium Microbes®)+TX, *Verticillium chlamydosporium*+TX, *Verticillium lecanii* (Mycotal®+TX, Vertalec®)+TX, Vip3Aa20 (VIPtera®)+TX, *Virgibacillus marismortui*+TX, *Xanthomonas campestris* pv. *Poae* (Camperico®)+TX, *Xenorhabdus bovienii*+TX, *Xenorhabdus nematophilus*; and Plant extracts including: pine oil (Retenol®)+TX, azadirachtin (Plasma Neem Oil®+TX, AzaGuard®+TX, MeemAzal®+TX, Molt-X®+TX, Botanical IGR (Neemazad®, Neemix®)+TX, canola oil (Lilly Miller Vegol®)+TX, *Chenopodium ambrosioides* near *ambrosioides* (Requiem®)+TX, *Chrysanthemum* extract (Crisant®)+TX, extract of neem oil (Trilogy®)+TX, essentials oils of *Labiatae* (Botanic®)+TX, extracts of clove rosemary peppermint and thyme oil (Garden insect Killer®)+TX, Glycinebetaine (Greenstim®)+TX, garlic+TX, lemongrass oil (GreenMatch®)+TX, neem oil+TX, *Nepeta cataria* (Catnip oil)+TX, *Nepeta catarina*+TX, nicotine+TX, oregano oil (MossBuster®)+TX, *Pedaliaceae* oil (Nematon®)+TX, pyrethrum+TX, *Quillaja saponaria* (NemaQ®)+TX, *Reynoutria sachalinensis* (Regalia®+TX, Sakalia®)+TX, rotenone (Eco Roten®)+TX, *Rutaceae* plant extract (Soleo®)+TX, soybean oil (Ortho Ecosense®)+TX, tea tree oil (Timorex Gold®)+TX, thymus oil+TX, AGNIQUE® MMF+TX, BugOil®+TX, mixture of rosemary sesame peppermint thyme and cinnamon extracts (EF 300®)+TX, mixture of clove rosemary and peppermint extract (EF 400®)+TX, mixture of clove pepermint garlic oil and mint (Soil Shot®)+TX, kaolin (Screen®)+TX, storage glucam of brown algae (Laminarin®)+TX; and pheromones including: blackheaded fireworm pheromone (3M Sprayable Blackheaded Fireworm Pheromone®)+TX, Codling Moth Pheromone (Paramount dispenser-(CM)/Isomate C-Plus®)+TX, Grape Berry Moth Pheromone (3M MEC-GBM Sprayable Pheromone®)+TX, Leafroller pheromone (3M MEC—LR Sprayable Pheromone®)+TX, Muscamone (Snip7 Fly Bait®+TX, Starbar Premium Fly Bait®)+TX, Oriental Fruit Moth Pheromone (3M oriental fruit moth sprayable Pheromone®)+TX, Peachtree Borer Pheromone (Isomate-P®)+TX, Tomato Pinworm Pheromone (3M Sprayable Pheromone®)+TX, Entostat powder (extract from palm tree) (Exosex CM®)+TX, Tetradecatrienyl acetate+TX, 13-Hexadecatrienal+TX, (E+TX, Z)-7+TX, 9-Dodecadien-1-yl acetate+TX, 2-Methyl-1-butanol+TX, Calcium acetate+TX, Scenturion®+TX, Biolure®+TX, Check-Mate®+TX, Lavandulyl senecioate; and Macrobials including: *Aphelinus abdominalis*+TX, *Aphidius ervi* (Aphelinus-System®)+TX, *Acerophagus papaya*+TX, *Adalia bipunctata* (Adalia-System®)+TX, *Adalia bipunctata* (Adaline®)+TX, *Adalia bipunctata* (Aphidalia®)+TX, *Ageniaspis citricola*+TX, *Ageniaspis fuscicollis*+TX, *Amblyseius andersoni* (Anderline®+TX, Andersoni-System®)+TX, *Amblyseius califomicus* (Amblyline®+TX, Spical®)+TX, *Amblyseius cucumeris* (Thripex®+TX, Bugline Cucumeris®)+TX, *Amblyseius fallacis* (Fallacis®)+TX, *Amblyseius swirskii* (Bugline Swirskii®+TX, Swirskii-Mite®)+TX, *Amblyseius womersleyi* (WomerMite®)+TX, *Amitus hesperidum*+TX, *Anagrus atomus*+TX, *Anagyrus fusciventris*+TX, *Anagyrus kamali*+TX, *Anagyrus loecki*+TX, *Anagyrus pseudococci* (Citripar®)+TX, *Anicetus benefices*+TX, *Anisopteromalus calandrae*+TX, *Anthocoris nemoralis* (Anthocoris-System®)+TX, *Aphelinus abdominalis* (Apheline®+TX, Aphiline®)+TX, *Aphelinus asychis*+TX, *Aphidius colemani* (Aphipar®)+TX, *Aphidius ervi* (Ervipar®)+TX, *Aphidius gifuensis*+TX, *Aphidius matricariae* (Aphipar-M®)+TX, *Aphidoletes aphidimyza* (Aphidend®)+TX, *Aphidoletes aphidimyza* (Aphidoline®)+TX, *Aphytis lingnanensis*+TX, *Aphytis melinus*+TX, *Aprostocetus hagenowii*+TX, *Atheta coriaria* (Staphyline®)+TX, *Bombus* spp.+TX, *Bombus terrestris* (Natupol Beehive®)+TX, *Bombus terrestris* (Beeline®+TX, Tripol®)+TX, *Cephalonomia stephanoderis*+TX, *Chilocorus nigritus*+TX, *Chrysoperla carnea* (Chrysoline®)+TX, *Chrysoperla carnea* (Chrysopa®)+TX, *Chrysoperla rufilabris*+TX, *Cirrospilus ingenuus*+TX, *Cirrospilus quadristriatus*+TX, *Citrostichus phyllocnistoides*+TX, *Closterocerus chamaeleon*+TX, *Closterocerus* spp.+TX, *Coccidoxenoides perminutus* (Planopar®)+TX, *Coccophagus cowperi*+TX, *Coccophagus lycimnia*+TX, *Cotesia flavipes*+TX, *Cotesia plutellae*+TX, *Cryptolaemus montrouzieri* (Cryptobug®+TX, Cryptoline®)+TX, *Cybocephalus nipponicus*+TX, *Dacnusa sibirica*+TX, *Dacnusa sibirica* (Minusa®)+TX, *Diglyphus isaea* (Diminex®)+TX, *Delphastus catalinae* (Delphastus®)+TX, *Delphastus pusillus*+TX, *Diachasmimorpha krausii*+TX, *Diachasmimorpha longicaudata*+TX, *Diaparsis jucunda*+TX, *Diaphorencyrtus aligarhensis*+TX, *Diglyphus isaea*+TX, *Diglyphus isaea* (Miglyphus®+TX, Digline®)+TX, *Dacnusa sibirica* (Dac-Digline®+TX, Minex®)+TX, *Diversinervus* spp.+TX, *Encarsia citrina*+TX, *Encarsia formosa* (Encarsia Max®+TX, Encarline®+TX, En-Strip®)+TX, *Eretmocerus eremicus* (Enermix®)+TX, *Encarsia guadeloupae*+TX, *Encarsia haitiensis*+TX, *Episyrphus balteatus* (Syrphidend®)+TX, *Eretmoceris siphonini*+TX, *Eretmocerus californicus*+TX, *Eretmocerus eremicus* (Ercal®+TX, Eretline e®)+TX, *Eretmocerus eremicus* (Bemimix®)+TX, *Eretmocerus hayati*+TX, *Eretmocerus mundus* (Bemipar®+TX, Eretline m®)+TX, *Eretmocerus siphonini*+TX, *Exochomus quadripustulatus*+TX, *Feltiella acarisuga* (Spidend®)+TX, *Feltiella acarisuga* (Feltiline®)+TX, *Fopius arisanus*+TX, *Fopius ceratitivorus*+TX, Formononetin (Wirless Beehome®)+TX, *Franklinothrips vespiformis* (Vespop®)+TX, *Galendromus occidentalis*+TX, *Goniozus legneri*+TX, *Habrobracon hebetor*+TX, *Harmonia axyridis* (Harmo- Beetle®)+TX, *Heterorhabditis* spp. (Lawn Patrol®)+TX, *Heterorhabditis bacteriophora* (NemaShield HB®+TX, Nemaseek®+TX, Terranem-Nam®+TX, Terranem®+TX, Larvanem®+TX, B-Green®+TX, NemAttack®+TX, Nematop®)+TX, *Heterorhabditis megidis* (Nemasys H®+TX, BioNem H®+TX, Exhibitline hm®+TX, Larvanem-M®)+TX, *Hippodamia convergens*+TX, *Hypoaspis aculeifer* (Aculeifer-System®+TX, Entomite-A®)+TX, *Hypoaspis miles* (Hypoline m®+TX, Entomite-M®)+TX, *Lbalia leucospoides*+TX, *Lecanoideus floccissimus*+TX, *Lemophagus errabundus*+TX, *Leptomastidea abnormis*+TX, *Leptomastix dactylopii* (Leptopar®)+TX, *Leptomastix epona*+TX, *Lindorus lophanthae*+TX, *Lipolexis oregmae*+TX, *Lucilia caesar* (Natufly®)+TX, *Lysiphlebus testaceipes*+TX, *Macrolophus caliginosus* (Mirical-N®+TX, Macroline c®+TX, Mirical®)+TX, *Mesoseiulus longipes*+TX, *Metaphycus flavus*+TX, *Metaphycus lounsburyi*+TX, *Micromus angulatus* (Milacewing®)+TX, *Microterys flavus*+TX, *Muscidifurax raptorellus* and *Spalangia cameroni* (Biopar®)+TX, *Neodryinus typhlocybae*+TX, *Neoseiulus califomicus*+TX, *Neoseiulus cucumeris* (THRYPEX®)+TX, *Neoseiulus fallacis*+TX, *Nesideocoris tenuis* (NesidioBug®+TX, Nesibug®)+TX, *Ophyra aenescens* (Biofly®)+TX, *Orius insidiosus* (Thripor-I®+TX, Oriline i®)+TX, *Orius laevigatus* (Thripor-L®+TX, Oriline I®)+TX, *Orius majusculus* (Oriline m®)+TX, *Orius strigicollis* (Thripor-S®)+TX, *Pauesia juniperorum*+TX, *Pediobius foveolatus*+TX, *Phasmarhabditis hermaphrodita* (Nemaslug®)+TX, *Phymastichus coffee*+TX, *Phytoseiulus macropilus*+TX, *Phytoseiulus persimilis* (Spidex®+TX, Phytoline p®)+TX, *Podisus maculiventris* (Podisus®)+TX, *Pseudacteon curvatus*+TX, *Pseudacteon obtusus*+TX, *Pseudacteon tricuspis*+TX, *Pseudaphycus maculipennis*+TX, *Pseudleptomastix mexicana*+TX, *Psyllaephagus pilosus*+TX, *Psyttalia concolor* (complex)+TX, *Quadrastichus* spp.+TX, *Rhyzobius lophanthae*+TX, *Rodolia cardinalis*+TX, *Rumina decollate*+TX, *Semielacher petiolatus*+TX, *Sitobion avenae* (Ervibank®)+TX, *Steinernema carpocapsae* (Nematac C®+TX, Millenium®+TX, BioNem C®+TX, NemAttack®+TX, Nemastar®+TX, Capsanem®)+TX, *Steinernema feltiae* (NemaShield®+TX, Nemasys F®+TX, BioNem F®+TX, Steinernema-System®+TX, NemAttack®+TX, Nemaplus®+TX, Exhibitline sf®+TX, Sciarid®+TX, Entonem®)+TX, *Steinernema kraussei* (Nemasys L®+TX, BioNem L®+TX, Exhibitline srb®)+TX, *Steinernema riobrave* (BioVector®+TX, BioVektor®)+TX, *Steinernema scapterisci* (Nematac S®)+TX, *Steinernema* spp.+TX, *Steinernematid* spp. (Guardian Nematodes®)+TX, *Stethorus punctillum* (Stethorus®)+TX, *Tamarixia radiate*+TX, *Tetrastichus setifer*+TX, *Thripobius semiluteus*+TX, *Torymus sinensis*+TX, *Trichogramma brassicae* (Tricholine b®)+TX, *Trichogramma brassicae* (TrichoStrip®)+TX, *Trichogramma evanescens*+TX, *Trichogramma minutum*+TX, *Trichogramma ostriniae*+TX, *Trichogramma platneri*+TX, *Trichogramma pretiosum*+TX, *Xanthopimpla stemmator*; and other biologicals including: abscisic acid+TX, bioSea®+TX, *Chondrostereum purpureum* (Chontrol Paste®)+TX, *Colletotrichum gloeosporioides* (Collego®)+TX, Copper Octanoate (Cueva®)+TX, Delta traps (Trapline d®)+TX, *Erwinia amylovora* (Harpin) (ProAct®+TX, Ni-HIBIT Gold CST®)+TX, Ferri-phosphate (Ferramol®)+TX, Funnel traps (Trapline y®)+TX, Gallex®+TX, Grower's Secret®+TX, Homo-brassonolide+TX, Iron Phosphate (Lilly Miller Worry Free Ferramol Slug & Snail Bait®)+TX, MCP hail trap (Trapline f®)+TX, *Microctonus hyperodae*+TX, *Mycoleptodiscus terrestris* (Des-X®)+TX, BioGain®+TX, Aminomite®+TX, Zenox®+TX, Pheromone trap (Thripline ams®)+TX, potassium bicarbonate (MilStop®)+TX, potassium salts of fatty acids (Sanova®)+TX, potassium silicate solution (Sil-Matrix®)+TX, potassium iodide+potassiumthiocyanate (Enzicur®)+TX, SuffOil-X®+TX, Spider venom+TX, *Nosema locustae* (Semaspore Organic Grasshopper Control®)+TX, Sticky traps (Trapline YF®+TX, Rebell Amarillo®)+TX and Traps (Takitrapline y+b®)+TX.

The references in brackets behind the active ingredients, e.g. [3878-19-1] refer to the Chemical Abstracts Registry number. The above described mixing partners are known. Where the active ingredients are included in "The Pesticide Manual" [The Pesticide Manual—A World Compendium; Thirteenth Edition; Editor: C. D. S. TomLin; The British Crop Protection Council], they are described therein under the entry number given in round brackets hereinabove for the particular compound; for example, the compound "abamectin" is described under entry number (1). Where "[CCN]" is added hereinabove to the particular compound, the compound in question is included in the "Compendium of Pesticide Common Names", which is accessible on the internet [A. Wood; *Compendium of Pesticide Common Names*, Copyright© 1995-2004]; for example, the compound "acetoprole" is described under the internet address http://www.alanwood.net/pesticides/acetoprole.html.

Most of the active ingredients described above are referred to hereinabove by a so-called "common name", the relevant "ISO common name" or another "common name" being used in individual cases. If the designation is not a "common name", the nature of the designation used instead is given in round brackets for the particular compound; in that case, the IUPAC name, the IUPAC/Chemical Abstracts name, a "chemical name", a "traditional name", a "compound name" or a "development code" is used. "CAS Reg. No" means the Chemical Abstracts Registry Number.

The active ingredient mixture of the compounds of formula I selected from Table 1 and A with active ingredients described above comprises a compound selected from Table 1 and A and an active ingredient as described above preferably in a mixing ratio of from 100:1 to 1:6000, especially from 50:1 to 1:50, more especially in a ratio of from 20:1 to 1:20, even more especially from 10:1 to 1:10, very especially from 5:1 and 1:5, special preference being given to a ratio of from 2:1 to 1:2, and a ratio of from 4:1 to 2:1 being likewise preferred, above all in a ratio of 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are by weight.

The mixtures as described above can be used in a method for controlling pests, which comprises applying a composition comprising a mixture as described above to the pests or their environment, with the exception of a method for treatment of the human or animal body by surgery or therapy and diagnostic methods practised on the human or animal body.

The mixtures comprising a compound of formula I selected from Table 1 and A and one or more active ingredients as described above can be applied, for example, in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the compounds of formula I selected from Table 1 and A and the active ingredients as described above is not essential for working the present invention.

The compositions according to the invention can also comprise further solid or liquid auxiliaries, such as stabilizers, for example unepoxidized or epoxidized vegetable oils (for example epoxidized coconut oil, rapeseed oil or soya oil), antifoams, for example silicone oil, preservatives, viscosity regulators, binders and/or tackifiers, fertilizers or other active ingredients for achieving specific effects, for example bactericides, fungicides, nematocides, plant activators, molluscicides or herbicides.

The compositions according to the invention are prepared in a manner known per se, in the absence of auxiliaries for example by grinding, screening and/or compressing a solid active ingredient and in the presence of at least one auxiliary for example by intimately mixing and/or grinding the active ingredient with the auxiliary (auxiliaries). These processes for the preparation of the compositions and the use of the compounds I for the preparation of these compositions are also a subject of the invention.

The application methods for the compositions, that is the methods of controlling pests of the abovementioned type, such as spraying, atomizing, dusting, brushing on, dressing, scattering or pouring—which are to be selected to suit the intended aims of the prevailing circumstances—and the use of the compositions for controlling pests of the abovementioned type are other subjects of the invention. Typical rates of concentration are between 0.1 and 1000 ppm, preferably between 0.1 and 500 ppm, of active ingredient. The rate of application per hectare is generally 1 to 2000 g of active ingredient per hectare, in particular 10 to 1000 g/ha, preferably 10 to 600 g/ha.

A preferred method of application in the field of crop protection is application to the foliage of the plants (foliar application), it being possible to select frequency and rate of application to match the danger of infestation with the pest in question. Alternatively, the active ingredient can reach the plants via the root system (systemic action), by drenching the locus of the plants with a liquid composition or by incorporating the active ingredient in solid form into the locus of the plants, for example into the soil, for example in the form of granules (soil application). In the case of paddy rice crops, such granules can be metered into the flooded paddy-field.

The compounds of the invention and compositions thereof are also be suitable for the protection of plant propagation material, for example seeds, such as fruit, tubers or kernels, or nursery plants, against pests of the abovementioned type. The propagation material can be treated with the compound prior to planting, for example seed can be treated prior to sowing. Alternatively, the compound can be applied to seed kernels (coating), either by soaking the kernels in a liquid composition or by applying a layer of a solid composition. It is also possible to apply the compositions when the propagation material is planted to the site of application, for example into the seed furrow during drilling. These treatment methods for plant propagation material and the plant propagation material thus treated are further subjects of the invention. Typical treatment rates would depend on the plant and pest/fungi to be controlled and are generally between 1 to 200 grams per 100 kg of seeds, preferably between 5 to 150 grams per 100 kg of seeds, such as between 10 to 100 grams per 100 kg of seeds.

The term seed embraces seeds and plant propagules of all kinds including but not limited to true seeds, seed pieces, suckers, corns, bulbs, fruit, tubers, grains, rhizomes, cuttings, cut shoots and the like and means in a preferred embodiment true seeds.

The present invention also comprises seeds coated or treated with or containing a compound of formula I. The term "coated or treated with and/or containing" generally signifies that the active ingredient is for the most part on the surface of the seed at the time of application, although a greater or lesser part of the ingredient may penetrate into the seed material, depending on the method of application. When the said seed product is (re)planted, it may absorb the active ingredient. In an embodiment, the present invention makes available a plant propagation material adhered thereto with a compound of formula (I). Further, it is hereby made available, a composition comprising a plant propagation material treated with a compound of formula (I).

Seed treatment comprises all suitable seed treatment techniques known in the art, such as seed dressing, seed coating, seed dusting, seed soaking and seed pelleting. The seed treatment application of the compound formula (I) can be carried out by any known methods, such as spraying or by dusting the seeds before sowing or during the sowing/planting of the seeds.

BIOLOGICAL EXAMPLES

Example B1

*Bemisia tabaci* (Cotton White Fly): Feeding/Contact Activity

Cotton leaf discs were placed on agar in 24-well microtiter plates and sprayed with aqueous test solutions prepared from 10,000 ppm DMSO stock solutions. After drying the leaf discs were infested with adult white flies. The samples were checked for mortality 6 days after incubation.

The following compounds resulted in at least 80% mortality at an application rate of 200 ppm:

A1, A5, A6, A7, A8, A9, A11, A13, A14, A15, A18, A19, A22, A23, A24, A27, A28, A29, A31, A30 and A42.

Example B2

*Diabrotica balteata* (Corn Root Worm)

Maize sprouts placed onto an agar layer in 24-well microtiter plates were treated with aqueous test solutions prepared from 10,000 ppm DMSO stock solutions by spraying. After drying, the plates were infested with L2 larvae (6 to 10 per well). The samples were assessed for mortality and growth inhibition in comparison to untreated samples 4 days after infestation.

The following compounds gave an effect of at least 80% in at least one of the two categories (mortality or growth inhibition) at an application rate of 200 ppm:

A1, A3, A5, A6, A7, A8, A9, A10, A11, A14, A15, A16, A17, A18, A19, A21, A22, A23, A24, A25, A26, A27, A28, A29, A30, A31, A32, A34, A36, A37, A38, A39, A40, A41, A42 and A43.

Example B3

*Euschistus heros* (Neotropical Brown Stink Bug)

Soybean leaves on agar in 24-well microtiter plates were sprayed with aqueous test solutions prepared from 10,000 ppm DMSO stock solutions. After drying the leaves were infested with N2 nymphs. The samples were assessed for mortality and growth inhibition in comparison to untreated samples 5 days after infestation.

The following compounds gave an effect of at least 80% in at least one of the two categories (mortality or growth inhibition) at an application rate of 200 ppm:

A1, A3, A5, A6, A7, A8, A9, A10, A11, A12, A13, A14, A15, A16, A17, A18, A19, A21, A22, A23, A24, A25, A26, A27, A28, A29, A30, A31, A32, A34, A36, A37, A39, A40, A41 and A42.

Example B4

*Frankliniella occidentalis* (Western Flower Thrips): Feeding/Contact Activity

Sunflower leaf discs were placed on agar in 24-well microtiter plates and sprayed with aqueous test solutions prepared from 10,000 DMSO stock solutions. After drying the leaf discs were infested with a *Frankliniella* population of mixed ages. The samples were assessed for mortality 7 days after infestation.

The following compounds resulted in at least 80% mortality at an application rate of 200 ppm:

A1, A6, A7, A8, A9, A11, A13, A16, A19, A22, A24, A26, A27, A28, A29, A30, A31, A34, A39, A41 and A42.

Example B5

*Myzus persicae* (Green Peach Aphid): Feeding/Contact Activity

Sunflower leaf discs were placed onto agar in a 24-well microtiter plate and sprayed with aqueous test solutions prepared from 10,000 ppm DMSO stock solutions. After drying, the leaf discs were infested with an aphid population of mixed ages. The samples were assessed for mortality 6 days after infestation.

The following compounds resulted in at least 80% mortality at an application rate of 200 ppm:

A1, A5, A6, A7, A8, A9, A11, A12, A13, A14, A16, A21, A22, A23, A24, A26, A27, A28, A29, A30, A31, A32, A34, A36, A39, A42 and A43.

*Myzus persicae* (Green Peach Aphid). Systemic Activity

Roots of pea seedlings infested with an aphid population of mixed ages were placed directly into aqueous test solutions prepared from 10,000 DMSO stock solutions. The samples were assessed for mortality 6 days after placing seedlings into test solutions.

The following compounds resulted in at least 80% mortality at a test rate of 24 ppm:

A13, A31 and A32.

Example B6

*Plutella xylostella* (Diamond Back Moth)

24-well microtiter plates with artificial diet were treated with aqueous test solutions prepared from 10,000 ppm DMSO stock solutions by pipetting. After drying, the plates were infested with L2 larvae (10 to 15 per well). The samples were assessed for mortality and growth inhibition in comparison to untreated samples 5 days after infestation.

The following compounds gave an effect of at least 80% in at least one of the two categories (mortality or growth inhibition) at an application rate of 200 ppm:

A1, A3, A5, A6, A7, A8, A9, A10, A11, A12, A13, A14, A15, A16, A17, A18, A19, A20, A21, A22, A23, A24, A25, A26, A27, A28, A29, A30, A31, A32, A34, A36, A38, A39, A40, A41, A42 and A43.

Example B7

*Spodoptera littoralis* (Egyptian Cotton Leaf Worm)

Cotton leaf discs were placed onto agar in 24-well microtiter plates and sprayed with aqueous test solutions prepared from 10,000 ppm DMSO stock solutions. After drying the leaf discs were infested with five L1 larvae. The samples were assessed for mortality, anti-feeding effect, and growth inhibition in comparison to untreated samples 3 days after infestation. Control of *Spodoptera littoralis* by a test sample is given when at least one of the categories mortality, anti-feedant effect, and growth inhibition is higher than the untreated sample.

The following compounds resulted in at least 80% control at an application rate of 200 ppm:

A1, A3, A5, A6, A7, A8, A9, A10, A11, A12, A13, A14, A15, A16, A17, A18, A19, A20, A21, A22, A23, A24, A25, A26, A27, A28, A29, A30, A31, A32, A34, A36, A37, A38, A39, A40, A41, A42 and A43.

Example B8

*Spodoptera littoralis* (Egyptian Cotton Leaf Worm)

Test compounds were applied by pipette from 10,000 ppm DMSO stock solutions into 24-well plates and mixed with agar. Lettuce seeds were placed onto the agar and the multi well plate was closed by another plate which contained also agar. After 7 days the compound was absorbed by the roots and the lettuce grew into the lid plate. The lettuce leaves were then cut off into the lid plate. *Spodoptera* eggs were pipetted through a plastic stencil onto a humid gel blotting paper and the lid plate was closed with it. The samples were assessed for mortality, anti-feedant effect and growth inhibition in comparison to untreated samples 6 days after infestation.

The following compounds gave an effect of at least 80% in at least one of the three categories (mortality, anti-feeding, or growth inhibition) at a test rate of 12.5 ppm:

A1, A5, A6, A8, A9, A11, A15, A24, A30, A31, A32, A34, A36, A39, A40, A41, A42 and A43.

Example B9

*Tetranychus urticae* (Two-Spotted Spider Mite): Feeding/Contact Activity

Bean leaf discs on agar in 24-well microtiter plates were sprayed with aqueous test solutions prepared from 10,000 ppm DMSO stock solutions. After drying the leaf discs were infested with a mite population of mixed ages. The samples were assessed for mortality on mixed population (mobile stages) 8 days after infestation.

The following compounds resulted in at least 80% mortality at an application rate of 200 ppm:

A11, A26, A31 and A32.

Example B10

*Thrips tabaci* (Onion Thrips) Feeding/Contact Activity

Sunflower leaf discs were placed on agar in 24-well microtiter plates and sprayed with aqueous test solutions prepared from 10,000 ppm DMSO stock solutions. After drying the leaf discs were infested with a thrips population of mixed ages. The samples were assessed for mortality 6 days after infestation.

The following compounds resulted in at least 80% mortality at an application rate of 200 ppm:

A1, A5, A6, A11, A14, A16, A21, A22, A24, A26, A31 and A32.

Example B11

*Aedes aegypti* (Yellow Fever Mosquito)

Test solutions, at an application rate of 200 ppm in ethanol, were applied to 12 well tissue culture plates. Once the deposits were dry, five, two to five day old adult female *Aedes aegypti* were added to each well, and sustained with a 10% sucrose solution in a cotton wool plug. Assessment of knockdown was made one hour after introduction, and mortality was assessed at 24 and 48 hours after introduction.

The following compounds gave at least 80% control of *Aedes aegypti* after 48 h and/or 24 h:

A1, A3, A5, A6, A7, A9, A11, A24, A28, A30, A31, A32, A34, A36 and A38.

Example B12

*Anopheles stephensi* (Indian Malaria Mosquito)

Test solutions, at an application rate of 200 ppm in ethanol, were applied to 12 well tissue culture plates. Once the deposits were dry, five, two to five day old adult female *Anopheles stephensi* were added to each well, and sustained with a 10% sucrose solution in a cotton wool plug. Assessment of knockdown was made one hour after introduction, and mortality was assessed at 24 and 48 hours after introduction.

The following compounds gave at least 80% control of *Anopheles stephensi* after 48 h and/or 24 h:

A1, A3, A5, A6, A7, A9, A11, A24, A28, A30, A31, A32, A34 and A36.

The invention claimed is:

1. A compound of formula I,

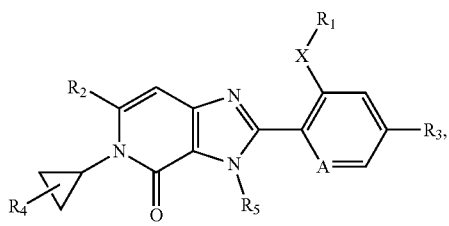

(I)

wherein
A is CH or N;
X is S, SO or $SO_2$;
$R_1$ is $C_1$-$C_4$alkyl;
$R_2$ is $C_1$-$C_6$haloalkyl, $C_1$-$C_6$haloalkoxy, $C_1$-$C_4$haloalkylsulfanyl, $C_1$-$C_4$haloalkylsulfinyl or $C_1$-$C_4$haloalkylsulfonyl; or
$R_2$ is cyclopropyl which can be mono- or polysubstituted by substituents selected from the group consisting of halogen, cyano, $C_1$-$C_4$ haloalkyl and $C_1$-$C_4$alkyl;
$R_3$ is hydrogen, halogen, cyano, $C_1$-$C_4$haloalkyl, $C_1$-$C_4$haloalkylsulfanyl, $C_1$-$C_4$haloalkylsulfinyl or $C_1$-$C_4$haloalkylsulfonyl; or is $C_3$-$C_6$cycloalkyl which can be mono- or polysubstituted by substituents selected from the group consisting of halogen, $C_1$-$C_4$alkyl, $C_1$-$C_4$haloalkyl and cyano; or
$R_3$ is phenyl which can be mono- or polysubstituted by substituents selected from the group consisting of halogen, cyano, nitro, $C_2$-$C_6$alkenyl, $C_2$-$C_6$haloalkenyl, $C_2$-$C_6$alkynyl, $C_2$-$C_6$haloalkynyl, $C_1$-$C_4$alkoxy$C_1$-$C_4$alkyl, $C_1$-$C_4$alkyl, $C_1$-$C_4$haloalkyl, $C_1$-$C_4$haloalkoxy, $C_1$-$C_4$alkoxy, $C_1$-$C_4$haloalkylsulfanyl, $C_1$-$C_4$haloalkylsulfinyl, $C_1$-$C_4$haloalkylsulfonyl, $C_1$-$C_4$alkylsulfanyl, $C_1$-$C_4$alkylsulfinyl, $C_1$-$C_4$alkylsulfonyl and $C(O)C_1$-$C_4$haloalkyl; or
$R_3$ is pyrimidinyl or pyridinyl linked via a carbon atom to the ring which contains the substituent A, said pyrimidinyl or pyridinyl can be mono- or polysubstituted by substituents selected from the group
consisting of halogen, cyano, nitro, $C_2$-$C_6$alkenyl, $C_2$-$C_6$haloalkenyl, $C_2$-$C_6$alkynyl, $C_2$-$C_6$haloalkynyl, $C_1$-$C_4$alkoxy$C_1$-$C_4$alkyl, $C_1$-$C_4$alkyl, $C_1$-$C_4$haloalkyl, $C_1$-$C_4$haloalkoxy, $C_1$-$C_4$alkoxy, $C_1$-$C_4$haloalkylsulfanyl, $C_1$-$C_4$haloalkylsulfinyl, $C_1$-$C_4$haloalkylsulfonyl, $C_1$-$C_4$alkylsulfanyl, $C_1$-$C_4$alkylsulfinyl, $C_1$-$C_4$alkylsulfonyl and —$C(O)C_1$-$C_4$haloalkyl; or
$R_3$ is a five membered, aromatic ring system linked via a nitrogen atom to the ring which contains the substituent A, said ring system can be mono- or polysubstituted by substituents selected from the group consisting of halogen, cyano, nitro, $C_2$-$C_6$alkenyl, $C_2$-$C_6$haloalkenyl, $C_2$-$C_6$alkynyl, $C_2$-$C_6$haloalkynyl, $C_1$-$C_4$alkoxy$C_1$-$C_4$alkyl, $C_1$-$C_4$alkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl, —$C(O)C_1$-$C_4$alkyl, $C_1$-$C_4$haloalkylsulfanyl, $C_1$-$C_4$haloalkylsulfinyl, $C_1$-$C_4$haloalkylsulfonyl and —$C(O)C_1$-$C_4$haloalkyl; and
said ring system contains 1, 2 or 3 heteroatoms selected from the group consisting of nitrogen, oxygen and sulphur, where said ring system may not contain more than one oxygen atom and not more than one sulfur atom;
$R_4$ is hydrogen, halogen, cyano, $C_1$-$C_4$alkyl or $C_1$-$C_4$haloalkyl; and
$R_5$ is $C_1$-$C_4$alkyl; and agrochemically acceptable salts, stereoisomers, enantiomers, tautomers and N-oxides of the compounds of formula I.

2. A compound of formula I according to claim 1, wherein
$R_1$ is $C_1$-$C_4$alkyl;
$R_2$ is $C_1$-$C_6$haloalkyl, $C_1$-$C_4$haloalkylsulfanyl, $C_1$-$C_4$haloalkylsulfinyl, $C_1$-$C_4$haloalkylsulfonyl or cyclopropane, said cyclopropane can be mono- or polysubstituted by substituents selected from the group consisting of halogen, cyano, $C_1$-$C_4$ haloalkyl and $C_1$-$C_4$alkyl;
$R_3$ is hydrogen, halogen, cyano, $C_1$-$C_6$haloalkyl, $C_3$-$C_6$cycloalkyl, $C_1$-$C_6$haloalkylsulfanyl, $C_1$-$C_6$haloalkylsulfinyl, $C_1$-$C_6$haloalkylsulfonyl, $C_1$-$C_6$haloalkoxy, —C(O)$C_1$-$C_4$haloalkyl, $C_1$-$C_6$alkylsulfanyl, $C_1$-$C_6$alkylsulfinyl or $C_1$-$C_6$alkylsulfonyl; or is $C_3$-$C_6$cycloalkyl which can be mono- or polysubstituted by substituents selected from the group consisting of halogen, $C_1$-$C_4$alkyl, $C_1$-$C_4$haloalkyl and cyano; or $R_3$ is phenyl which can be mono- or polysubstituted by substituents selected from the group consisting of halogen, cyano, nitro, $C_2$-$C_6$alkenyl, $C_2$-$C_6$haloalkenyl, $C_2$-$C_6$alkynyl, $C_2$-$C_6$haloalkynyl, $C_1$-$C_4$alkoxy $C_1$-$C_4$alkyl, $C_1$-$C_4$alkyl, $C_1$-$C_4$haloalkyl, $C_1$-$C_4$haloalkoxy, $C_1$-$C_4$alkoxy, $C_1$-$C_4$haloalkylsulfanyl, $C_1$-$C_4$haloalkylsulfinyl, $C_1$-$C_4$haloalkylsulfonyl, $C_1$-$C_4$alkylsulfanyl, $C_1$-$C_4$alkylsulfinyl, $C_1$-$C_4$alkylsulfonyl and —C(O)$C_1$-$C_4$haloalkyl; or $R_3$ is pyrimidinyl or pyridinyl linked via a carbon atom to the ring which contains the substituent A, said pyrimidinyl or pyridinyl can be mono- or polysubstituted by substituents selected from the group consisting of halogen, cyano, nitro, $C_2$-$C_6$alkenyl, $C_2$-$C_6$haloalkenyl, $C_2$-$C_6$alkynyl, $C_2$-$C_6$haloalkynyl, $C_1$-$C_4$alkoxy $C_1$-$C_4$alkyl, $C_1$-$C_4$alkyl, $C_1$-$C_4$haloalkyl, $C_1$-$C_4$haloalkoxy, $C_1$-$C_4$alkoxy, $C_1$-$C_4$haloalkylsulfanyl, $C_1$-$C_4$haloalkylsulfinyl, $C_1$-$C_4$haloalkylsulfonyl, $C_1$-$C_4$alkylsulfanyl, $C_1$-$C_4$alkylsulfinyl, $C_1$-$C_4$alkylsulfonyl and —C(O)$C_1$-$C_4$haloalkyl; or $R_3$ is a pyrazolyl- or a triazolyl ring system linked via a nitrogen atom to the ring which contains the substituent $G_3$, said ring system can be mono- or polysubstituted by substituents selected from the group consisting of halogen, cyano, nitro, $C_2$-$C_6$alkenyl, $C_2$-$C_6$haloalkenyl, $C_2$-$C_6$alkynyl, $C_2$-$C_6$haloalkynyl, $C_1$-$C_4$alkoxy $C_1$-$C_4$alkyl, $C_1$-$C_4$alkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl and —C(O)$C_1$-$C_4$alkyl, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl; and said ring system contains 1, 2 or 3 heteroatoms selected from the group consisting of nitrogen, oxygen and sulphur, where said ring system may not contain more than one oxygen atom and not more than one sulfur atom;

$R_4$ is hydrogen, halogen, cyano or $C_1$-$C_4$haloalkyl; and
$R_5$ is $C_1$-$C_4$alkyl.

3. A compound of formula I according to claim 1, wherein
$R_1$ is $C_1$-$C_4$alkyl;
$R_2$ is $C_1$-$C_6$haloalkyl, $C_1$-$C_4$haloalkylsulfanyl, $C_1$-$C_4$haloalkylsulfinyl or $C_1$-$C_4$haloalkylsulfonyl;
$R_3$ is hydrogen, halogen, cyano, $C_1$-$C_6$haloalkyl, $C_3$-$C_6$cycloalkyl, $C_1$-$C_6$haloalkylsulfanyl, $C_1$-$C_6$haloalkylsulfinyl or $C_1$-$C_6$haloalkylsulfonyl; or is $C_3$-$C_6$cycloalkyl which can be mono- or polysubstituted by substituents selected from the group consisting of halogen, $C_1$-$C_4$alkyl, $C_1$-$C_4$haloalkyl and cyano; or
$R_3$ is phenyl which can be mono- or polysubstituted by substituents selected from the group consisting of halogen, cyano, $C_1$-$C_4$haloalkyl, $C_1$-$C_4$haloalkylsulfanyl, $C_1$-$C_4$haloalkylsulfinyl, $C_1$-$C_4$haloalkylsulfonyl, $C_1$-$C_4$alkylsulfanyl, $C_1$-$C_4$alkylsulfinyl and $C_1$-$C_4$alkylsulfonyl; or
$R_3$ is pyrimidinyl or pyridinyl which both can be mono- or polysubstituted by substituents selected from the group consisting of halogen, cyano, $C_1$-$C_4$haloalkyl, $C_1$-$C_4$haloalkylsulfanyl, $C_1$-$C_4$haloalkylsulfinyl, $C_1$-$C_4$haloalkylsulfonyl, $C_1$-$C_4$alkylsulfanyl, $C_1$-$C_4$alkylsulfinyl and $C_1$-$C_4$alkylsulfonyl; or
$R_3$ is a pyrazolyl- or a triazolyl ring system linked via a nitrogen atom to the ring which contains the substituent $G_3$, said ring system can be mono- or polysubstituted by substituents selected from the group consisting of halogen, cyano, $C_1$-$C_4$haloalkyl, $C_1$-$C_4$haloalkylsulfanyl, $C_1$-$C_4$haloalkylsulfinyl, $C_1$-$C_4$haloalkylsulfonyl, $C_1$-$C_4$alkylsulfanyl, $C_1$-$C_4$alkylsulfinyl and $C_1$-$C_4$alkylsulfonyl; and said ring system contains 1, 2 or 3 heteroatoms selected from the group consisting of nitrogen, oxygen and sulphur, where said ring system may not contain more than one oxygen atom and not more than one sulfur atom;
$R_4$ is hydrogen, halogen, cyano or $C_1$-$C_4$haloalkyl; and
$R_5$ is $C_1$-$C_4$alkyl.

4. A compound of formula I according to claim 1, wherein
$R_1$ is ethyl or methyl;
$R_2$ is $C_1$-$C_6$haloalkyl;
$R_3$ is hydrogen, halogen, $C_1$-$C_6$haloalkyl, $C_3$-$C_6$cycloalkyl, $C_1$-$C_6$haloalkylsulfanyl, $C_1$-$C_6$haloalkylsulfinyl or $C_1$-$C_6$haloalkylsulfonyl; or
$R_3$ is phenyl which can be mono- or polysubstituted by substituents selected from the group consisting of halogen, cyano, $C_1$-$C_4$haloalkyl, $C_1$-$C_4$haloalkylsulfanyl, $C_1$-$C_4$haloalkylsulfinyl, $C_1$-$C_4$haloalkylsulfonyl, $C_1$-$C_4$alkylsulfanyl, $C_1$-$C_4$alkylsulfinyl and $C_1$-$C_4$alkylsulfonyl; or
$R_3$ is pyrimidinyl or pyridinyl linked via a carbon atom to the ring which contains the substituent A, said pyrimidinyl or pyridinyl can be mono- or polysubstituted by substituents selected from the group
consisting of halogen, cyano, $C_1$-$C_4$haloalkyl, $C_1$-$C_4$haloalkylsulfanyl, $C_1$-$C_4$haloalkylsulfinyl, $C_1$-$C_4$haloalkylsulfonyl, $C_1$-$C_4$alkylsulfanyl, $C_1$-$C_4$alkylsulfinyl and $C_1$-$C_4$alkylsulfonyl; or
$R_3$ is a pyrazolyl- or a triazolyl ring system linked via a nitrogen atom to the ring which contains the substituent $G_3$, said ring system can be mono- or polysubstituted by substituents selected from the group consisting of halogen, cyano, $C_1$-$C_4$haloalkyl, $C_1$-$C_4$haloalkylsulfanyl, $C_1$-$C_4$haloalkylsulfinyl, $C_1$-$C_4$haloalkylsulfonyl, $C_1$-$C_4$alkylsulfanyl, $C_1$-$C_4$alkylsulfinyl and $C_1$-$C_4$alkylsulfonyl; and said ring system contains 1, 2 or 3 heteroatoms selected from the group consisting of nitrogen, oxygen and sulphur, where said ring system may not contain more than one oxygen atom and not more than one sulfur atom;
$R_4$ is hydrogen; and
$R_5$ is $C_1$-$C_4$alkyl.

5. A compound of formula I according to claim 1, wherein
$R_1$ is ethyl or methyl;
$R_2$ is $CF_3$;
$R_3$ is hydrogen, halogen, $C_1$-$C_2$haloalkyl, cyclopropane, trifluoromethylsulfanyl, trifluoromethylsulfinyl or trifluoromethylsulfonyl; or
$R_3$ is phenyl which can be mono- or polysubstituted by substituents selected from the group consisting of halogen, cyano, $C_1$-$C_2$haloalkyl, trifluoromethylsulfanyl, trifluoromethylsulfinyl, trifluoromethylsulfonyl and $C_1$-$C_2$alkylsulfanyl; or
$R_3$ is pyrimidinyl or pyridinyl linked via a carbon atom to the ring which contains the substituent A, said pyrimidinyl or pyridinyl can be mono- or polysubstituted by substituents selected from the group consisting of halogen, cyano, $C_1$-$C_2$haloalkyl, trifluoromethylsulfanyl, trifluoromethylsulfinyl, trifluoromethylsulfonyl and $C_1$-$C_2$alkylsulfanyl; or $R_3$ is a pyrazolyl- or a triazolyl ring system linked via a nitrogen atom to the ring which contains the substituent $G_3$, said ring system can be mono- or polysubstituted by substituents selected from the group consisting of halogen, cyano, $C_1$-$C_2$haloalkyl, trifluoromethylsulfanyl, trifluoromethylsulfinyl, trifluoromethylsulfonyl and $C_1$-$C_2$alkylsulfanyl; and said ring system contains 1, 2 or 3 heteroatoms selected from the group consisting of nitrogen, oxygen and sulphur, where said ring system may not contain more than one oxygen atom and not more than one sulfur atom;

$R_4$ is hydrogen; and $R_5$ is $C_1$-$C_4$alkyl.

6. A compound of formula I according to claim 1, wherein $R_1$ is ethyl;

$R_2$ is $CF_3$;

$R_3$ is hydrogen, halogen, trifluoromethyl, pentafluoroethyl, cyclopropane, trifluoromethylsulfanyl, trifluoromethylsulfinyl or trifluoromethylsulfonyl; or $R_3$ is phenyl which can be mono- or polysubstituted by substituents selected from the group consisting of halogen, cyano, trifluoromethyl, trifluoromethylsulfanyl, trifluoromethylsulfinyl, trifluoromethylsulfonyl and methylsulfanyl; or $R_3$ is pyrimidinyl or pyridinyl linked via a carbon atom to the ring which contains the substituent A, said pyrimidinyl or pyridinyl can be mono- or polysubstituted by substituents selected from the group consisting of halogen, cyano, trifluoromethyl, trifluoromethylsulfanyl, trifluoromethylsulfinyl, trifluoromethylsulfonyl and methylsulfanyl; or $R_3$ is a pyrazolyl- or a triazolyl ring system linked via a nitrogen atom to the ring which contains the substituent $G_3$, said ring system can be mono- or polysubstituted by substituents selected from the group consisting of halogen, cyano, trifluoromethyl, trifluoromethylsulfanyl, trifluoromethylsulfinyl, trifluoromethylsulfonyl and methylsulfanyl; and said ring system contains 1, 2 or 3 heteroatoms selected from the group consisting of nitrogen, oxygen and sulphur, where said ring system may not contain more than one oxygen atom and not more than one sulfur atom;

$R_4$ is hydrogen; and $R_5$ is methyl.

7. A compound of formula I according to claim 1, wherein

A is CH or N;

X is S, SO or $SO_2$;

$R_1$ is $C_1$-$C_4$alkyl;

$R_2$ is $CF_3$;

$R_3$ is hydrogen, halogen or $C_1$-$C_4$haloalkyl; or $R_3$ is cyclopropane which can be mono-substituted by cyano; or $R_3$ is phenyl which can be mono- or polysubstituted by substituents selected from the group consisting of halogen, cyano, $C_1$-$C_2$haloalkyl, $C_1$-$C_2$halomethoxy, $C_1$-$C_2$alkoxy and $C_1$-$C_2$sulfanyl; or $R_3$ is pyrimidinyl or pyridinyl linked via a carbon atom to the ring which contains the substituent A, said pyrimidinyl or pyridinyl can be mono- or polysubstituted by substituents selected from the group consisting of halogen, cyano, $C_1$-$C_2$haloalkyl, $C_1$-$C_2$alkoxy; or $R_3$ is a pyrazolyl- or a triazolyl ring system linked via a nitrogen atom to the ring, said ring system can be mono- or polysubstituted by substituents selected from the group consisting of halogen, cyano and $C_1$-$C_2$haloalkyl;

$R_4$ is hydrogen; and $R_5$ is methyl.

8. A pesticidal composition, which comprises at least one compound of formula I according to claim 1 or, where appropriate, a tautomer thereof, in each case in free form or in agrochemically utilizable salt form, as active ingredient and at least one auxiliary.

9. A method for controlling pests, which comprises applying a composition according to claim 8 to the pests or their environment with the exception of a method for treatment of the human or animal body by surgery or therapy and diagnostic methods practised on the human or animal body.

10. A method for the protection of plant propagation material from the attack by pests, which comprises treating the propagation material or the site, where the propagation material is planted, with a composition according to claim 8.

11. Plant propagation material treated in accordance with the method described in claim 10.

12. The compound of claim 1, wherein $R_2$ is $CF_3$, $R_4$ is H, and $R_5$ is methyl.

\* \* \* \* \*